United States Patent
Bonaventure et al.

(10) Patent No.: US 12,378,306 B2
(45) Date of Patent: Aug. 5, 2025

(54) ANTI-FUNGAL VHH ANTIBODIES

(71) Applicant: Biotalys NV, Ghent (BE)

(72) Inventors: Gustavo Bonaventure, Aachen (DE); Jan Jozef Lutgart Geerinck, Sint Niklaas (BE); David Jose De Sousa Felix, Ghent (BE)

(73) Assignee: BIOTALYS NV, Ghent (BE)

( * ) Notice: Subject to any disclaimer, the term of this patent is extended or adjusted under 35 U.S.C. 154(b) by 0 days.

(21) Appl. No.: 18/999,710

(22) Filed: Dec. 23, 2024

(65) Prior Publication Data

US 2025/0206811 A1    Jun. 26, 2025

Related U.S. Application Data

(60) Provisional application No. 63/667,265, filed on Jul. 3, 2024, provisional application No. 63/667,277, filed on Jul. 3, 2024, provisional application No. 63/614,183, filed on Dec. 22, 2023, provisional application No. 63/614,192, filed on Dec. 22, 2023.

(51) Int. Cl.
*C07K 16/14* (2006.01)
*A01N 63/50* (2020.01)

(52) U.S. Cl.
CPC ............ *C07K 16/14* (2013.01); *A01N 63/50* (2020.01); *C07K 2317/14* (2013.01); *C07K 2317/569* (2013.01)

(58) Field of Classification Search
CPC .......................... C07K 16/14; C07K 2317/569
See application file for complete search history.

(56) References Cited

U.S. PATENT DOCUMENTS

2023/0287447 A1*  9/2023  Beloglazova .......... C07K 16/14

FOREIGN PATENT DOCUMENTS

| WO | 2010019442 A1 | 2/2010 | |
|----|---|---|---|
| WO | WO-2014177595 A1 * | 11/2014 | ............ A01N 37/46 |
| WO | 2014191146 A1 | 12/2014 | |
| WO | 2016071438 A2 | 5/2016 | |
| WO | 2021198396 A1 | 10/2021 | |
| WO | 2023057601 A1 | 4/2023 | |

OTHER PUBLICATIONS

Bleackley et al. The interaction with fungal cell wall polysaccharides determines the salt tolerance of antifungal plant defensis. The Cell Surface, 2019, 5(100026), 1-12.
Janeway et al. The interaction of the antibody molecule with specific antigen. Immunobiology: The Immune System in Health and Disease, 2001, 1-6.
Prachayasittikul et al. EDTA-induced Membrane Fluidization and Destabilization: Biophysical Studies on Artificial Lipid Membranes, Acta Biochimica et Biophysica Sinica, 2007, 39(11), 901-913.
De Coninck et al. Fungal Glucosylceramide-Specific Camelid Single Domain Antibodies Are Characterized by Broad Spectrum Antifungal Activity. Frontiers in Microbiology, 2017, 8(1059), 1-10.

* cited by examiner

*Primary Examiner* — Janet L Andres
*Assistant Examiner* — Brian Hartnett
(74) *Attorney, Agent, or Firm* — ARRIGO, LEE, GUTTMAN & MOUTA-BELLUM LLP

(57) ABSTRACT

The present invention relates to a VHH antibody that binds to at least one fungal species and to compositions containing the same. The VHH antibody of the current invention comprises a complementarity determining region 1 (CDR1) region having the amino acid sequence set out in SEQ ID NO: 3; a CDR2 region having the amino acid sequence set out in SEQ ID NO: 4; and a CDR3 region having the amino acid sequence set out in SEQ ID NO: 5. The invention also relates to use of the composition as an anti-fungal agent. The invention further relates to agrochemical compositions and methods of using the same. Additionally, the invention relates to a transgenic plant, plant part, seed, or plant cell. The invention further relates to polynucleotides encoding said VHH antibody. Finally, the invention relates to a method of manufacturing a variant VHH antibody.

13 Claims, 8 Drawing Sheets

Specification includes a Sequence Listing.

SEQUENCE LISTING

```
Sequence total quantity: 15
SEQ ID NO: 1            moltype = DNA  length = 384
FEATURE                 Location/Qualifiers
source                  1..384
                        mol_type = other DNA
                        organism = synthetic construct
SEQUENCE: 1
gacgtacagc tgcaggagtc tgggggagga ttggtgcagg ctggggctc tctgagactc    60
tcctgtgctg cctctagacg taccggcact agatatgtga tggcctggtt ccgccaggct   120
ccagggaagg agcgtgagtt tgtcgcaggt gttgactgga gtggatcggg tcaatactat   180
gcagagtccg tgaagggccg attcaccatc tccaaagaca caccaggaa aacggtgtat    240
cttcagatga acgccctgaa acctgaggac acggccgttt attactgtgc agcaacaagg    300
cgactgtccg ggcgtgccta cttgtgggcc actgcttcga cgtatgacta ctggggccgg   360
gggacccagg tcaccgtctc ctca                                           384

SEQ ID NO: 2            moltype = AA  length = 128
FEATURE                 Location/Qualifiers
source                  1..128
                        mol_type = protein
                        organism = synthetic construct
SEQUENCE: 2
DVQLQESGGG LVQAGGSLRL SCAASRRTGT RYVMAWFRQA PGKEREFVAG VDWSGSGQYY     60
AESVKGRFTI SKDNTRKTVY LQMNALKPED TAVYYCAATR RLSGRAYLWA TASTYDYWGR    120
GTQVTVSS                                                              128

SEQ ID NO: 3            moltype = AA  length = 11
FEATURE                 Location/Qualifiers
source                  1..11
                        mol_type = protein
                        organism = synthetic construct
SEQUENCE: 3
RRTGTRYVMA W                                                          11

SEQ ID NO: 4            moltype = AA  length = 19
FEATURE                 Location/Qualifiers
source                  1..19
                        mol_type = protein
                        organism = synthetic construct
SEQUENCE: 4
AGVDWSGSGQ YYAESVKGR                                                  19

SEQ ID NO: 5            moltype = AA  length = 19
FEATURE                 Location/Qualifiers
source                  1..19
                        mol_type = protein
                        organism = synthetic construct
SEQUENCE: 5
TRRLSGRAYL WATASTYDY                                                  19

SEQ ID NO: 6            moltype = AA  length = 25
FEATURE                 Location/Qualifiers
source                  1..25
                        mol_type = protein
                        organism = synthetic construct
```

-continued

```
SEQUENCE: 6
DVQLQESGGG LVQAGGSLRL SCAAS                                      25

SEQ ID NO: 7              moltype = AA  length = 12
FEATURE                   Location/Qualifiers
source                    1..12
                          mol_type = protein
                          organism = synthetic construct
SEQUENCE: 7
FRQAPGKERE FV                                                    12

SEQ ID NO: 8              moltype = AA  length = 31
FEATURE                   Location/Qualifiers
source                    1..31
                          mol_type = protein
                          organism = synthetic construct
SEQUENCE: 8
FTISKDNTRK TVYLQMNALK PEDTAVYYCA A                               31

SEQ ID NO: 9              moltype = AA  length = 11
FEATURE                   Location/Qualifiers
source                    1..11
                          mol_type = protein
                          organism = synthetic construct
SEQUENCE: 9
WGRGTQVTVS S                                                     11

SEQ ID NO: 10             moltype = DNA  length = 387
FEATURE                   Location/Qualifiers
source                    1..387
                          mol_type = other DNA
                          organism = synthetic construct
SEQUENCE: 10
gacgttcaac tacaggagtc tggtggcggt cttgttcaag ctggaggatc tcttaggctt  60
tcttgtgccg catcccgtag gactggcact agatacgtga tggcatggtt taggcaagct 120
cctggtaaaa aaagggaatt tgtcgctgga gtagattggt ccggctccgg ccaatactac 180
gctgagtctg tgaagggtcg tttcactatc tccaaggata atactaggaa aacggtatac 240
ttgcaaatga acgctttgaa acctgaggat actgcagttt attactgcgc tgcaaccagg 300
aggctgtctg gcagagccta tctgtgggct acagcatcca cttacgacta ttggggaaga 360
ggtactcaag tgaccgtgtc ctcataa                                    387

SEQ ID NO: 11             moltype = DNA  length = 387
FEATURE                   Location/Qualifiers
source                    1..387
                          mol_type = other DNA
                          organism = synthetic construct
SEQUENCE: 11
gacgttcagt tgcaagaatc tggaggaggt ttggttcaag ctggtggttc tttgagattg  60
tcttgtgctg cttctagaag aactggtaca agatacgtta tggcttggtt cagacaagct 120
ccaggtaaaa aaagagagtt tgttgctgga gtggattgga gtggtagtgg tcaatactac 180
gctgaatctg ttaagggtag atttactatt tctaaagata acactagaaa gactgtttac 240
cttcaaatga atgctttgaa gcctgaggat actgccgttt actactgtgc tgctactaga 300
agattgtctg gaagagctta tttgtgggct accgcctcta cttacgatta ttggggtaga 360
ggtactcaag ttactgtctc ttcttaa                                    387

SEQ ID NO: 12             moltype = DNA  length = 387
FEATURE                   Location/Qualifiers
source                    1..387
                          mol_type = other DNA
                          organism = synthetic construct
SEQUENCE: 12
gacgttcaac tccaagagtc aggtggtggt ttggttcagg ctggcggatc tttaggctt   60
tcttgtgcag catccagacg tacaggaaca agatatgtga tggcctggtt cagacaggct 120
cctggtaagg aacgtgaatt cgttgctgga gtcgattggt caggtagcgg tcaatactac 180
gcagaatccg ttaagggtcg atttacgatc agtaaagata acactagaaa accgtctat  240
ttgcaaatga atgctctgaa accagaggac acagctgtat actactgcgc agctactaga 300
cgtttgagcg gtagggcata cctatgggcc actgcttcga cttatgacta ttggggtaga 360
ggaacacaag ttaccgtgtc ctcttaa                                    387

SEQ ID NO: 13             moltype = DNA  length = 387
FEATURE                   Location/Qualifiers
source                    1..387
                          mol_type = other DNA
                          organism = synthetic construct
SEQUENCE: 13
gacgtccagc tccaggagag cggcggcggc ctcgtccagg ctgcggcag cctccgcctc   60
agctgcgccg cctctcgccg caccggcacg cgctacgtca tggcctggtt ccgacaggcc 120
cctggcaagg agcgcgagtt cgtcgccggc gtcgactggt ccggcagcgg ccagtactac 180
gccgagagcg tcaagggccg cttcaccatc agcaaggaca cacccgcaa gaccgtctac  240
```

```
ctccagatga acgccctcaa gcctgaggac accgccgtct actactgcgc cgctacgcgc   300
cgactcagcg gccgagccta cctctgggcc accgccagca cctacgacta ctggggccga   360
ggcacccagg tcaccgtcag cagctaa                                       387

SEQ ID NO: 14           moltype = DNA  length = 387
FEATURE                 Location/Qualifiers
source                  1..387
                        mol_type = other DNA
                        organism = synthetic construct
SEQUENCE: 14
gacgtccaat tacaagagag tggcggcgga ttggtacagg ctggaggatc actgagacta   60
tcgtgcgcag caagccggcg aaccggtacc cgatacgtga tggcgtggtt tagacaggcc   120
ccggggaagg aaagggaatt cgttgccggc gttgactggt ctggctccgg ccagtactat   180
gccgagtctg tcaagggtcg cttcaccatc tcgaaggata acacgcgcaa gaccgtgtac   240
ctccaaatga acgcccttaa acccgaggac actgctgtct actactgcgc cgcgacgcgc   300
cgtctgagcg gccgcgcgta tctctgggct acggcctcca cttacgacta ttggggccgg   360
gggacacagg tcacagtcag ctcctaa                                       387

SEQ ID NO: 15           moltype = DNA  length = 387
FEATURE                 Location/Qualifiers
source                  1..387
                        mol_type = other DNA
                        organism = synthetic construct
SEQUENCE: 15
gatgtccaac tgcaagaatc aggcggaggc ctggttcaag caggcggatc actgagactg   60
tcatgcgcag catcaagaag aacaggcaca agatatgtta tggcgtggtt tagacaagca   120
ccgggaaaag aaagagaatt tgttgcaggc gttgattggt caggctcagg ccaatattat   180
gcagaatcag ttaaaggacg cttcacgatc agcaaagata atacacgcaa aacagtctac   240
ctgcaaatga atgcactgaa accggaagat acagcagtct attattgcgc agcaacacgc   300
agactgtcag gcagagcata tctgtgggca acagcatcaa catatgatta ttggggcaga   360
ggcacacaag ttacagtttc atcataa                                       387
```

ANTI-FUNGAL VHH ANTIBODIES

CROSS-REFERENCE TO RELATED APPLICATIONS

This application claims the benefit of U.S. Provisional Application 63/614,192 filed on Dec. 22, 2023, U.S. Provisional Application 63/667,265 filed on Jul. 3, 2024, U.S. Provisional Application 63/614,183 filed on Dec. 22, 2023, and U.S. Provisional Application 63/667,277 filed on Jul. 3, 2024, the contents of each of which are incorporated herein by reference in their entireties for all purposes.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Dec. 23, 2024, is named PAT2618659US00_SeqList.xml and is 16,591 bytes in size.

FIELD OF THE INVENTION

The present invention relates to a VHH antibody that binds to at least one fungal species and to compositions containing the same. The VHH antibody of the current invention comprises a complementarity determining region 1 (CDR1) region having the amino acid sequence set out in SEQ ID NO: 3; a CDR2 region having the amino acid sequence set out in SEQ ID NO: 4; and a CDR3 region having the amino acid sequence set out in SEQ ID NO: 5. The invention also relates to use of the composition as an anti-fungal agent. The invention further relates to agrochemical compositions and methods of using the same. Additionally, the invention relates to a transgenic plant, plant part, seed, or plant cell. The invention further relates to polynucleotides encoding said VHH antibody. Finally, the invention relates to a method of manufacturing a variant VHH antibody.

The current invention is therefore situated in the field of VHH antibodies. More specifically, VHH antibodies that bind to at least one fungal species. The current invention situated in the field of antifungal compositions and methods of using said antifungal compositions. The current invention is also situated in the field of protecting or treating crops or plants from a plant pathogenic fungal infection.

BACKGROUND

The presence and persistence of pathogenic fungal infections seen in patients and animals but also in plant crops can be mainly attributed to the selective pressure of broad-spectrum anti-fungals and the general lack of efficacy of anti-fungal agents, which are available at present.

In humans and animals, systemic fungal infections such as invasive candidiasis and invasive aspergillosis may be caused by a variety of fungal pathogens, for example the virulent *Candida* species *C. albicans, C. tropicalis* and *C. krusei* and the less virulent species *C. parapsilosis* and *Torulopsis glabrata* (the latter sometimes referred to as *Candida glabrata*). Although *C. albicans* was once the most common fungal isolate obtained from intensive care units, later studies have indicated that *C. tropicalis, C. glabrata, C. parapsilosis* and *C. krusei* now account for about half of such isolates. The rise of non-*albicans* species implies the emergence of *Candida* species resistant to conventional antifungal therapy.

Traditionally, *C. albicans, C. tropicalis* and *C. parapsilosis* have been treated by the antifungal agent amphotericin B, regarded as the "gold standard" of systemic antifungal therapy. Unfortunately, amphotericin B is itself highly toxic and its use is tempered by side effects including chills, fever, myalgia or thrombophlebitis. Other anti-fungal agents include the oral azole drugs (miconazole, ketoconazole, itraconazole, fluconazole) and 5-fluorocytosine. However, fungal species such as *C. krusei* and *T. glabrata* are resistant to fluconazole, and these species often occur in patients where this drug has been administered prophylactically. Furthermore, fluconazole-resistant strains of *C. albicans* have also been reported. Thus, despite the advances made in therapeutic anti-fungal drugs, the need for effective agents for treatment of fungal infections remains acute.

In agriculture, crop protection relies heavily on the use of pesticides, which are applied to the crops by spraying them onto the crop, applying during watering of the crops or incorporating them into the soil. Pesticides are often organic chemical molecules and their repeated application to crops poses toxicity threats to both agricultural workers during handling and to the environment, due to spray drift, persistence in the soil or washing off into surface or ground water. It would be advantageous to be able to use alternative compounds that are less toxic to humans and the environment, but that at the same time provide effective control of plant pests. Proteinaceous pesticides with specificity against a certain plant pest target may be very advantageous in this respect, as they are expected to be short-lived in the environment and to have less toxic off-target effects. However, there are only a few proteinaceous or peptidergic pesticides known. Some examples are Bt toxins, lectins, defensins, fabatins, tachyplesin, magainin, harpin (see WO2010019442), pea albumin 1-subunit b (PA1b). However, these proteinaceous pesticides are either small peptides with compact structures, stabilized by several disulphide bridges, or are larger proteins (>300 amino acids) which occur in crystalline form (cry toxins). It is indeed known in the field of agriculture that biologicals, and in particular proteins, are challenging structures for developing pesticides, as they generally have far too little stability to maintain their pesticidal function in an agrochemical formulation, in particular for applications in the field. The current applicant has developed several proteinaceous pesticides based on heavy chain variable domain of a heavy chain antibody (VHH). For instance VHH binding to a glucosylceramide of a fungal pest were developed showing antifungal activity (WO 2014/177595, WO 2014/191146 and WO 2016/071438) and more recently a VHH interaction with a lipid fraction of fungal pests have shown the ability of VHH to cause retardation of growth of a spore and even lysis of a spore of a fungal pests such as the economically important fungal plant pests *Botrytis cinerea* (WO 2021/198396). However, there is still room for improvement. VHH molecules in agricultural and pharmaceutical settings need to perform even at high salt concentrations. It is known that high salt concentrations can impair the ability of an antibody to bind to its target due to the weakening electrostatic interactions and/or hydrogen bonds (Janeway C A Jr, Travers P, Walport M, et al. *Immunobiology: The Immune System in Health and Disease.* 5th edition. New York: Garland Science; 2001. *The interaction of the antibody molecule with specific antigen.* Available from: https://www.ncbi.nlm.nih.gov/books/NBK27160/). Additionally, salts and more specifically the divalent cations such as Ca2+ have been shown to have membrane stabilising effects (*EDTA-induced Membrane Fluidization and Destabilization: Biophysical Studies on Artificial Lipid Membranes Prachayasittikul Virapong Acta Biochimica et Biophysica Sinica*, 2007, Vol 39 (11), 901-913 DOI: 10.1111/j.1745-7270.2007.00350.x). Therefore where a proteinaceous pesticides disrupts membrane integrity such as the molecules in WO 2021/198396, the presence of increased salt concentrations has the potential to decrease the biological activity of such molecules. Alternatively or in addition, the interaction with the cell wall of microorganisms can be influenced by the presence of salts and said interaction could potentially inactivate or reduce the activity of proteinaceous pesticides at elevated salt concentrations by hampering their ability to destabilise the membrane (*The interaction with fungal cell wall polysaccharides determines the salt tolerance of antifungal plant defensins* Bleackley Mark R., Dawson Charlotte S., Payne Jennifer A. E., Harvey Peta J., Rosengren K. Johan, Quimbar Pedro, Garcia-Ceron Donovan, Lowe Rohan, Bulone Vincent, van der Weerden Nicole L., Craik David J., Anderson Marilyn A. *The Cell Surface,* 2019, Vol 5, 100026 DOI: 10.1016/j.tcsw.2019.100026 μMID: 32743142). In agricultural applications proteinaceous pesticides are present and applied in a formulated product comprising several different compounds of which many can be salts, in addition agricultural formulations are often mixed with water prior to application of the product on crops. The water used in agricultural settings is often water with a high ion content including Ca2+ cations. proteinaceous pesticides therefore commonly encounter elevated salt concentrations. In conclusion, there is a need for VHHs with increased salt tolerance towards their binding characteristics and activity.

SUMMARY OF THE INVENTION

The present inventors have successfully developed VHH antibodies binding to pests, in particular plant, animal or human pathogenic pests, such as but not limited to plant, animal or human pathogenic fungi. More specifically, the present inventors have developed VHH antibodies which bind to at least one fungal species and hereby causing retardation of the growth of said at least one fungal species or lysis of a spore of said at least one fungal species and wherein said effect is maintained at elevated salt concentrations.

The mere binding of the VHH antibody may be sufficient for the fungicidal activity through retardation of growth and/or lysis and explosion of spores, thus preventing mycelium formation. The VHH antibody may therefore have fungicidal or fungistatic activity.

Moreover, these VHH antibodies retain their integrity, stability and activity in a composition and that efficacious pest or pathogenic control can surprisingly be achieved by applying compositions, comprising the VHH antibodies as disclosed in the present application, to crops, animals or humans. In addition, these VHH antibodies retain their integrity, stability and activity in a composition with elevated salt concentrations.

The efficacy and potency of the VHH antibodies at elevated salt concentrations as disclosed herein suggests a potential for either a lower treatment dosage and/or a more effective treatment at the same dose. In addition the ability to maintain efficacy and potency at elevated salt levels suggest improved stability in environments with higher salt concentrations, such as often encountered in pharmaceutical and agricultural settings. This can imply a reduction of unwanted side-effects and reduced toxicity in both agrochemical and medical applications. Moreover, this allows the application of lower amounts or dosages of the VHH antibodies or compositions disclosed herein.

In particular, the present inventors have developed VHH antibodies that are capable of preventing, protecting, treating or curing a plant, animal or human from (developing) an infection by a pathogen or from any other biological interaction with a pathogen, in particular a fungal pathogen. Therefore, the present invention demonstrates that biological molecules, such as VHH antibodies, can be used to effectively protect or treat a plant, animal or human from being damaged in any way by or from suffering from a biological interaction between the plant, animal or human and a pathogen, such as for instance through infection by a pathogen. Moreover, the present invention demonstrates that the VHH antibodies as disclosed herein do so even at elevated salt concentrations.

The VHH antibodies and compositions of the present invention can be used as stand-alone products, e.g. stand-alone compositions, such as an anti-fungal composition.

The VHH antibodies and compositions of the present invention can be used in a preventative or prophylactic manner, i.e. the first application occurs prior to disease presence.

The VHH antibodies and compositions of the present invention can be used as contact fungicides.

According to the invention, there is thus provided a composition comprising at least one VHH antibody, which VHH antibody is capable of binding to at least one fungal species. The VHH antibody thereby causes retardation of growth of a spore of the said at least one fungal species and/or lysis of a spore of the said at least one fungal species. Whereby the VHH antibody causes retardation of growth of a spore of the at least one fungal species and/or lysis of a spore of the at least one fungal species in the presence of elevated salt concentrations. That is to say, binding of the VHH antibody to at least one fungal species results in retardation of growth of a spore of the said at least one fungal species and/or lysis of a spore of the said at least one fungal species and this effect is maintained at elevated salt concentrations.

There is also provided a VHH antibody, which VHH antibody binds to at least one fungal species. The VHH antibody thereby causes retardation of growth of a spore of the said fungus and/or lysis of a spore of the said fungus. Whereby the VHH antibody causes retardation of growth of a spore of the at least one fungal species and/or lysis of a spore of the at least one fungal species in the presence of elevated salt concentrations. That is to say, binding of the VHH antibody to the at least one fungal species results in retardation of growth of a spore of the said at least one fungal species and/or lysis of a spore of the said at least one fungal species and this effect is maintained at elevated salt concentrations.

Further, the invention provides a composition comprising at least one VHH antibody, which VHH antibody comprises the amino acid sequence set out in SEQ ID NO: 2, or an amino acid sequence having at least about 80% sequence identify thereto and which VHH antibody is capable of binding to at least one fungal species. The at least one VHH antibody as set out in SEQ ID NO:2, may be encoded by a polynucleotide as set out in SEQ ID NO: 1.

According to the invention, there is further provided a composition comprising at least one VHH antibody, which VHH antibody comprises:

a CDR1 region having the amino acid sequence set out in SEQ ID NO: 3, a CDR2 region having the amino acid sequence set out in SEQ ID NO: 4, and a CDR3 region having the amino acid sequence set out in SEQ ID NO: 5 and which VHH antibody is capable of binding to at least one fungal species.

The invention also provides:
a VHH antibody comprising the amino acid sequence set out in SEQ ID NO: 2, or an amino acid sequence having at least about 80% sequence identify thereto, wherein said VHH antibody is capable of binding to at least one fungal species; and
a polynucleotide as set out in SEQ ID NO: 1 encoding for the at least one VHH antibody as set out in SEQ ID NO: 2; and
a VHH antibody comprising a CDR1 region having the amino acid sequence set out in SEQ ID NO: 3, a CDR2 region having the amino acid sequence set out in SEQ ID NO: 4, and a CDR3 region having the amino acid sequence set out in SEQ ID NO: 5, where said VHH antibody is capable of binding to at least one fungal species.

The invention also provides a VHH antibody comprising or consisting of the amino acid sequence set out in SEQ ID NO: 2.

The invention also provides a VHH antibody having a CDR1 region comprising or consisting of the sequence set out in SEQ ID NO: 3, a CDR2 region comprising or consisting of the sequence set out in SEQ ID NO: 4, and a CDR3 region comprising or consisting of the sequence set out in SEQ ID NO: 5.

The invention also provides a VHH antibody comprising or consisting of the amino acid sequence set out in SEQ ID NO: 2, or an amino acid sequence having up to 1, up to 2, up to 3, up to 4 or up to 5 amino acid substitutions thereof.

Any of the VHH antibodies of the invention may be provided in a composition, for example an agrochemical composition.

A composition as disclosed herein may comprise at least one heavy chain variable domain of a heavy chain antibody (VHH), which is naturally devoid of light chains or a functional fragment thereof, such as but not limited to a heavy chain single variable domain of a camelid heavy chain antibody (camelid VHH) or a functional fragment thereof.

A composition as disclosed herein may comprise at least one camelized heavy chain variable domain of a conventional four-chain antibody (camelized VH), or a functional fragment thereof.

A composition as disclosed herein may comprise at least one heavy chain variable domain of an antibody or a functional fragment thereof, which does not have an amino acid sequence that is exactly the same as (i.e. as in a degree of sequence identity of 100% with) the amino acid sequence of a naturally occurring VH domain, such as the amino acid sequence of a naturally occurring VH domain from a mammal, and in particular from a human being.

It is understood that a VHH antibody as defined herein can be derived from an organism comprising a heavy chain single variable domain such as a camelid species (referred to as a VHH or sometimes known as nanobodies) or shark species (sometimes referred to as Immunoglobulin new antigen receptors or IgNARs). Additionally the VHH antibody as defined herein can be derived from a heavy chain of a conventional antibody. The skilled person will know that when obtaining a VHH antibody from a conventional antibody certain modification may have to be made to improve solubility and/or stability of the VH chain in absence of the VL light chain.

A composition as disclosed herein may be an agrochemical composition.

An agrochemical composition as disclosed herein may at least comprise a VHH antibody, capable of binding to a fungus.

The at least one VHH antibody in the agrochemical composition disclosed herein may be present in an amount effective to protect or treat a plant or a part of any thereof from an infection or other biological interaction with a fungal pathogen, such as for example but not limited to the concentration of the VHH antibody in the agrochemical composition ranging from 0.0001% to 50% by weight.

The at least one VHH antibody in the agrochemical compositions disclosed herein may be formulated in an aqueous solution, optionally but without limitation together with a suitable carrier and/or one or more suitable additive, such as an agrochemically suitable carrier and/or one or more suitable additive.

An agrochemical composition as disclosed herein may comprise at least one VHH antibody, which binds to at least one pathogenic fungus, i.e. at least one plant pathogenic fungus.

An agrochemical composition as disclosed herein may comprise at least one VHH antibody which specifically binds to at least one plant pathogenic fungus, such as but not limited to a plant pathogenic fungus of a genus chosen from the group comprising *Alternaria, Ascochyta, Botrytis, Cercospora, Colletotrichum, Diplodia, Erysiphe, Fusarium, Gleosporium, Leptosphaeria, Gaeumanomyces, Helminthosporium, Macrophomina, Nectria, Oidium, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus,* and *Aspergillus*.

An agrochemical composition as disclosed herein may comprise at least one VHH antibody which specifically binds to at least one plant pathogenic fungus, such as but not limited to a plant pathogenic fungus of a species chosen from the group comprising *Alternaria alternata, Alternaria aroborescens, Alternaria solani, Botrytis cinerea, Cercospora beticola Colletotrichum orbiculare, Colletotrichum gloeosporioides, Colletotrichum lindemuthianum, Colletotrichum coccodes, Colletotrichum musea, Colletotrichum fruticola, Fusarium graminearum, Fusarium culmorum, Fusarium oxysporum, Penicillium digitatum, Penicillium Italicum, Phakopsora pachvrhizi, Uncinula necator, Oidium neolycopersici, Podosphaera aphanis* and *Podosphaera xanthii*.

An agrochemical composition as disclosed herein may comprise at least one VHH antibody, which binds to at least one fungal species, which is a fungus for a plant chosen from the group comprising cereals, sorghum, rice, sugar beet, fodder beet, fruit, nuts, the plantain family or grapevines, leguminous crops, oil crops, cucurbits, fibre plants, fuel crops, vegetables, ornamentals, shrubs, broad-leaved trees, evergreens, grasses, coffee, tea, tobacco, hops, pepper, rubber and latex plants.

The at least one VHH antibody in the agrochemical composition disclosed herein, may comprise:

(SEQ ID NO: 2)
DVQLQESGGGLVQAGGSLRLSCAASRRTGTRYVMAWFRQAPGKEREFVAG

VDWSGSGQYYAESVKGRFTISKDNTRKTVYLQMNALKPEDTAVYYCAATR

RLSGRAYLWATASTYDYWGRGTQVTVSS;

or a sequence having at least about 80% sequence identity thereto and which VHH antibody is capable of binding to at least one fungal species.

The at least one VHH antibody in the agrochemical compositions disclosed herein may at least comprise the amino acid sequence of a CDR1 region having the sequence RRTGTRYVMAW (SEQ ID NO: 3), a CDR2 region having the sequence AGVDWSGSGQYYAESVKGR-(SEQ ID NO: 4), and a CDR3 region having the sequence TRRLSG-RAYLWATASTYDY (SEQ ID NO: 5) and which VHH antibody is capable of binding to at least one fungus.

The VHH antibodies disclosed herein are generally capable of binding to a fungus.

In a further aspect, the present invention provides compositions comprising at least one VHH antibody, which specifically binds to a fungus, for use as an anti-fungal agent. The present invention also provides the VHH antibodies, which specifically bind to a fungus, for use as an anti-fungal agent.

Accordingly, the invention provides a composition comprising at least one VHH antibody, which VHH antibody comprises:
  the amino acid sequence set out in SEQ ID NO: 2, or an amino acid sequence having at least about 80% sequence identify thereto and which VHH antibody is capable of binding to a fungus for use as an anti-fungal agent; or
  a CDR1 region comprising the amino acid sequence set out in SEQ ID NO: 3, a CDR2 region comprising the amino acid sequence set out in SEQ ID NO:4, and a CDR3 region comprising the amino acid sequence set out in SEQ ID NO: 5 and which VHH antibody is capable of binding to at least one fungal species. The invention furthermore provides a VHH antibody or a composition comprising a VHH antibody,
  wherein the VHH antibody comprises a CDR1 region comprising the amino acid sequence set out in SEQ ID NO: 3, a CDR2 region comprising the amino acid sequence set out in SEQ ID NO:4, and a CDR3 region comprising the amino acid sequence set out in SEQ ID NO: 5; and
  wherein the VHH antibody comprises the amino acid sequence set out in SEQ ID NO: 2, or an amino acid sequence having at least about 80% sequence identify thereto.

The invention also provides use of a composition or VHH antibody as disclosed herein as an anti-fungal agent. Such use may be as an anti-fungal agent on a plant. Accordingly, the present invention provides uses of agrochemical compositions comprising at least one VHH antibody, which specifically binds to at least one fungal species, as an anti-fungal agent on plants. More specifically, in the present invention the at least one VHH antibody is capable of binding to a fungus and acts as an anti-fungal agent on plants in the presence of elevated salt concentrations. In addition to the non-therapeutic use as an antifungal agent (e.g. on a plant), the present invention also provides the therapeutic use of the antibodies and compositions of the invention as an antifungal agent (e.g. to treat and/or prevent a fungal infection in an animal, such as a human).

In the invention, an antifungal agent may be a fungistatic agent and/or fungicidal agent.

The invention also provides nucleic acid sequences encoding any of the VHH antibody sequences disclosed herein. The nucleic acid sequences encoding the VHH antibody of the invention may be SEQ ID NO: 1. Alternatively, the nucleic acid sequence encoding the VHH antibody of the invention may be selected from the group of nucleic acid sequences according to SEQ ID NOs: 10 to 15. The present invention furthermore provides vectors comprising nucleic acids encoding a VHH of the invention. Further, the invention provides host cells comprising the nucleic acids and vectors disclosed herein.

Also, the present invention provides methods for protecting or treating a plant or a part of a plant from an infection with a plant pathogenic fungus, wherein the methods at least comprise the step of applying directly or indirectly to the plant or to a part of the plant, an agrochemical composition or VHH antibody as disclosed herein. The agrochemical composition or VHH antibody may be applied under conditions effective to protect or treat the plant or a part of the plant against infection with said plant pathogenic fungus. Therefore, in a particular embodiment, the present invention provides a method for treating a plant comprising (the step of) applying the agrochemical composition of VHH antibody of the invention to the plant.

These methods may comprise applying directly or indirectly to the plant or to a part of the plant a VHH antibody as disclosed herein, for example at an application rate of around 50 g of the VHH antibody per hectare, such as but not limited to an application rate of around 75 g of the VHH antibody per hectare, such as an application rate of around 100 g of the VHH antibody per hectare, or in particular an application rate of around 200 g of VHH antibody per hectare. In a preferred embodiment the application rate of the VHH antibody as disclosed herein is 100 g or lower, preferably 75 g or lower and in a most preferred embodiment the application rate of the VHH antibody as described herein is 50 g or lower.

These methods may comprise applying directly or indirectly to the plant or to a part of the plant a VHH antibody as disclosed herein, for example at an application rate between a preferred range of between 1 g and 100 g of the VHH antibody per hectare, such as but not limited to an application rate of between 1 g and 75 g of the VHH antibody per hectare, in particular and preferred embodiment an application rate of between 1 g and 50 g of the VHH antibody. It being understood that the VHH antibody when applied directly or indirectly to the plant or to a part of the plant, the VHH antibody may be contained in an agrochemical composition.

These methods may be part of an integrated pest management method for protection or treating a plant or part of said plant from an infection with a plant pathogenic fungus, at least comprising the step of applying directly or indirectly to said plant or to a part of said plant, a composition comprising at least one VHH antibody and one or more agrochemicals, under conditions effective to protect or treat said plant or a part of said plant against said infection with said plant pathogenic fungus.

The invention further relates to a mixture comprising at least one VHH antibody capable of binding a fungus and at least one agrochemical.

The agrochemical compositions or VHH antibody as disclosed herein may be directly or indirectly applied to the plant or to a part of the plant by spraying, atomizing, foaming, fogging, culturing in hydroculture, culturing in hydroponics, coating, submerging, and/or encrusting, optionally post-harvest.

The present invention also provides post-harvest treatment methods for protecting or treating a harvested plant or a harvested part of the plant from an infection with a plant pathogenic fungus, at least comprising the step of applying directly or indirectly to the harvested plant or to a harvested part of the plant, an agrochemical composition or VHH antibody as disclosed herein, under conditions effective to protect or treat the harvested plant or a harvested part of the plant against infection with the plant pathogenic fungus.

The present invention also provides methods of inhibiting the growth of a plant pathogenic fungus or methods of killing a plant pathogenic fungus, the methods comprising at least the step of applying directly or indirectly to a plant or to a part of the plant, an agrochemical composition or VHH antibody as disclosed herein.

In these methods, the agrochemical compositions or VHH antibody as disclosed herein may be directly or indirectly applied to the plant or to a part of the plant by spraying, atomizing, foaming, fogging, culturing in hydroculture, culturing in hydroponics, coating, submerging, and/or encrusting, optionally post-harvest.

The present invention also provides for a transgenic plant, plant part, seed or plant cell comprising a nucleic acid sequence encoding a VHH antibody as disclosed herein and where the VHH antibody is expressed in said transgenic plant, plant seed, seed or plant cell. By expressing the VHH antibody in a transgenic plant, plant part, seed or plant cell the VHH antibody may protect or treat the transgenic plant, plant part, seed or plant cell against infection with a plant pathogenic fungus.

Finally the present invention also provides a method for manufacturing a variant of the VHH antibody as disclosed herein. Where the variant of the VHH antibody binds to at least one fungal species thereby causes retardation of growth of a spore of the said at least one fungal species and/or lysis of a spore of the at least one fungal species. Whereby the variant of the VHH antibody causes retardation of growth of a spore of the at least one fungal species and/or lysis of a spore of the at least one fungal species in the presence of elevated salt concentrations. That is to say, binding of the variant of the VHH antibody to the at least one fungal species results in retardation of growth of a spore of the said at least one fungal species and/or lysis of a spore of the said at least one fungal species and this effect is maintained at elevated salt concentrations.

DESCRIPTION OF THE SEQUENCE LISTING

Figure 1:
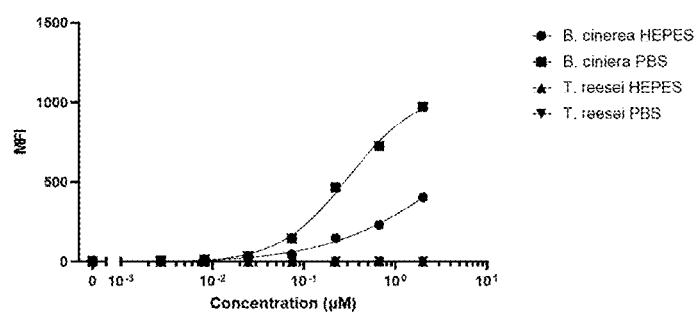
FIG. 1 Binding assay results showing VHH antibody 11A11 binding to *B. cinerea*, compared to absence of binding to an unrelated fungus *T. reesei*.

The sequence listing provides at least the following sequences of Table 2:

TABLE 1

| | Correlation between SEQ ID NOs and the VHH antibody sequences and CDR sequences | | | | | | | | |
|---|---|---|---|---|---|---|---|---|---|
| VHH | Full VHH nucleotide sequence (SEQ ID NO): | Full VHH amino acid sequence (SEQ ID NO): | CDR1 (SEQ ID NO): | CDR2 (SEQ ID NO): | CDR3 (SEQ ID NO): | FR1 (SEQ ID NO): | FR2 (SEQ ID NO): | FR3 (SEQ ID NO): | FR4 (SEQ ID NO): |
| 11A11 | 1 | 2 | 3 | 4 | 5 | 6 | 7 | 8 | 9 |

TABLE 2

| | | sequence listing |
|---|---|---|
| Name | SEQ ID NO: | Sequence |
| VHH nucl | 1 | GACGTACAGCTGCAGGAGTCTGGGGGAGGATTGGTGCAGGCTGGGGGC TCTCTGAGACTCTCCTGTGCTGCCTCTAGACGTACCGGCACTAGATATGT GATGGCCTGGTTCCGCCAGGCTCCAGGGAAGGAGCGTGAGTTTGTCGCA GGTGTTGACTGGAGTGGATCGGGTCAATACTATGCAGAGTCCGTGAAGG GCCGATTCACCATCTCCAAAGACAACACCAGGAAAACGGTGTATCTTCAG ATGAACGCCCTGAAACCTGAGGACACGGCCGTTTATTACTGTGCAGCAAC |

TABLE 2-continued sequence listing

| Name | SEQ ID NO: | Sequence |
|---|---|---|
| | | AAGGCGACTGTCCGGGCGTGCCTACTTGTGGGCCACTGCTTCGACGTAT GACTACTGGGGCCGGGGGACCCAGGTCACCGTCTCCTCA |
| VHH aa | 2 | DVQLQESGGGLVQAGGSLRLSCAASRRTGTRYVMAWFRQAPGKEREFVAG VDWSGSGQYYAESVKGRFTISKDNTRKTVYLQMNALKPEDTAVYYCAATRR LSGRAYLWATASTYDYWGRGTQVTVSS |
| VHH CDR1 | 3 | RRTGTRYVMAW |
| VHH CDR2 | 4 | AGVDWSGSGQYYAESVKGR |
| VHH CDR3 | 5 | TRRLSGRAYLWATASTYDY |
| VHH FR1 | 6 | DVQLQESGGGLVQAGGSLRLSCAAS |
| VHH FR2 | 7 | FRQAPGKEREFV |
| VHH FR3 | 8 | FTISKDNTRKTVYLQMNALKPEDTAVYYCAA |
| VHH FR4 | 9 | WGRGTQVTVSS |
| VHH nucl Pichia 1 | 10 | gacGTTCAACTACAGGAGTCTGGTGGCGGTCTTGTTCAAGCTGGAGGATC TCTTAGGCTTTCTTGTGCCGCATCCCGTAGGACTGGCACTAGATACGTGA TGGCATGGTTTAGGCAAGCTCCTGGTAAAGAAAGGGGAATTTGTCGCTGGA GTAGATTGGTCCGGCTCCGGCCAATACTACGCTGAGTCTGTGAAGGGTC GTTTCACTATCTCCAAGGATAATACTAGGAAAACGGTATACTTGCAAATGA ACGCTTTGAAACCTGAGGATACTGCAGTTTATTACTGCGCTGCAACCAGG AGGCTGTCTGGCAGAGCCTATCTGTGGGCTACAGCATCCACTTACGACTA TTGGGGAAGAGGTACTCAAGTGACCGTGTCCTCAtaa |
| VHH nucl Pichia 2 | 11 | gacGTTCAGTTGCAAGAATCTGGAGGAGGTTTGGTTCAAGCTGGTGGTTCT TTGAGATTGTCTTGTGCTGCTTCTAGAAGAACTGGTACAAGATACGTTATG GCTTGGTTCAGACAAGCTCCAGGTAAAGAAAGAGAGTTTGTTGCTGGAGT GGATTGGAGTGGTAGTGGTCAATACTACGCTGAATCTGTTAAGGGTAGAT TTACTATTTCTAAAGATAACACTAGAAAGACTGTTTACCTTCAAATGAATGC TTTGAAGCCTGAGGATACTGCCGTTTACTACTGTGCTGCTACTAGAAGATT GTCTGGAAGAGCTTATTTGTGGGCTACCGCCTCTACTTACGATTATTGGG GTAGAGGTACTCAAGTTACTGTCTCTTCTtaa |
| VHH nucl Pichia 3 | 12 | GACGTTCAACTCCAAGAGTCAGGTGGTGGTTTGGTTCAGGCTGGCGGAT CTTTTAAGGCTTTCTTGTGCAGCATCCAGACGTACAGGAACAGGTATGTG ATGGCCTGGTTCAGACAGGCTCCTGGTAAGGAACGTGAATTCGTTGCTG GAGTCGATTGGTCAGGTAGCGGTCAATACTACGCAGAATCGCTTAAGGGT CGATTTACGATCAGTAAAGATAACACTAGAAAAACCGTCTATTTGCAAATG AATGCTCTGAAACCAGAGGACACAGCTGTATACTACTGCGCAGCTACTAG ACGTTTGAGCGGTAGGGCATACCTATGGGCCACTGCTTCGACTTATGACT ATTGGGGTAGAGGAACACAAGTTACCGTGTCCTCTTAA |
| VHH nucl tricho 1 | 13 | gacGTCCAGCTCCAGGAGAGCGGCGGCGGCCTCGTCCAGGCTGGCGGCA GCCTCCGCCTCAGCTGCGCCGCCTCTCGCCGCACCGGCACGCGCTACG TCATGGCCTGGTTCCGACAGGCCCCTGGCAAGGAGCGCGAGTTCGTCGC CGGCGTCGACTGGTCCGGCAGCGGCCAGTACTACGCCGAGAGCGTCAA GGGCCGCTTCACCATCAGCAAGGACAACACCCGCAAGACCGTCTACCTC CAGATGAACGCCCTCAAGCCTGAGGACACCGCCGTCTACTACTGCGCCG CTACGCGCCGACTCAGCGGCCGAGCCTACCTCTGGGCCACCGCCAGCA CCTACGACTACTGGGGCCGAGGCACCCAGGTCACCGTCAGCAGCtaa |
| VHH nucl tricho 2 | 14 | GACGTCCAATTACAAGAGAGTGGCGGCGGATTGGTACAGGCTGGAGGAT CACTGAGACTATCGTGCGCAGCAAGCCGGCGAACCGGTACCCGATACGT GATGGCGTGGTTTAGACAGGCCCCGGGAAGGAAAGGGAATTCGTTGCC GGCGTTGACTGGTCTGGCTCCGGCCAGTACTATGCCGAGTCTGTCAAGG GTCGCTTCACCATCTCGAAGGATAACACGCGCAAGACCGTGTACCTCCAA ATGAACGCCCTTAAACCCGAGGACACTGCTGTCTACTACTGCGCCGCGA CGCGCCGTCTGAGCGGCCGCGCGTATCTCTGGGCTACGGCCTCCACTTA CGACTATTGGGGCCGGGGGACACAGGTCACAGTCAGCTCCTAA |
| VHH nucl bacillus 1 | 15 | GATGTCCAACTGCAAGAATCAGGCGGAGGCCTGGTTCAAGCAGGCGGAT CACTGAGACTGTCATGCGCAGCATCAAGAAGAACAGGCACAAGATATGTT ATGGCGTGGTTTAGACAAGCACCGGGAAAGAAAGAGAATTTGTTGCAGG CGTTGATTGGTCAGGCTCAGGCCAATATTACGCAGAATCAGTTAAAGGAC GCTTCACGATCAGCAAAGATAATACACGCAAAACAGTCTACCTGCAAATG AATGCACTGAAACCGGAAGATACAGCAGTCTATTATTGCGCAGCAACACG CAGACTGTCAGGCAGAGCATATCTGTGGGCAACAGCATCAACATATGATT ATTGGGGCAGAGGCACACAAGTTACAGTTTCATCATAA |

DETAILED DESCRIPTION OF THE INVENTION

Reference to any prior art in this specification is not, and should not be taken as, an acknowledgment or any form of suggestion that this prior art forms part of the common general knowledge in any country.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs.

The present invention will be described with respect to particular embodiments but the invention is not limited thereto but only by the claims. Any reference signs in the claims shall not be construed as limiting the scope.

Definitions

Where the term "comprising" is used in the present description and claims, it does not exclude other elements or steps.

Where an indefinite or definite article is used when referring to a singular noun e.g. "a" or "an", "the", this includes a plural of that noun unless something else is specifically stated.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, New York (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the terms "complementarity determining region" or "CDR" within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains. VHH antibodies lack the light chain canonical antibodies.

The term "affinity", as used herein, refers to the degree to which a polypeptide, in particular an immunoglobulin, such as an antibody, or an immunoglobulin fragment, such as a VHH antibody, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex.

The term "binding to a fungus" or "interacting with fungus" or "specifically binding to a fungus" as used herein interchangeably in the context of and antibody, such as a VHH antibody, means that the antibody is capable of binding to or interacting with a fungus, or part of a fungus. Said fungus is preferably a plant pathogenic fungus such as Botrytis cinerea to which the VHH antibody of the current invention were raised. Therefore, in a particular embodiment, the VHH antibody of the invention binds to Botrytis cinerea. However, binding to a fungus of the VHH antibody of the current invention is not limited to a specific fungal species. That is to say, cross-activity is possible where the VHH antibody of the current invention bind to a fungus that is not Botrytis cinerea. In a more preferred embodiment, binding to a fungus also leads to retardation of growth of a spore of said fungus or lysis of a spore of said fungus. In a more preferred embodiment retardation of growth of a spore of said fungus or lysis of a spore of said fungus occurs in the presence of elevated salt concentrations as further described herein. The VHH antibody of the current invention however does not bind to or interact with all fungal species, for example the VHH antibody of the current invention does not bind to the fungal species Trichoderma reesei. Therefore, the VHH antibody of the current invention may be characterised by the ability to bind to a plant pathogenic fungus as disclosed herein, as compared to the absence of binding to Trichoderma reesei, and were said assessment is made as provided in the binding assay of Example 4. More specifically, the VHH antibodies of the current invention may bind to the plant pathogenic fungi as disclosed herein at a concentration of between 10-1 and 1 µM or higher and where such a binding leads to a median fluorescent intensity (MFI) of above background levels and where said MFI increases with higher concentrations of the VHH antibody. Where the MFI value is the fluorescent signal emitted by the DY488 fluorophore conjugated to a monoclonal antibody binding to the C-terminal strep-tag that may be added to the VHH antibodies of the invention for this assay and as measured in the presence of PBS buffer. More specifically, the MFI value may be 10 or more, 20 or more, 50 or more, 100 or more, when binding to a plant pathogenic fungal species as described herein, whereas the MFI value of binding to Trichoderma reesei essential stays below or at the background level at concentration 10-1 and 1 µM.

The terms "inhibiting", "reducing" and/or "preventing" as used herein may refer to a VHH antibody as disclosed herein that binds to a fungus and inhibits, reduces and/or prevents a biological activity of said fungus, as measured using a suitable in vitro, cellular or in vivo assay, such as for example the assay given in Example 5. Accordingly, "inhibiting", "reducing" and/or "preventing" may also refer to inhibiting, reducing and/or preventing one or more biological or physiological mechanisms, effects, responses, functions pathways or activities of the fungus.

Thus, more particularly, "inhibiting", "reducing" and/or "preventing" using VHH antibody as disclosed herein may mean either inhibiting, reducing and/or preventing the normal physiological or biological mechanisms, effects, responses, functions, pathways or activities in which the fungus is involved, such as by at least 10%, but preferably at least 20%, for example by at least 50%, at least 60%, at least 70%, at least 80%, at least 90%, at least 95% or more, as measured using a suitable in vitro, cellular or in vivo assay, such as the assay in Example 5, compared to the same assay under the same conditions but without using the VHH antibody as disclosed herein.

The inhibiting or antagonizing activity or the enhancing or agonizing activity of a VHH antibody as disclosed herein may be reversible or irreversible, but for agrochemical, pharmaceutical and pharmacological applications will typically occur reversibly.

A VHH antibody as disclosed herein is considered to be "(in) essentially isolated (form)" as used herein, when it has been extracted or purified from the host cell and/or medium in which it is produced.

In some aspects the amino acid sequence as disclosed herein are the amino acid sequences of a VHH antibody comprising 3 CDR domains and 4 framework FR regions. In a more specific aspect the amino acid sequence of a VHH antibody as described herein comprises or consists of the amino acid sequence set out in SEQ ID NO: 2, or a sequence having at least 70%, at least 75%, at least 80%, at least 85%, at least 90%, at least 95% or at least 98% identity thereto. In another aspect, the present invention provides an amino acid sequence of a VHH antibody comprising:

a CDR1 region comprising or consisting of the sequence set out in SEQ ID NO: 3;
a CDR2 region comprising or consisting of the sequence set out in SEQ ID NO: 4; and
a CDR3 region comprising or consisting of the sequence set out in SEQ ID NO: 5.

The amino acid sequence of a VHH antibody defined herein may suitably have certain framework region sequences. For example, the amino acid sequence of a VHH antibody defined herein may comprise a framework region 1 (FR1) sequence comprising or consisting of the sequence set out in SEQ ID NO: 6, a framework region 2 (FR2) sequence comprising or consisting of the sequence set out in SEQ ID NO: 7, a framework region 3 (FR3) sequence comprising or consisting of the sequence set out in SEQ ID NO: 8, and a framework region 4 (FR4) sequence comprising or consisting of the sequence set out in SEQ ID NO: 9.

"Plant" as used herein, means an entire plant or a part thereof, including fresh fruit, vegetables and seeds. The plant or plant part may be a live plant or part thereof. Also, the term "plant" as used herein encompasses whole plants, ancestors and progeny of the plants and plant parts, including seeds, shoots, stems, leaves, roots (including tubers), flowers, and tissues and organs. In some aspects, each of the aforementioned plant or plant parts may comprise the polynucleotide of the invention encoding a VHH antibody. The term "plant" also encompasses plant cells, suspension cultures, callus tissue, embryos, meristematic regions, gametophytes, sporophytes, pollen and microspores, again wherein each of the aforementioned may comprise the gene/nucleic acid of interest.

"Crop" as used herein means a plant species or variety that is grown to be harvested as food, livestock fodder, fuel raw material, or for any other economic purpose. As a non-limiting example, said crops can be maize, cereals, such as wheat, rye, barley and oats, sorghum, rice, sugar beet and fodder beet, fruit, such as pome fruit (e.g. apples and pears), citrus fruit (e.g. oranges, lemons, limes, grapefruit, or mandarins), stone fruit (e. g. peaches, nectarines or plums), nuts (e.g. almonds or walnuts), soft fruit (e.g. cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fibre plants, such as cotton, flax or hemp, fuel crops, such as sugarcane, *miscanthus* or switchgrass, vegetables, such as potatoes, tomatoes, peppers, lettuce, spinach, onions, carrots, egg-plants, asparagus or cabbage, ornamentals, such as flowers (e.g. petunias, pelargoniums, roses, tulips, lilies, or chrysanthemums), shrubs, broad-leaved trees (e.g. poplars or willows) and evergreens (e.g. conifers), grasses, such as lawn, turf or forage grass or other useful plants, such as coffee, tea, tobacco, hops, pepper, rubber or latex plants.

In a preferred embodiment, the agrochemical compositions or VHH antibodies of the current invention may be used to treat pathogenic fungal infections on pepper plants.

In another preferred embodiment, the agrochemical compositions of VHH antibodies of the current invention may be used to treat pathogenic fungal infection on cucurbits.

In another preferred embodiment, the agrochemical compositions of VHH antibodies of the current invention may be used to treat pathogenic fungal infection on grapes.

In another preferred embodiment, the agrochemical compositions of VHH antibodies of the current invention may be used to treat pathogenic fungal infection on strawberries.

A "field" or "plant field" refers to an agricultural area where plants are cultivated. The field may be any piece of land designated for the purpose of growing plants, such as the plants and crops disclosed herein. The field may also be a piece of land covered by a greenhouse. The field may also refer to an area where the plants and crops may be cultured in elevated structures comprising the plants and crops disclosed herein i.e. the plants and crops may not be growing directly on the piece of land but rather in elevated structures comprising soil or water. For example the field may comprise plants and crops grown in a hydroponics setup. The field may, but must not, comprise growing plants, that is to say that the field may be an empty field, as the invention can also be applied for pre-treating a field before sowing or plant growing. In a preferred embodiment, however, the field is a field comprising living plants.

A "pest", as used here, is an organism that is harmful to plants, animals, humans or human concerns, and includes, but is not limited to crop pests (as later defined), household pests, such as cockroaches, ants, etc., and disease vectors, such as malaria mosquitoes.

A "plant pest", "plant pathogen" or "crop pest", as used in the application interchangeably, refers to organisms that specifically cause damage to plants, plant parts or plant products, particularly plants, plant parts or plant products, used in agriculture. Note that the term "plant pest" or "crop pest" is used in the meaning that the pest targets and harms plants. preferably the "plant pest", "crop pest" or "plant pathogen" is a plant pathogenic fungus.

"Fungus", as used herein, means a eukaryotic organism, belonging to the group of Eumycota. The term fungus in the present invention also includes fungal-like organisms such as the Oomycota.

Oomycota (or oomycetes) form a distinct phylogenetic lineage of fungus-like eukaryotic microorganisms.

This group was originally classified among the fungi but modern insights support a relatively close relationship with the photosynthetic organisms such as brown algae and diatoms, within the group of heterokonts.

Examples of "plant pathogenic fungi" or a "plant pathogenic fungus" as used herein, are known in the art and include, but are not limited to, those selected from the group consisting of the Genera: *Alternaria; Ascochyta; Botrytis; Cercospora; Colletotrichum; Diplodia; Erysiphe; Fusarium; Leptosphaeria; Gaeumanomyces; Helminthosporium; Macrophomina; Nectria; Oidium, Peronospora; Phakopsora; Phoma; Phymatotrichum; Phytophthora; Plasmopara; Podosphaera; Puccinia; Puthium; Pyrenophora; Pyricularia; Pythium; Rhizoctonia; Scerotium; Sclerotinia; Septoria; Thielaviopsis; Uncinula; Venturia*; and *Verticillium*. Specific examples of plant fungi infections which may be combated with the agrochemical compositions or VHH antibodies of the invention include, powdery mildew and *Botrytis cinerea* in fruit and vegetable crops such as grapes and strawberries. Additional specific examples of plant fungi infections which may be combated with the agrochemical compositions of the invention include *Erysiphe graminis* in cereals, *Erysiphe cichoracearum* and *Sphaerotheca fuliginea* in cucurbits, *Podosphaera leucotricha* in apples, *Podosphaera aphanis*, for example to treat powdery mildew, for example on strawberry, *Podosphaera xanthii*, for example to treat powdery mildew, for example on cucumber, *Oidium neolycopersici*, for example to treat powdery mildew, for example on tomatoes, *Uncinula necator* in vines, *Puccinia* sp. In cereals, *Rhizoctonia* sp. In cotton, potatoes, rice and lawns, *Ustilago* sp. In cereals and sugarcane, *Venturia inaequalis* (scab) in apples, *Helminthosporium* sp. In cereals, *Septoria nodorum* in wheat, *Septoria tritici* in wheat, *Rhynchosporium secalis* on barley, *Botrytis cinerea* (gray mold) in strawberries, tomatoes and grapes, *Cercospora arachidicola* in groundnuts, *Peronospora tabacina* in tobacco, or other *Peronospora* in various crops, *Pseudocercosporella herpotrichoides* in wheat and barley, *Pyrenophera teres* in barley, *Pyricularia oryzae* in rice, *Phytophthora infestans* in potatoes and tomatoes, *Fusarium* sp. (such as *Fusarium oxysporum*) and *Verticillium* sp. In various plants, Plasmopara viticola in grapes, *Alternaria* sp. In fruit and vegetables, *Pseudoperonospora cubensis* in cucumbers, *Mycosphaerella fijiensis* in banana, *Ascochyta* sp. In chickpeas, *Leptosphaeria* sp. On canola, *Phakopsora* spp., such as *Phakopsora pachyrhizi*, and *Colleotrichum* sp. In various crops, for example *Colletotrichum orbiculare* which may cause anthracnose in squash or *Colletotrichum gloeosporioides* causing anthracnose in peppers. The compositions according to the invention are active against normally sensitive and resistant species and against all or some stages in the life cycle of the plant pathogenic fungus.

In particular embodiments, the agrochemical compositions or VHH antibodies as disclosed herein bind a plant pathogenic fungus from the genus chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Oidium, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakopsora, Monilinia, Mucor, Rhizopus*, and *Aspergillus*.

In a more preferred embodiment, the agrochemical compositions or VHH antibodies as disclosed herein bind a plant pathogenic fungus from the genus chosen from the group comprising *Botrytis, Colletotrichum, Phakopsora, Uncinula, Oidium* and *Podosphaera*.

In a more preferred embodiment, the agrochemical compositions or VHH antibodies as disclosed herein are directed against a plant pathogenic fungus according to the species chosen from the group comprising *Alternaria alternata, Alternaria aroborescens, Alternaria solani, Botrytis cinerea, Cercospora beticola, Colletotrichum orbiculare, Colletotrichum gloeosporioides, Colletotrichum lindemuthianum, Colletotrichum coccodes, Colletotrichum musea, Colletotrichum fruticola, Fusarium graminearum, Fusarium culmorum, Fusarium oxysporum, Penicillium digitatum, Penicillium Italicum, Phakopsora pachvrhizi, Uncinula necator, Oidium neolycopersici, Podosphaera aphanis* and *Podosphaera xanthii*.

In a preferred embodiment, the agrochemical compositions or VHH antibodies as disclosed herein are directed against a plant pathogenic fungus *Botrytis cinerea*.

In a preferred embodiment, the agrochemical compositions or VHH antibodies as disclosed herein are directed against a plant pathogenic fungus *Colletotrichum gloeosporioides*. In another preferred embodiment, the agrochemical compositions or VHH antibodies as disclosed herein are directed against a plant pathogenic fungus *Podosphaera xanthii*.

"Pest infection" or "pest disease" as used herein refers to any inflammatory condition, disease or disorder in a living organism, such as a plant, animal or human, which is caused by a pest.

"Fungal infection" or "fungal disease" as used herein refers to any inflammatory condition, disease or disorder in a living organism, such as a plant, animal or human, which is caused by a fungus.

"Active substance", "active ingredient" or "active principle", as used interchangeably herein, means any biological, biochemical or chemical element and its derivatives, fragments or compounds based thereon, including microorganisms, having general or specific action against harmful organisms on a subject, and in particular on plants, parts of plants or on plant products, as they occur naturally or by manufacture, including any impurity inevitably resulting from the manufacturing process.

"Agrochemical", as used herein, means suitable for use in the agrochemical industry (including agriculture, horticulture, floriculture and home and garden uses, but also products intended for non-crop related uses such as public health/pest control operator uses to control undesirable insects and rodents, household uses, such as household fungicides and insecticides and agents, for protecting plants or parts of plants, crops, bulbs, tubers, fruits (e.g. from harmful organisms, diseases or pests); for controlling, preferably promoting or increasing, the growth of plants; and/or for promoting the yield of plants, crops or the parts of plants that are harvested (e.g. its fruits, flowers, seeds etc.). Examples of such substances will be clear to the skilled person and may for example include compounds that are active as insecticides (e.g. contact insecticides or systemic insecticides, including insecticides for household use), herbicides (e.g. contact herbicides or systemic herbicides, including herbicides for household use), fungicides (e.g. contact fungicides or systemic fungicides, including fungicides for household use), nematicides (e.g. contact nematicides or systemic nematicides, including nematicides for household use) and other pesticides or biocides (for example agents for killing insects or snails); as well as fertilizers; growth regulators such as plant hormones; micro-nutrients, safeners, pheromones; repellants; insect baits; and/or active principles that are used to modulate (i.e. increase, decrease, inhibit, enhance and/or trigger) gene expression (and/or other biological or biochemical processes) in or by the targeted plant (e.g. the plant to be protected or the plant to be controlled), such as nucleic acids (e.g., single stranded or double stranded RNA, as for example used in the context of RNAi technology) and other factors, proteins, chemicals, etc. known per se for this purpose, etc. Examples of such agrochemicals will be clear to the skilled person; and for example include, without limitation: glyphosate, paraquat, metolachlor, acetochlor, mesotrione, 2,4-D,atrazine, glufosinate, sulfosate, fenoxaprop, pendimethalin, picloram, trifluralin, bromoxynil, captan, clodinafop, Dithiocarbamate, fluroxypyr, phenylpyrroles (such as fludioxonil), hydroxyanilides (such as fenhexamid), dicarboximides (such as iprodione), kresoxim-methyl, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, fluopyram, indoxacarb, bifenthrin, tefluthrin, azoxystrobin, thiamethoxam, tebuconazole, mancozeb, morpholine, cyazofamid, fluazinam, Myclobutanil, pyraclostrobin, epoxiconazole, chlorothalonil, strobilurin, triazole, vinclozolin, copper fungicides (for example copper oxychloride, copper hydroxide), anilinopyrimidines (e.g., cyprodinil, pyrimethanil, mepanipyrim), trifloxystrobin, prothioconazole, difenoconazole, carbendazim, propiconazole, thiophanate, sulphur, boscalid, tricyclazole, hexaconazole, metalaxyl, benomyl, benzimidazole, kitazin, tridemorph, propineb, streptomycin sulfate, and oxytetracycline and other known agrochemicals or any suitable combination(s) thereof.

Further examples of agrochemicals are biological substances, such as a microbials, for example a *Pseudomonas* strain such as *Pseudomonas chlororaphis* (ma342), *Pseudomonas* sp. strain dsmz 13134; or a *Bacillus* strain such as *Bacillus thuringiensis* ssp. *aizawai* Abts-1857, *Bacillus thuringiensis* ssp. *aizawai* Gc-91, *Bacillus thuringiensis* ssp. *kurstaki* 10113p/B, *Bacillus thuringiensis* ssp. *kurstaki* Sa-11 10473p/B, *Bacillus thuringiensis* ssp. *kurstaki* Strain EG 2348, *Bacillus thuringiensis* ssp. *israeliensis* (Serotype H-14) Strain AM65-52, *Bacillus amyloliquefaciens* subsp. *plantarum* D747, *Bacillus amyloliquefaciens* MBI 600, *Bacillus amyloliquefaciens* strain FZB24, *Bacillus amyloliquefaciens* strain qst 713, *Bacillus firmus* 1-1582; or a *Streptomyces* strain such as *Streptomyces* strain K61; or a *Trichoderma* strain such as *Trichoderma harzianum* T-22, *Trichoderma asperellum* strain T34, *Trichoderma atroviride* strain SC1; or a *Coniothyrium* strain such as *Coniothyrium minitans*, an *Isaria* strain such as *Isaria fumosorosea* var. apopka strain 97; or a *Pythium* strain such as *Pythium oligandrum* M1; or a *Clonostachys* strain such as *Clonostachys rosea* J1446; or a *Paecilomyces* strain such as *Paecilomyces fumosoroseus* FE9901; or a *Metarhizium* strain such as *Metarhizium brunneum* strain MA 43; or a *Beauveria* strain such as *Beauveria bassiana* ATCC 74040, *Beauveria bassiana* strain GHA; or a *Aureobasidium* strain such as *Aureobasidium pullulans* strain DSM14940 or DSM14941; or a *Ampelomyces* strain such as *Ampelomyces quisqualis* strain AQ10; or a *Saccharomyces* strain such as *Saccharomyces cerevisiae* LASO2; or a *Candida* strain such as *Candida oleophila* strain O; or an *Alamthomyce* strain such as *Akanthomyce muscarius* strain VE6. The microbial can also be a virus such as Granulose virus 8615p/b, Granulose virus 9198p/b, Granulose virus 10147p/b Granulose virus 10521p/b Granulose virus 11196g/b, pepino mosaic virus or a tomato mosaic virus.

Further examples of agrochemicals are biological substances may be bioactive proteins such as a small peptide with anti-microbial properties such as an antimicrobial peptide (AMP). AMPs usually have a length of in the range of 10 to 50 amino acids. AMPs are commonly anionic or cationic and can be subdivided in 4 classes: (i) anionic peptides which are rich in glutamic and aspartic acids, (ii) linear cationic α-helical peptides, (iii) cationic peptides enriched for specific amino acidrich in proline, arginine, phenylalanine, glycine, tryptophan and (iv) anionic/cationic peptides forming disulfide bonds. More specific examples are plant derived AMPs with antimicrobial or antiviral activities such as peptides composed of at least two helical domains connected by a linker/turn such as plant-derived amphipathic helix or two helices engineered into a helix-turn-helix (HTH) format in which homologous or heterogeneous helices are connected by a peptide linker. For example, as described in WO2021202476, WO2020072535, WO2020176224 or WO2003000863. Other examples of bioactive proteins are Bt toxins, e.g., a Cry protein, a Cyt protein, or a Vip protein, or an 6-endotoxin (e.g., Crystal (Cry) toxins and/or cytolytic (Cyt) toxins); vegetative insecticidal proteins (Vips); secreted insecticidal protein (Sips); or Bin-like toxins. "Vip" or "VIP" or "Vegetative Insecticidal Proteins" refer to proteins discovered from screening the supernatant of vegetatively grown strains of Bt for possible insecticidal activity. Vips have little or no similarity to Cry proteins. Of particular use and preference for use with this document are what have been called VIP3 or Vip3 proteins, which have Lepidopteran activity. Vips are thought to have a similar mode of action as Bt cry peptides. Further examples may be polypeptides derived from spider venom such as venom from funnel-web spiders such as agatoxins or diguetoxins more specifically a Mu-diguetoxin-dc1a variant polypeptides or a U1-agatoxin-Ta1b variant polypeptide. Other examples are polypeptides derived from sea anemone, such as Av3 toxins. Such as described in WO2022067214 or WO2021216621 or WO2022212777.

An "agrochemical composition" as used herein means a composition for agrochemical use, as further defined, comprising at least one active substance, optionally with one or more additives favouring optimal dispersion, atomization, deposition, leaf wetting, distribution, retention and/or uptake of agrochemicals. It will become clear from the further description herein that an agrochemical composition as used herein includes biological control agents or biological pesticides (including but not limited to biological biocidal, biostatic, fungistatic and fungicidal agents) and these terms will be interchangeably used in the present application. Accordingly, an agrochemical composition as used herein includes compositions comprising at least one biological molecule as an active ingredient, substance or principle for controlling pests in plants or in other agro-related settings (such for example in soil). Non-limiting examples of biological molecules being used as active principles in the agrochemical compositions disclosed herein are proteins (including antibodies and fragments thereof, such as but not limited to heavy chain variable domain fragments of antibodies, including VHH's), nucleic acid sequences, (poly-)saccharides, lipids, vitamins, hormones glycolipids, sterols, and glycerolipids.

As a non-limiting example, the additives in the agrochemical compositions disclosed herein may include but are not limited to diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents.

A "fungistatic composition" or a "fungistatic agent" as used herein means any active ingredient, substance or principle or a composition comprising any active ingredient, substance or principle for fungistatic use (as further defined herein) comprising at least one active fungistatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungicidal composition" or a "fungicidal agent" as used herein means any active ingredient, substance or principle or a composition comprising any active ingredient, substance or principle for fungicidal use (as further defined herein) comprising at least one active fungicidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

"Agrochemical use", as used herein, not only includes the use of agrochemicals as defined above (for example, pesticides, growth regulators, nutrients/fertilizers, repellants, defoliants etc.) that are suitable and/or intended for use in field grown crops (e.g., agriculture), but also includes the use of agrochemicals as defined above (for example, pesticides, growth regulators, nutrients/fertilizers, repellants, defoliants etc.) that are meant for use in greenhouse grown crops (e.g. horticulture/floriculture) or hydroponic culture systems and even the use of agrochemicals as defined above that are suitable and/or intended for non-crop uses such as uses in private gardens, household uses (for example, herbicides or insecticides for household use), or uses by pest control operators (for example, weed control etc.).

"Fungistatic (effect)" or "Fungistatic use", as used herein, includes any effect or use of an active substance (optionally comprised in a fungicidal or fungistatic composition as defined herein) for controlling, modulating or interfering with the harmful activity of a fungus, including but not limited to inhibiting the growth or activity of the fungus, altering the behavior of the fungus, and repelling the fungus in or on plants, plant parts or in other agro-related settings, such as for example for household uses or in soil.

"Fungicidal activity", as used herein, means to interfere with the harmful activity of a fungus, including but not limited to killing the fungus.

"Fungistatic activity", as used herein, means to interfere with the harmful activity of a fungus, including but not limited to inhibiting the growth or activity of the fungus, altering the behaviour of the fungus, and repelling the fungus.

"Fungicidal (effect)" or "Fungicidal use" or "fungicidal activity", as used herein, includes any effect or use of an active substance (optionally comprised in a fungicidal composition as defined herein) for killing the fungus in or on plants, plant parts or in other agro-related settings, such as for example for household uses or in soil.

An anti-fungal agent may be any type of protein, VHH antibody or agrochemical having an intrinsic fungicidal or fungistatic activity.

A "carrier", as used herein, means any solid, semi-solid or liquid carrier in or on(to) which an active substance can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, buckyballs, water droplets that are part of an water-in-oil emulsion, oil droplets that are part of an oil-in-water emulsion, organic materials such as cork, wood or other plant-derived materials (e.g. in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof.

As used herein, the term "antibody" refers to polyclonal antibodies, monoclonal antibodies, humanized antibodies, single-chain antibodies, and fragments thereof such as Fab F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F ab)2, Fv, and others that retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

"Heavy chain variable domain of an antibody or a functional fragment thereof", as used herein, means (i) the variable domain of the heavy chain of a heavy chain antibody, which is naturally devoid of light chains (also indicated hereafter as VHH), including but not limited to the variable domain of the heavy chain of heavy chain antibodies of camelids or sharks or (ii) the variable domain of the heavy chain of a conventional four-chain antibody (also indicated hereafter as VH), including but not limited to a camelized (as further defined herein) variable domain of the heavy chain of a conventional four-chain antibody (also indicated hereafter as camelized VH).

As further described hereinbelow, the amino acid sequence and structure of a heavy chain variable domain of an antibody can be considered, without however being limited thereto, to be comprised of four framework regions or "FR's", which are referred to in the art and hereinbelow as "framework region 1" or "FR1"; as "framework region 2" or "FR2"; as "framework region 3" or "FR3"; and as "framework region 4" or "FR4", respectively, which framework regions are interrupted by three complementary determining regions or "CDR's", which are referred to in the art as "complementarity determining region 1" or "CDR1"; as "complementarity determining region 2" or "CDR2"; and as "complementarity determining region 3" or "CDR3", respectively.

As also further described hereinbelow, the total number of amino acid residues in a heavy chain variable domain of an antibody (including a VHH or a VH) can be in the region of 110-130. It should however be noted that parts, fragments or analogs of a heavy chain variable domain of an antibody are not particularly limited as to their length and/or size, as long as such parts, fragments or analogs retain (at least part of) the functional activity, such as the pesticidal, biocidal, biostatic activity, fungicidal or fungistatic activity (as defined herein) and/or retain (at least part of) the binding specificity of the original a heavy chain variable domain of an antibody from which these parts, fragments or analogs are derived from. Parts, fragments or analogs retaining (at least part of) the functional activity, such as the pesticidal, biocidal, biostatic activity, fungicidal or fungistatic activity (as defined herein) and/or retaining (at least part of) the binding specificity of the original heavy chain variable domain of an antibody from which these parts, fragments or analogs are derived from are also further referred to herein as "functional fragments" of a heavy chain variable domain.

A method for numbering the amino acid residues of heavy chain variable domains is the method described by Chothia et al. (Nature 342, 877-883 (1989)), the so-called "AbM definition" and the so-called "contact definition". Herein, this is the numbering system adopted.

Figure 2:
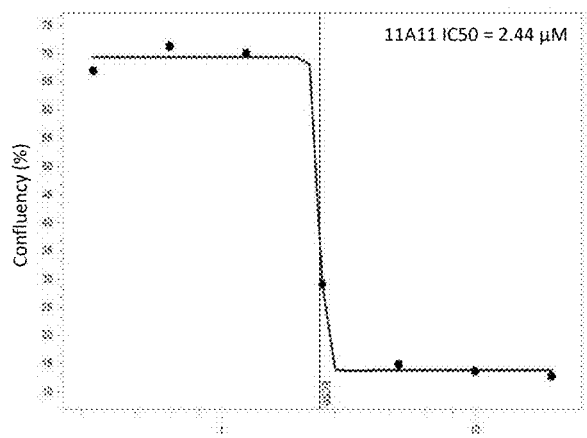
FIG. 2 Dose response curve of an antifungal assay showing growth inhibition effect of VHH antibody 11A11 on *Botrytis cinerea*
Figure 3:
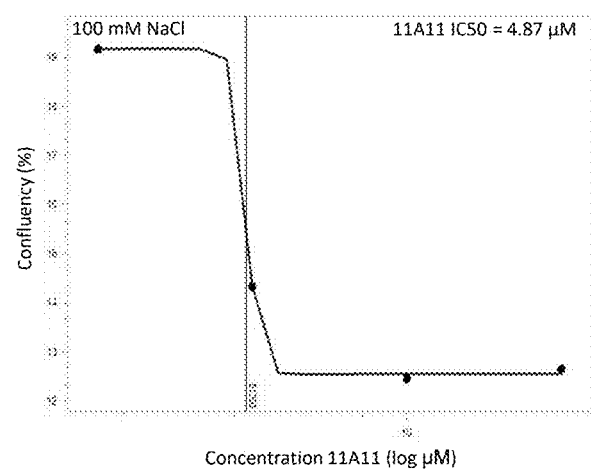
FIG. 3 Dose response curve of an antifungal assay showing growth inhibition effect of VHH antibody 11A11 on *Botrytis cinerea* in the presence of NaCl at a concentration of 100 mM.
Figure 4:
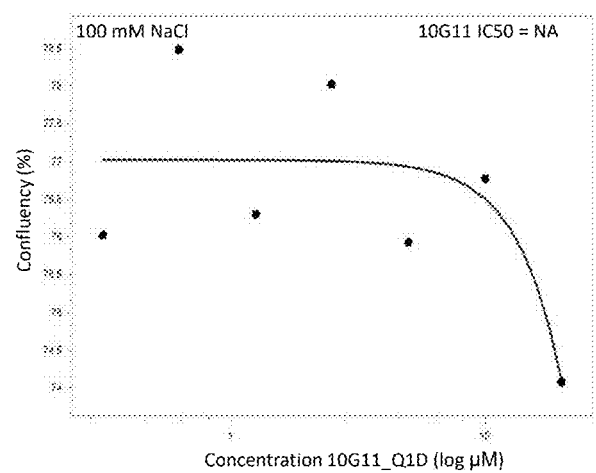
FIG. 4 Dose response curve of an antifungal assay showing the absence of growth inhibition effect of VHH 10G11_Q1D on *Botrytis cinerea* in the presence of NaCl at a concentration of 100 mM.
Figure 5:
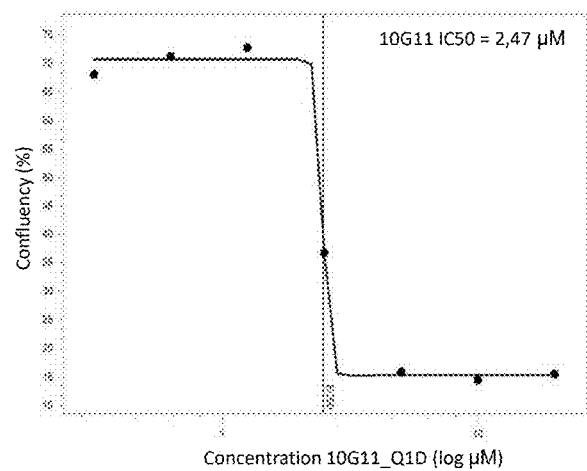
FIG. 5 Dose response curve of an antifungal assay showing growth inhibition effect of VHH antibody 10G11_Q1D on *Botrytis cinerea*
Figure 6:
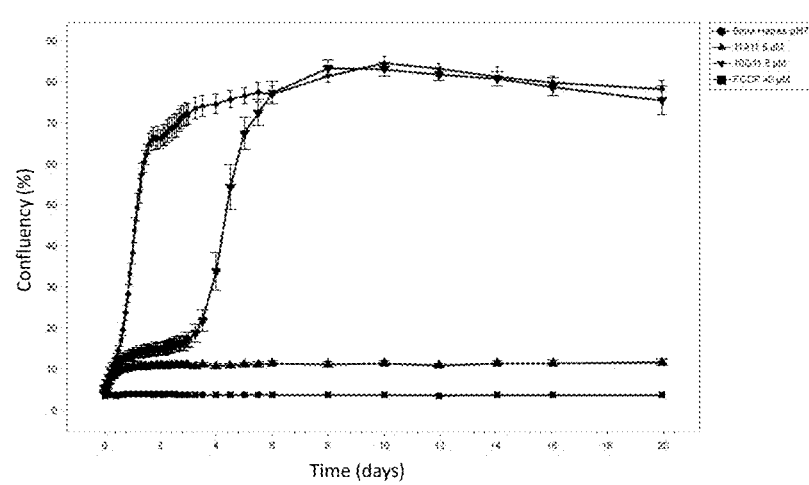
FIG. 6 Antifungal assay over time shows the continued growth inhibiting effect of VHH antibody 11A11 on *Botrytis cinerea*
Figure 7:
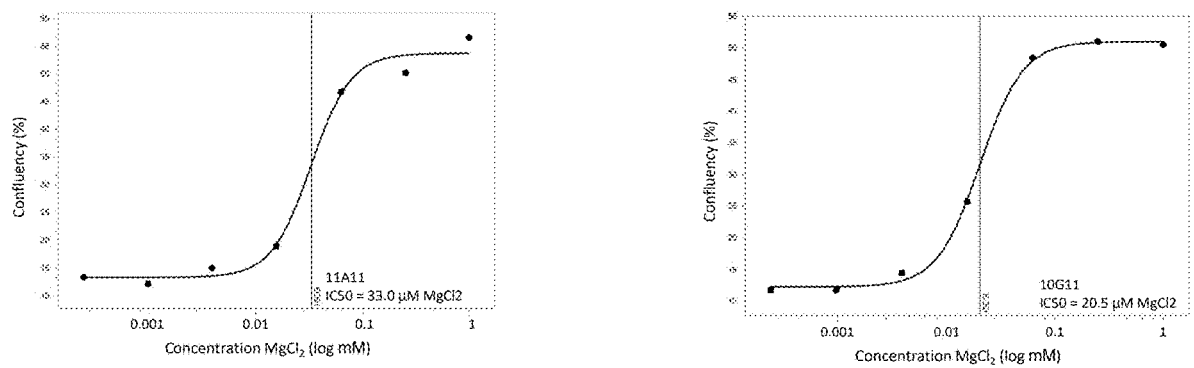
FIG. 7 Dose response curve of an antifungal assay showing influence of increasing concentrations of MgCl2 on the inhibition effect of VHH antibody 11A11 (left panel) and 10G11_Q1D (right panel) on *Botrytis cinerea*.

Alternatively, the amino acid residues of a variable domain of a heavy chain variable domain of an antibody (including a VHH or a VH) may be numbered according to the general numbering for heavy chain variable domains given by Kabat et al. ("Sequence of proteins of immunological interest", US Public Health Services, NIH Bethesda, Md., Publication No. 91), as applied to VHH domains from Camelids in the article of Riechmann and Muyldermans, referred to above (see for example FIG. 2 of said reference).

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx NV; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx; Hamers-Casterman et al., Nature 1993 Jun. 3; 363 (6428): 446-8.

Generally, it should be noted that the term "heavy chain variable domain" as used herein in its broadest sense is not limited to a specific biological source or to a specific method of preparation. For example, as will be discussed in more detail below, the heavy chain variable domains of the invention can be obtained (1) by isolating the VHH domain of a naturally occurring heavy chain antibody; (2) by isolating the VH domain of a naturally occurring four-chain antibody (3) by expression of a nucleotide sequence encoding a naturally occurring VHH domain; (4) by expression of a nucleotide sequence encoding a naturally occurring VH domain (5) by "camelization" (as described below) of a naturally occurring VH domain from any animal species, in particular a species of mammal, such as from a human being, or by expression of a nucleic acid encoding such a camelized VH domain; (6) by "camelisation" of a "domain antibody" or "Dab" as described by Ward et al (supra), or by expression of a nucleic acid encoding such a camelized VH domain (7) using synthetic or semi-synthetic techniques for preparing proteins, polypeptides or other amino acid sequences; (8) by preparing a nucleic acid encoding a VHH or a VH using techniques for nucleic acid synthesis, followed by expression of the nucleic acid thus obtained; and/or (9) by any combination of the foregoing. Suitable methods and techniques for performing the foregoing will be clear to the skilled person based on the disclosure herein and for example include the methods and techniques described in more detail hereinbelow.

However, according to a specific embodiment, the heavy chain variable domains as disclosed herein do not have an amino acid sequence that is exactly the same as (i.e. as a degree of sequence identity of 100% with) the amino acid sequence of a naturally occurring VH domain, such as the amino acid sequence of a naturally occurring VH domain from a mammal, and in particular from a human being.

The terms "effective amount" and "effective dose", as used herein, mean the amount needed to achieve the desired result or results.

As used herein, the terms "determining", "measuring", "assessing", "monitoring" and "assaying" are used interchangeably and include both quantitative and qualitative determinations.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

VHH Antibodies

The VHH antibodies disclosed here are generally capable of binding to at least one fungus. The VHH antibody thereby causes retardation of growth of a spore of the said at least one fungus and/or lysis of a spore of the said at least one fungus. That is to say, binding of the VHH antibody to a fungus results in retardation of growth of a spore of the said at least one fungus and/or lysis of a spore of the said at least one fungus. Therefore, in a particular embodiment, the VHH antibody of the invention causes retardation of growth of a spore of the said at least one fungus. In another particular embodiment, the VHH antibody of the invention causes lysis of a spore of the said at least one fungus.

The VHH antibodies of and used in the invention may (specifically) bind to at least one fungal species. That is to say, the VHH antibodies of the invention were selected to bind to a fungal antigen. That is to say, the VHH antibodies of the invention were screened for their ability to bind to a fungal antigen or fungal target. Screening of such VHH antibodies may be done by displaying the VHH antibodies in for example phage display or yeast display or other similar technologies in the art which allows to select the VHH antibodies that bind to a certain fungal antigen.

The fungal antigen or fungal target used in a selection such as a phage selection or a binding assay such as an ELISA as described above may be a plant fungal antigen or a plant fungal target, such as but not limited to a fungal antigen or a fungal target. More specifically, the fungal antigen or fungal target used in a selection such as a phage selection or a binding assay such as an ELISA as described above, may be an antigen taken from the plant pathogenic fungus as described herein. The antigen may comprise a specific protein, lipid or lipid fraction purified from said fungal species. Alternatively the antigen may comprise a mixture of proteins and or lipids. In some cases homogenized fungal material is used where the homogenized material is derived from fungal mycelium, spores, sporulation spores or a mixture thereof. Most specifically the antigen used in a selection, such as a phage selection, or binding assay such as an ELISA, to obtain the VHH antibodies of the invention is a homogenized mixture derived from sporulation *Botrytis cinerea* spores.

The VHH antibody of and used in the invention may (specifically) bind to a fungal antigen or fungal target causing retardation of growth of a spore of the fungus and/or lysis of a spore of the fungus. The VHH antibodies of the invention may cause retardation of growth of a spore of the fungus and/or lysis of a spore of the fungus at elevated salt concentrations. That is to say, in an assay as described herein (such as an antifungal assay described in Example 5) to assess the ability of the VHH antibodies to cause retardation of growth of a spore of the fungus and/or lysis of a spore of the fungus, salt concentrations may be increased to a concentration that is higher than the salt concentrations employed in a standard assay where no extra salt is added (such as the assay performed in WO 2021/198396).

An "IC50 value", "EC50", "IC50", "EC50" or "half maximal inhibitory concentration" as used herein interchangeably is a measure for the potency of a tested VHH antibody in inhibiting the growth of a fungal pathogen. In practice (also see example 5) the growth of a fungal pathogen is tracked by measuring the confluency of said fungal pathogen in for example a well of a 96-well plate in the presence of a series of different concentrations of the tested VHH antibody. The confluency data at the time-point at which the non-treated or negative control reaches 90% saturation is then taken for each VHH antibody concentration. Said confluence values are then plotted against the log transformed concentration values yielding a sigmoidal curve. This sigmoid curve may serve to define an IC50 value. Where this IC50 is the concentration of VHH antibody where the corresponding confluence value is 50% of the saturated value as estimated by the maximum of the sigmoidal function.

More specifically, the IC50 may be the IC50 for inhibition of spore germination and/or mycelial growth (i.e. the concentration (μM) that inhibits 50% of spore germination and/or mycelial growth) for example of *Fusarium oxysporum* and/or *Botrytis cinerea*. In some embodiments, the VHH antibody have an IC50 of less than about 20 μM in the presence of 100 mM of NaCl, more preferably an IC50 of less than about 15 μM in the presence of 100 mM of NaCl, more preferably an IC50 of less than about 10 μM in the presence of 100 mM of NaCl, more preferably an IC50 of less than about 5 μM in the presence of 100 mM of NaCl. In a most preferred embodiment, the VHH antibody have an IC50 of about 5 μM in the presence of 100 mM of NaCl.

In some embodiments, the VHH antibody have an IC50 of less than about 5 μM in the absence of 100 mM NaCl, in a more preferred embodiment the VHH antibody have an IC50 of less than about 4 μM in the absence of 100 mM NaCl, in a more preferred embodiment the VHH antibody have an IC50 of less than about 3 μM in the absence of 100 mM NaCl, in an even more preferred embodiment the VHH antibody have an IC50 of less than about 2 μM in the absence of 100 mM NaCl. In a most preferred embodiment the VHH antibody have an IC50 of 2 μM in the absence of 100 mM NaCl. And where the IC50 values reflect the concentration needed for 50% inhibition of spore germination and/or mycelial growth, as performed in an assay according to Example 5. The prior art molecule 10G11_Q1D of PCT publication WO 2021/198396, shows no measurable IC50 value at a concentration of 100 μM of NaCl, for inhibition of spore germination and/or mycelial growth, as performed in an assay according to Example 5, whereas without NaCl the IC50 value of 10G11_Q1D when performed according to the assay in Example 5 is between 2 and 3 μM.

Therefore, the term "elevated salt concentration" in the context of NaCl, may be defined as a concentration of NaCl where the VHH antibody of the invention retains its capacity of causing retardation of growth of a spore of at least one fungal species and/or lysis of a spore of at least one fungal species as compared to VHH antibody not embodied by the current invention, such as 10G11_Q1D of PCT publication WO 2021/198396. More specifically, the concentration of NaCl considered as elevated may be 100 mM or higher.

In addition the prior art VHH antibody 10G11_Q1D of PCT publication WO 2021/198396 lacks the ability to repress spore outgrowth in an antifungal assay as described in Examples 5 and 6 for prolonged periods of time of for example 3 or more days. In some embodiments the VHH antibody of the invention are capable of suppressing spore outgrowth in an antifungal assay for 4 days or more, more preferable 5 days or more, even more preferably 6 days or more, even more preferably 7 days or more, even more preferably 8 days or more, even more preferably 9 days or more, even more preferably 10 days or more, even more preferably 12 days or more, even more preferably 14 days or more, even more preferably 16 days or more, even more preferably 18 days or more, even more preferably 20 days or more, when performed in an assay as described in Examples 5 and 6.

Alternatively, the ability of the VHH antibody of the current invention to cause retardation of growth of a spore of at least one fungal species and/or lysis of a spore of the at least one fungal species, may be assessed by increasing the concentration of MgCl2 salt in the assay media to set it against the molecules of the prior art.

The inventors have here provided VHH antibodies that bind to at least one fungal species, hereby causing retardation of growth of a spore of the at least one fungal species and/or lysis of a spore of the at least one fungal species and have screened for and/or selected for the ability of said VHH antibodies to retain their activity at elevated concentrations of MgCl2. The present invention provides VHH antibodies that bind to at least one fungal species, hereby causing retardation of growth of a spore of the at least one fungal species and/or lysis of a spore of the at least one fungal species and whereby said retardation of growth of a spore of the at least one fungal species or lysis of a spore of the at least one fungal species occurs at MgCl2 concentrations that are higher compared to the activity of a VHH antibody not screened for and/or selected for its ability to retain activity at elevated MgCl2 concentrations. More specifically, in some aspects the VHH antibodies of the current invention retain 50% of their activity at a MgCl2 concentration that is 1.5 times higher than the prior art molecules not screened and/or selected to have activity at elevated MgCl2 concentrations, in some aspects 1.8 times higher, in some aspects 2 times higher, in some aspects 2.5 times higher, in some aspects 3 times higher, in some aspects 3.5 times higher, in some aspects 4 times higher, and even in some aspects 5 times higher, when assessing the activity in an antifungal assay, such as the set-up as described in Examples 5 and 8, and when comparing to the activity of a VHH antibody that was not screened or selected to have activity at elevated MgCl2 concentrations. In a preferred embodiment, the VHH antibodies of the current invention retain at least 50% of their activity at a MgCl2 concentration that is at least 2 times higher than the prior art molecules not screened and/or selected to have activity at elevated MgCl2 concentrations. For assessing the above, the prior art molecule is preferably 10G11_Q1D of PCT publication WO 2021/198396.

In a specific aspect, the VHH antibody of this invention retains at least 50% of its ability to cause retardation of growth of a spore of the fungus and/or lysis of a spore of the fungus at a MgCl2 concentration of 20 µM or higher, in an even more preferred aspect, the VHH antibody of this invention retains at least 50% of its ability to cause retardation of growth of a spore of the fungus and/or lysis of a spore of the fungus at a MgCl2 concentration of 30 µM or higher, even more preferred at 40 µM or higher, even more preferred 50 µM or higher, when assessing the activity in an antifungal assay, such as the set-up as described in Examples 5 and 7 and as compared to the condition where no MgCl2 is added. In a most preferred embodiment, the VHH antibody of this invention retains at least 50% of its ability to cause retardation of growth of a spore of the fungus and/or lysis of a spore of the fungus at a MgCl2 concentration of around 33 µM, when assessing the activity in an antifungal assay, such as the set-up as described in Examples 5 and 7, and as compared to the condition where no MgCl2 is added.

Put differently, the VHH antibody of this invention loses 50% of its ability to cause retardation of growth of a spore of the fungus and/or lysis of a spore of the fungus at a MgCl2 concentration of between 15 µM and 65 µM MgCl2 compared to the condition where no MgCl2 is added and when assessed according to the assay in Examples 5 and 8. More specifically the estimated concentration at which 50% of the activity of the VHH antibody of the invention is lost compared to the condition where no MgCl2 is added is between 20 µM and 50 µM MgCl2, even more specifically between 25 µM and 40 µM MgCl2. In the most specific aspect the VHH antibody of this invention loses 50% of its ability to cause retardation of growth of a spore of the fungus and/or lysis of a spore of the fungus at a MgCl2 concentration of 33 µM when assessing the activity in an antifungal assay, such as the set-up as described in Example 5 and as compared to the condition where no MgCl2 is added. Whereas the VHH antibody of the prior art such as 10G11_Q1D of PCT publication WO 2021/198396, loses 50% of its ability to cause retardation of growth of a spore of the fungus and/or lysis of a spore of the fungus at a MgCl2 concentration of between 15 µM and 25 µM MgCl2, when assessing the activity in an antifungal assay, such as the set-up as described in Examples 5 and 7 and as compared to the condition where no MgCl2 is added. More specifically the estimated concentration at which 50% of the activity of the VHH antibody of the prior art 10G11_Q1D is lost compared to the condition where no MgCl2 is added is 20 µM MgCl2 when assessing the activity in an antifungal assay, such as the set-up as described in Examples 5 and 7.

In some aspects the VHH antibodies of the current invention bind to at least one fungal species, hereby causing retardation of growth of a spore of the at least one fungal species and/or lysis of a spore of the at least one fungal species and whereby said retardation or lysis is unchanged in the presence of a MgCl2 concentration of 4 µM MgCl2, 5 µM MgCl2, 6 µM MgCl2, 7 µM MgCl2, 8 µM MgCl2, 9 µM MgCl2, 10 µM MgCl2, 11 µM MgCl2, 12 µM MgCl2, 13 µM MgCl2, 14 µM MgCl2, 15 µM MgCl2 or even 16 µM MgCl2, when assessing the activity in an antifungal assay, such as the set-up as described in Examples 5 and 7.

Therefore, the term "elevated salt concentration" in the context of MgCl2, may be defined as a concentration of MgCl2 where the VHH antibody of the invention retains its capacity of causing retardation of growth of a spore of at least one fungal species and/or lysis of a spore of at least one fungal species as compared to VHH antibody not embodied by the current invention, such as 10G11_Q1D of PCT publication WO 2021/198396. More specifically, the concentration of MgCl2 considered as elevated may be 10 µM or higher, preferably 20 µM or higher.

The inventors have here provided VHH antibodies that bind to at least one fungal species, hereby causing retardation of growth of a spore of the at least one fungal species and/or lysis of a spore of the at least one fungal species and have screened for and/or selected for the ability of said VHH antibodies to retain their activity at elevated concentrations of CaCl2. The present invention provides VHH antibodies that bind to at least one fungal species, hereby causing retardation of growth of a spore of the at least one fungal species and/or lysis of a spore of the at least one fungal species and whereby said retardation of growth of a spore of the at least one fungal species or lysis of a spore of the at least one fungal species occurs at CaCl2 concentrations that are higher compared to the activity of a VHH antibody not screened for and/or selected for its ability to retain activity at elevated CaCl2 concentrations. More specifically, in some aspects the VHH antibodies of the current invention retain 50% of their activity at a CaCl2 concentration that is 1.5 times higher than the prior art molecules not screened and/or selected to have activity at elevated CaCl2 concentrations, in some aspects 1.8 times higher, in some aspects 2 times higher, in some aspects 2.5 times higher, in some aspects 3 times higher, in some aspects 3.5 times higher, in some aspects 4 times higher, and even in some aspects 5 times higher, when assessing the activity in an antifungal assay, such as the set-up as described in Examples 5 and 8, and when comparing to the activity of a VHH antibody that was not screened or selected to have activity at elevated CaCl2 concentrations. In a preferred embodiment, the VHH antibodies of the current invention retain at least 50% of their activity at a CaCl2 concentration that is 2 times higher than the prior art molecules not screened and/or selected to have activity at elevated CaCl2 concentrations. For assessing the above, the prior art molecule is preferably 10G11_Q1D of PCT publication WO 2021/198396. In a specific aspect, the VHH antibody of this invention retains at least 50% of its ability to cause retardation of growth of a spore of the fungus and/or lysis of a spore of the fungus at a CaCl2 concentration of 250 µM or higher, in an even more preferred aspect, the VHH antibody of this invention retains at least 50% of its ability to cause retardation of growth of a spore of the fungus and/or lysis of a spore of the fungus at a CaCl2 concentration of 350 µM or higher, even more preferred at 450 µM or higher, when assessing the activity in an antifungal assay, such as the set-up as described in Examples 5 and 8, and as compared to the condition where no CaCl2 is added. In a most preferred embodiment, the VHH antibody of this invention retains at least 50% of its ability to cause retardation of growth of a spore of the fungus and/or lysis of a spore of the fungus at a CaCl2 concentration of around 300 µM, when assessing the activity in an antifungal assay, such as the set-up as described in Examples 5 and 8 and as compared to the condition where no CaCl2 is added.

Put differently, the VHH antibody of this invention loses 50% of its ability to cause retardation of growth of a spore of the fungus and/or lysis of a spore of the fungus at a CaCl2 concentration of between 200 µM and 1000 µM CaCl2 compared to the condition where no CaCl2 is added and when assessed according to the assay in Examples 5 and 8. More specifically the estimated concentration at which 50% of the activity of the VHH antibody of the invention is lost compared to the condition where no CaCl2 is added is between 250 µM and 500 µM CaCl2, even more specifically between 250 µM and 350 µM CaCl2. In the most specific aspect the VHH antibody of this invention loses 50% of its ability to cause retardation of growth of a spore of the fungus and/or lysis of a spore of the fungus at a CaCl2 concentration of 308 µM when assessing the activity in an antifungal assay, such as the set-up as described in Examples 5 and 8 and as compared to the condition where no CaCl2 is added. Whereas the VHH antibody of the prior art such as 10G11_Q1D of PCT publication WO 2021/198396, loses 50% of its ability to cause retardation of growth of a spore of the fungus and/or lysis of a spore of the fungus at a CaCl2 concentration of between 100 µM and 200 µM CaCl2, when assessing the activity in an antifungal assay, such as the set-up as described in Example 5 and as compared to the condition where no MgCl2 is added. More specifically the estimated concentration at which 50% of the activity of the VHH antibody of the prior art is lost compared to the condition where no CaCl2 is added is 152 µM CaCl2 when assessing the activity in an antifungal assay, such as the set-up as described in Examples 5 and 8.

In some aspects the VHH antibodies of the current invention bind to at least one fungal species, hereby causing retardation of growth of a spore of the at least one fungal species and/or lysis of a spore of the at least one fungal species and whereby said retardation or lysis is unchanged in the presence of a CaCl2 concentration of 10 µM CaCl2, 20 µM CaCl2, 30 µM CaCl2, 40 µM CaCl2, 50 µM CaCl2, 60 µM CaCl2, 70 µM CaCl2, 80 µM CaCl2, 90 µM CaCl2, 100 µM CaCl2, 110 µM CaCl2, 120 µM CaCl2, when assessing the activity in an antifungal assay, such as the set-up as described in Examples 5 and 8.

Therefore, the term "elevated salt concentration" in the context of CaCl2, may be defined as a concentration of CaCl2 where the VHH antibody of the invention retains its capacity of causing retardation of growth of a spore of at least one fungal species and/or lysis of a spore of at least one fungal species as compared to VHH antibody not embodied by the current invention, such as 10G11_Q1D of PCT publication WO 2021/198396. More specifically, the concentration of CaCl2 considered as elevated may be 100 µM or higher, more preferably 150 µM or higher.

The plant pathogenic fungus used in the assay such as an antifungal assay may be a plant pathogenic fungus as described herein. Preferably the plant pathogenic fungus used in the antifungal assay is a Botrytis species, even more preferably Botrytis cinerea.

In some aspects, the present invention provides a VHH antibody comprising or consisting of the amino acid sequence set out in SEQ ID NO: 2, or a sequence having at least 70%, at least 75%, at least 80%, at least 85%, at least 90%, at least 95% or at least 98% identity thereto.

In another aspect, the present invention provides a VHH antibody comprising:
  a CDR1 region comprising or consisting of the sequence set out in SEQ ID NO: 3;
  a CDR2 region comprising or consisting of the sequence set out in SEQ ID NO: 4; and
  a CDR3 region comprising or consisting of the sequence set out in SEQ ID NO: 5.

The VHH antibodies defined herein may suitably have certain framework region sequences. For example, the VHH antibody may comprise a framework region 1 (FR1) sequence comprising or consisting of the sequence set out in SEQ ID NO: 6, a framework region 2 (FR2) sequence comprising or consisting of the sequence set out in SEQ ID NO: 7, a framework region 3 (FR3) sequence comprising or consisting of the sequence set out in SEQ ID NO: 8, and a framework region 4 (FR4) sequence comprising or consisting of the sequence set out in SEQ ID NO: 9.

In some embodiments, for example those relating to any VHH antibodies of or derived from the clone referred to herein as 11A11, including any VHH antibodies having any specified sequence identity thereto or any substitutions therefrom, may comprise a framework region 1 (FR1) sequence comprising or consisting of the sequence set out in SEQ ID NO: 6, a framework region 2 (FR2) sequence comprising or consisting of the sequence set out in SEQ ID NO: 7, a framework region 3 (FR3) sequence comprising or consisting of the sequence set out in SEQ ID NO: 8, and a framework region 4 (FR4) sequence comprising or consisting of the sequence set out in SEQ ID NO: 9.

In some aspects, the invention provides a VHH antibody
  wherein the VHH antibody comprises a CDR1 region comprising or consisting of the sequence set out in SEQ ID NO: 3; a CDR2 region comprising or consisting of the sequence set out in SEQ ID NO: 4;
  and a CDR3 region comprising or consisting of the sequence set out in SEQ ID NO: 5; and
  wherein the VHH antibody comprises or consists of the amino acid sequence set out in SEQ ID NO: 2, or a sequence having at least 70%, at least 75%, at least 80%, at least 85%, preferably at least 90%, more preferably at least 95% or most preferably at least 98% identity thereto.

The CDR and framework regions maybe defined according to the Kabat numbering system.

In some embodiments, the VHH antibody may be from 80 to 200 residues in length. In another specific embodiment the VHH antibody has N- or C-terminal extensions.

In some embodiments the VHH antibody are derived from a precursor polypeptide consisting of a cleavable leader peptide fused to the N-terminus of the VHH antibody. Such a cleavable leader may be required for the successful production and/or secretion of the VHH antibody from a host cell. A cleavable leader often consists of a pre region and a pro region. The pre region is sometimes referred to as the signal peptide whereas the pro region is sometimes referred to as a "carrier peptide" (not to be confused with a carrier in the concept of a composition, more specifically an agrochemical composition). Often the cleavable leader exists of a pre and pro region. However in some cases the pro region may be missing and thus the cleavable leader solely exists of a pre region. In some cases the cleavable leader may be chosen depending on the species of host cell used for the production of the VHH antibody. In some embodiments where the host cell is a *Komagataella* host cell such as *Komagataella phaffii* (aka *Pichia pastoris*), the cleavable leader is the pre-pro peptide from a-mating factor (aMF) from *Saccharomyces cerevisiae*. Additional cleavable leaders can be found in for example WO2012152823 identified as SEQ ID NOs: 1 to 46. In some embodiments, where the host cell is a filamentous fungal host cell, such as a *Trichoderma reesei* or an *Aspergiullus niger* host cell, the cleavable leader peptide at the N-terminus may consist of only the signal peptide or signal sequence of, but not limited to glucoamylase Gla peptide, a cellobiohydrolase Cbh1 peptide or a cellobiohydrolase cbh2 peptide. In some embodiments, where the host cell is a filamentous fungal host cell, the N-terminus may contain a signal peptide and a carrier peptide. Carrier peptides may be, but are not limited to, a glucoamylase Gla peptide, a cellobiohydrolase Cbh1 peptide or a cellobiohydrolase cbh2 peptide. Carrier peptides may consist of a functional fragment of, but not limited to, glucoamylase Gla peptide, a cellobiohydrolase Cbh1 peptide or a cellobiohydrolase cbh2 peptide. A functional fragment of a carrier peptide may be limited to the N-terminal region of, but not limited to, glucoamylase Gla peptide, a cellobiohydrolase Cbh1 peptide or a cellobiohydrolase cbh2 peptide. Alternatively the functional fragment of a carrier peptide may be limited to the catalytic domain of the carrier peptide, such as the catalytic domain of the cbh1 carrier peptide. The N-terminal region may consist of only the signal peptide or signal sequence of, but not limited to glucoamylase Gla peptide, a cellobiohydrolase Cbh1 peptide or a cellobiohydrolase cbh2 peptide.

In some embodiments, where the host cell is a bacterial host cell, such as a *Bacillus* host cell for such as a *Bacillus subtilis* or a *Bacillus licheniformis* host cell, the cleavable leader peptide at the N-terminus may consist of only the signal peptide such as but not limited to the amyS signal peptide, the yvcE signal peptide, the yoqM signal peptide, the yuaB signal peptide, the pel signal peptide the yoaW signal peptide, the yqxi signal peptide, the pelB signal peptide, the lipA signal peptide, the lipB signal peptide, the yoqH signal peptide, the sacB signal peptide, the ybfO signal peptide, the bglS signal peptide, the yddT signal peptide or the yobB signal peptide. Other suitable cleavable leader peptides, where the host cell is a bacterial host cell, such as a *Bacillus* host cell for such as a *Bacillus subtilis* or a *Bacillus licheniformis* host cell may be found in Systematic Screening of Optimal Signal Peptides for Secretory Production of Heterologous Proteins in *Bacillus subtilis*. Gang Fu; Jinlan Liu; Jinshan Li; Beiwei Zhu; D. Journal of Agricultural and Food Chemistry, 2018. DOI: 10.1021/acs.jafc.8b04183 Or Optimization of Protease Secretion in *Bacillus subtilis* and *Bacillus licheniformis* by Screening of Homologous and Heterologous Signal Peptides. Christian Degering; Thorsten Eggert; Michael Puls; Applied and Environmental Microbiology, 2010, Vol 76 (19), 6370-6376.DOI: 10.1128/aem.01146-10.

In some cases, the VHH antibody comprises a N or C-terminal extension that can be used for purification or detection of the protein of interest, such as a His6, c-myc, FLAG, C-tag, 3×FLAG, His5, His10, HA, T7, strep, HSV, and/or an E-tag. In some cases the N-terminal extension that can be used for purification or detection of the protein of interest, such as a His6, c-myc, FLAG, C-tag, 3×FLAG, His5, His10, HA, T7, strep, HSV, and/or an E-tag is located between the cleavable leader and the VHH antibody.

In some cases, the cleavage of the leader peptide from the precursor polypeptide is incomplete, i.e. a smaller fragment or the entire cleavable leader remains attached the VHH antibody. Therefore, the N terminus can be extended by 1, 2, 3, 4, 5 or more amino acids derived from the leader. In some aspects the leader peptide will be complete i.e. the N-terminal extension is the length of the original cleavable leader of the precursor polypeptide. Where a smaller fragment or the entire cleavable leader remains attached to the VHH antibody, the VHH antibody of the invention will still bind to at least one fungal pest and will still cause retardation of growth of a spore of the at least one fungal species and/or lysis of a spore of the at least one fungal species.

The VHH antibodies of the invention may be provided in the form of compositions, for example agrochemical compositions.

Compositions Comprising at Least One VHH Antibody

In one aspect, the present inventors have provided compositions, particularly agrochemical compositions, comprising at least one antibody of the invention. In particular at least one VHH antibody which can bind to at least one fungal species. Importantly, through this interaction with, or a specific part of, the at least one fungal species, the compositions disclosed herein are capable of inhibiting, preventing or reducing one or more biological activities of the plant pathogen, such that the growth of the plant pathogen is inhibited, prevented or reduced. In certain embodiments, the agrochemical compositions as disclosed herein are capable of killing a plant pest through the specific interaction of at least one VHH antibody, which can specifically bind to a pest and which is comprised in the compositions.

Furthermore, the compositions comprising at least one VHH antibody as disclosed herein have several additional advantages over the traditional immunoglobulin and non-immunoglobulin binding agents known in the art. Indeed, in certain embodiments, the amino acid sequences of a VHH antibody as disclosed herein are isolated heavy chain immunoglobulin variable domains, which are more potent and more stable than conventional four-chain antibodies, leading to (1) lower dosage forms, less frequent dosage and thus less side effects; and (2) improved stability resulting in a broader choice of administration routes. Because of their small size, heavy chain immunoglobulin variable domains have the ability to cross membranes and penetrate into physiological compartments, tissues and organs not accessible to other, larger compounds and proteins.

In particular embodiments, the invention provides an agrochemical composition or a biological pesticide composition for combating plant pests, more particularly a plant fungus, which composition comprises at least one VHH antibody.

In certain further embodiments, the invention provides an agrochemical composition for combating plant pests, which composition comprises at least two (different) VHH antibodies as the active substance.

In still further embodiments, the invention provides an agrochemical composition for combating plant pests, which composition comprises at least three (different) VHH antibodies as the active substance. Additional combinations of different VHH antibodies with other polypeptides are also envisaged.

The agrochemical composition according to the invention is an agrochemical composition, as defined herein, for combating plant pathogenic fungi, as defined before, meaning that the agrochemical composition, more in particular the active substance, as defined before, comprised in the agrochemical composition, is able to interfere with, preferably to reduce or to arrest, the harmful effects of one or more plant pathogenic fungi on one or more plants, preferably crops.

In a broad embodiment the invention relates to a polypeptide that can bind to at least one fungus and hereby cause retardation of growth of a spore of the at least one fungal species and/or lysis of a spore of the at least one fungal species. In some embodiments these polypeptides are comprised in a composition, more specifically an agrochemical composition.

Binding of a VHH antibody to a at least one fungal species can be determined in any suitable manner known per se, including, for example biopanning, Scatchard analysis and/or competitive binding assays, such as radioimmunoassays (RIA), enzyme immunoassays (EIA) and sandwich competition assays, such as ELISA assays (for example as described in Example 4), and the different variants thereof known in the art.

In further particular embodiments, the compositions as disclosed herein at least comprise a VHH antibody which:
  comprises a CDR1 region having the sequence set out in SEQ ID NO: 3, a CDR2 region having the sequence set out in SEQ ID NO: 4, and a CDR3 region having the sequence set out in SEQ ID NO: 5 (and which is capable of binding to a fungus); or
  comprises the amino acid sequence set out in SEQ ID NO: 2 or an amino acid sequence having at least about 80% sequence identify thereto (and which VHH antibody is capable of binding to a fungus).

In particular embodiments, the at least one VHH antibody in the compositions as disclosed herein are heavy chain variable domains that comprises, consist or essentially consist of four framework regions (FR1 to FR4 respectively) and three complementarity determining regions (CDR1 to CDR3 respectively); or any suitable fragment of such an heavy chain variable domain (which will then usually contain at least some of the amino acid residues that form at least one of the CDRs, as further described herein). The sequences of the framework regions may be variable, or they may be specified.

The VHH antibody of the compositions disclosed herein may in particular be a domain antibody (or an heavy chain variable domain that is suitable for use as a domain antibody), a single domain antibody (or an heavy chain variable domain that is suitable for use as a single domain antibody), or a "dAb" (or an heavy chain variable domain that is suitable for use as a dAb); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd.

Thus, in particular embodiments, the present invention provides VHH antibodies with the (general) structure
  FR1-CDR1-FR2-CDR2-FR3-CDR3-FR4
    in which FR1 to FR4 refer to framework regions 1 to 4, respectively, and in which CDR1 to CDR3 refer to the complementarity determining regions 1 to 3, respectively, and are as further defined herein.

In particular, the invention in some specific embodiments provides agrochemical compositions comprising at least one VHH antibody that binds at least one fungal species, and that has at least 70%, at least 75%, at least 80%, preferably at least 85%, such as at least 90% or at least 95% or at least 98% sequence identity or more sequence identity with the amino acid sequence of SEQ ID NO: 2, and nucleic acid sequences that encode such amino acid sequences.

Some particularly preferred amino acid sequences of a VHH antibody as disclosed herein are those which can bind to and/or are directed against a pest, such as a fungus, and which have at least 90% (for example at least 95% or at least 97%) amino acid identity with the amino acid sequence of SEQ ID NO: 2 wherein any variation in sequence compared to the reference sequence (i.e. the specified SEQ ID NO sequence) occurs only in the CDR regions. Some particularly preferred amino acid sequences of a VHH antibody as disclosed herein are those which can bind to and/or are directed against a pest, such as a fungus, and which have at least 90% (for example at least 95% or at least 97%) amino acid identity with the amino acid sequence of SEQ ID NO: 2 wherein any variation in sequence compared to the reference sequence (i.e. specified SEQ ID NO sequence) occurs only in the framework regions. In other embodiments, variations in the sequence compared to the reference sequence (i.e. the specified SEQ ID NO sequence) may occur in the CDR regions and/or the framework regions. In some embodiments, variations in the sequence compared to the reference sequence (i.e. the specified SEQ ID NO sequence) may occur in the CDR3 region.

Again, such VHH antibody may be derived in any suitable manner and from any suitable source, and may for example be naturally occurring VHH sequences (i.e. from a suitable species of Camelid) or synthetic or semi-synthetic heavy chain variable domains, including but not limited to "camelized" immunoglobulin sequences (and in particular camelized heavy chain variable domain sequences), as well as those that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person, also including techniques based on mathematic algorithms such as deep learning techniques such as for example the publicly accessible predictive models of IgFold or AlphaFold (see: Fast, accurate antibody structure prediction from deep learning on massive set of natural antibodies. Ruffolo Jeffrey A., Gray Jeffrey J. Biophysical Journal, 2022, Vol 121 (3), 155a-156a DOI: 10.1016/j.bpj.2021.11.1942); or any suitable combination of any of the foregoing as further described herein.

It is understood that the agrochemical compositions or the biological control compositions as disclosed herein are stable, both during storage and during utilization, meaning that the integrity of the agrochemical composition is maintained under storage and/or utilization conditions of the agrochemical composition, which may include elevated temperatures, freeze-thaw cycles, changes in pH or in ionic strength, UV-irradiation, presence of harmful chemicals and the like. More preferably, the VHH antibody remain stable in the agrochemical composition, meaning that the integrity and the fungicidal activity of the VHH antibody is maintained under storage and/or utilization conditions of the agrochemical composition, which may include elevated temperatures, freeze-thaw cycles, changes in pH or in ionic strength, UV-irradiation, presence of harmful chemicals and the like. Most preferably, said VHH antibody remain stable in the agrochemical composition when the agrochemical composition is stored at ambient temperature for a period of two years or when the agrochemical composition is stored at 54° C. for a period of two weeks. Preferably, the agrochemical composition of the present invention retains at least about 70% activity, more preferably at least about 80% activity, most preferably at least about 90% activity or more. Optionally, the VHH antibody may be comprised in a carrier, as defined, to protect the VHH antibody from harmful effects caused by other components in the agrochemical composition or from harmful effects during storage or during application. Examples of suitable carriers include, but are not limited to alginates, gums, starch, β-cyclodextrins, celluloses, polyurea, polyurethane, polyester, microbial cells or clay.

The agrochemical composition may occur in any type of formulation, preferred formulations are powders, wettable powders, wettable granules, water dispersible granules, emulsions, emulsifiable concentrates, dusts, suspensions, suspension concentrates, suspoemulsions (mixtures of suspensions and emulsions), capsule suspensions, aqueous dispersions, oil dispersions, aerosols, pastes, foams, slurries or flowable concentrates.

The VHH antibody, may be the only active substance in the agrochemical or biological control composition according to the invention; however, it is also possible that the agrochemical composition comprises one or more additional agrochemicals, as defined, in addition to the VHH antibody (or the at least one, at least two or at least three VHH antibody as disclosed herein). Such additional agrochemicals or biological control compositions may have a different effect on plant pests as the VHH antibody, they may have a synergistic effect with the VHH antibody, or they may even modify the activity of the VHH antibody on certain plants. Suitable additional agrochemicals can be herbicides, insecticides, fungicides, nematicides, acaricides, bactericides, viricides, plant growth regulators, safeners and the like. Such agrochemicals may be chemicals or may be biological substances, for example a microbial. They include, but are not limited to glyphosate, paraquat, metolachlor, acetochlor, mesotrione, 2,4-D,atrazine, glufosinate, sulfosate, fenoxaprop, pendimethalin, picloram, trifluralin, bromoxynil, captan, clodinafop, Dithiocarbamate, fluroxypyr, phenylpyrroles (such as fludioxonil), hydroxyanilides (such as fenhexamid), dicarboximides (such as iprodione), kresoximmethyl, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, fluopyram, indoxacarb, bifenthrin, tefluthrin, azoxystrobin, thiamethoxam, tebuconazole, mancozeb, morpholine, cyazofamid, fluazinam, Myclobutanil, pyraclostrobin, epoxiconazole, chlorothalonil, strobilurin, triazole, vinclozolin, copper fungicides (for example copper oxychloride, copper hydroxide), anilinopyrimidines (e.g., cyprodinil, pyrimethanil, mepanipyrim), trifloxystrobin, prothioconazole, difenoconazole, carbendazim, propiconazole, thiophanate, sulphur, boscalid, tricyclazole, hexaconazole, metalaxyl, benomyl, benzimidazole, kitazin, tridemorph, propineb, streptomycin sulfate, and oxytetracycline and other known agrochemicals or any suitable combination(s) thereof.

Suitable additional agrochemicals may be a biological substance, such as a microbial, for example a *Pseudomonas* strain such as *Pseudomonas chlororaphis* (ma342), *Pseudomonas* sp. strain dsmz 13134; or a *Bacillus* strain such as *Bacillus thuringiensis* ssp. *aizawai* Abts-1857, *Bacillus thuringiensis* ssp. *aizawai* Gc-91, *Bacillus thuringiensis* ssp. *kurstaki* 10113p/B, *Bacillus thuringiensis* ssp. *kurstaki* Sa-11 10473p/B, *Bacillus thuringiensis* ssp. *kurstaki* Strain EG 2348, *Bacillus thuringiensis* ssp. *israeliensis* (Serotype H-14) Strain AM65-52, *Bacillus amyloliquefaciens* subsp. *plantarum* D747, *Bacillus amyloliquefaciens* MBI 600, *Bacillus amyloliquefaciens* strain FZB24, *Bacillus amyloliquefaciens* strain qst 713, *Bacillus firmus* I-1582; or a *Streptomyces* strain such as *Streptomyces* strain K61; or a *Trichoderma* strain such as *Trichoderma harzianum* T-22, *Trichoderma asperellum* strain T34, *Trichoderma atroviride* strain SC1; or a *Coniothyrium* strain such as *Coniothyrium minitans*, an *Isaria* strain such as *Isaria fumosorosea* var. apopka strain 97; or a *Pythium* strain such as *Pythium oligandrum* M1; or a *Clonostachys* strain such as *Clonostachys rosea* J1446; or a *Paecilomyces* strain such as *Paecilomyces fumosoroseus* FE9901; or a *Metarhizium* strain such as *Metarhizium brunneum* strain MA 43; or a *Beauveria* strain such as *Beauveria bassiana* ATCC 74040, *Beauveria bassiana* strain GHA; or a *Aureobasidium* strain such as *Aureobasidium pullulans* strain DSM14940 or DSM14941; or a *Ampelomyces* strain such as *Ampelomyces quisqualis* strain AQ10; or a *Saccharomyces* strain such as *Saccharomyces cerevisiae* LASO2; or a *Candida* strain such as *Candida oleophila* strain O; or an *Alamthomyce* strain such as *Akanthomyce muscarius* strain VE6. The microbial can also be a virus such as Granulose virus 8615p/b, Granulose virus 9198p/b, Granulose virus 10147p/b Granulose virus 10521p/b Granulose virus 11196 g/b, pepino mosaic virus or a tomato mosaic virus.

Suitable additional agrochemicals may be a bioactive proteins such as a small peptide with anti-microbial properties such as an antimicrobial peptide or AMP. AMPs usually have a length of in the range of 10 to 50 amino acids. AMPs are commonly anionic or cationic and can be subdivided in 4 classes: (i) anionic peptides which are rich in glutamic and aspartic acids, (ii) linear cationic α-helical peptides, (iii) cationic peptides enriched for specific amino acidrich in proline, arginine, phenylalanine, glycine, tryptophan and (iv) anionic/cationic peptides forming disulfide bonds. More specific examples are plant derived AMPs with antimicrobial or antiviral activities such as peptides composed of at least two helical domains connected by a linker/turn such as plant-derived amphipathic helix or two helices engineered into a helix-turn-helix (HTH) format in which homologous or heterogeneous helices are connected by a peptide linker. For example, as described in WO2021202476, WO2020072535, WO2020176224 or WO2003000863. Other examples of bioactive proteins are Bt toxins, e.g., a Cry protein, a Cyt protein, or a Vip protein, or an 6-endotoxin (e.g., Crystal (Cry) toxins and/or cytolytic (Cyt) toxins); vegetative insecticidal proteins (Vips); secreted insecticidal protein (Sips); or Bin-like toxins. "Vip" or "VIP" or "Vegetative Insecticidal Proteins" refer to proteins discovered from screening the supernatant of vegetatively grown strains of Bt for possible insecticidal activity. Vips have little or no similarity to Cry proteins. Of particular use and preference for use with this document are what have been called VIP3 or Vip3 proteins, which have Lepidopteran activity. Vips are thought to have a similar mode of action as Bt cry peptides. Further examples may be polypeptides derived from spider venom such as venom from funnel-web spiders such as agatoxins or diguetoxins more specifically a Mu-diguetoxin-dc1a variant polypeptides or a U1-agatoxin-Ta1b variant polypeptide. Other examples are polypeptides derived from sea anemone, such as Av3 toxins. Such as described in WO2022067214 or WO2021216621 or WO2022212777.

In some aspects, the VHH antibody of the invention may be a bivalent or multivalent VHH antibody, where two or more VHH antibodies are fused to form a fusion protein. In some aspects the bivalent or multivalent VHH antibody comprises the same VHH antibody. In another aspect, the bivalent or multivalent VHH antibody comprises two or more different VHH antibodies. As such, bivalent or multivalent VHH antibodies may bind multiple antigens, where the antigens are identical. Alternatively, bivalent or multivalent VHH antibodies may bind multiple antigens, where the antigens are different. In some cases the antigens may be identical, but the bivalent or multivalent antibodies may bind different epitopes in the same antigen, in other cases the bivalent or multivalent antibodies may bind the same epitopes in the same antigens.

As such, In further particular embodiments, two or more VHH antibodies or a combination of VHH antibodies may be linked to each other or may be interconnected. In particular embodiments, the two or more VHH antibodies or a combination of VHH antibodies are linked to each other via one or more suitable linkers or spacers. Suitable spacers or linkers for use in the coupling of different two or more VHH antibodies or a combination of VHH antibodies as disclosed herein will be clear to the skilled person and may generally be any linker or spacer used in the art to link peptides and/or proteins.

Some particularly suitable linkers or spacers include for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length from 1 to 50 amino acids, such as from 1 to 30, and in particular from 1 to 10 amino acid residues. It should be clear that the length, the degree of flexibility and/or other properties of the linker(s) may have some influence on the properties of the VHH antibodies, including but not limited to the affinity, specificity or avidity for the pest target. It should be clear that when two or more linkers are used, these linkers may be the same or different. In the context and disclosure of the present invention, the person skilled in the art will be able to determine the optimal linkers for the purpose of coupling heavy chain variable domains as disclosed herein without any undue experimental burden.

The VHH antibody of the invention may be produced in a microbial fermentation reaction such as described herein. The VHH antibody of the invention may be expressed in the cytoplasm and released by lysing of the microbial cells. In other aspects, The VHH antibody of the invention may be secreted by the microbial cell. In some aspects, The VHH antibody of the invention may be presented on the surface of a microbial cell or spore. For example, the VHH antibody of the invention may be a fusion protein having a targeting sequence, exosporium protein, or exosporium protein fragment that targets the fusion protein to the exosporium of a recombinant *Bacillus cereus* family member and a pectinase enzyme, wherein the pectinase is a pectate lyase from *Bacillus* spp. Or a polygalaturonase from *Aspergillus niger* or certain *Bacillus* species such as for example disclosed in WO2020190998A1.

Variant VHH Antibodies and Composition Comprising the Same

In a certain aspects, the VHH antibodies comprised in the agrochemical compositions as disclosed herein may be optionally modified, for example to increase the amount of positive charge (that the VHH antibodies has). That is to say, the VHH antibodies may be modified, typically by way of one or more amino acid substitutions, so that the amount of positive charge of the VHH antibodies may be increased. Thus, an amino acid may thus be substituted with an amino acid which has an increased amount of positive charge (compared to the amino acid that it is substituting). More than one such substitutions may be made, for example two, three, four or five such substitutions. In some embodiments, up to one, up to two, up to three, up to four or up to five such substitutions may be made. Such substitutions may typically be made in a CDR region, for example a CDR1 region, a CDR2 region or a CDR3 region.

Other substitutions may also be made the VHH antibodies. In some aspects the VHH antibodies may be modified to improve the binding affinity of the VHH antibody to its target by substituting 1, 2, 3, 4 or 5 or more amino acid. Such substitutions may typically be made in a CDR region, for example a CDR1 region, a CDR2 region or a CDR3 region. In some aspects the VHH antibodies may be modified to improve their physicochemical properties. For instance to improve the stability of the VHH antibody. In other aspects the VHH antibody may be modified to improve the producibility of the VHH antibody from a microbial host cell such as a *Pichia* host cell, a *Trichoderma* host cell, an *Aspergillus* host cell or a *Bacillus* host cell. In some aspects the VHH antibodies may be modified to improve the binding affinity of the VHH antibody to its target by substituting 1, 2, 3, 4 or 5 or more amino acid. Such substitutions may typically be made in a CDR region, for example a CDR1 region, a CDR2 region or a CDR3 region. However, the substitution towards improving the physicochemical properties of the VHH antibody may very well be made in the FR regions, for example in a FR1 region, a FR2 region, a FR3 region or a FR4 region. Examples of possible substitutions are the introduction or removal of disulfide bridges by respectively introducing or removing cysteine residues at the appropriate location. Other examples are the substitution of residues that show to be prone to for example oxidation reactions or other reactions such as hydrolysis such as the cyclisation of a glutamic acid or glutamine to form a lactam, pyroglutamate. For example, the VHH antibody may begin with either a D residue or a Q residue. The present inventors have surprisingly found that having a D residue at position 1 of the VHH antibody (i.e. the first residue of the framework 1 region sequence) may improve the anti-fungal properties of the VHH antibody, although a Q may also be used. Accordingly, for any specified VHH antibody sequence disclosed herein (including the VHH antibody having the sequence of SEQ ID NO: 2 or variants thereof), the residue at position 1 may be a Q residue or, preferably for some embodiments, may be a D residue. In some embodiments the nucleotide sequence encoding the VHH antibody as retrieved after selection from a library of VHH antibody sequences, for example after phage display selection, (i.e. the original sequence obtained from for example an immunised lama) will be altered to encode a D residue instead of a Q residue prior to producing the isolated VHH antibody in for example *E. coli*.

In some embodiments, the invention provides a VHH antibody comprising or consisting of the amino acid sequence set out in SEQ ID NO: 2, or an amino acid sequence having at least about 70%, at least about 75%, at least about 80%, at least about 85%, at least about 90% or at least about 95% or at least about 98% identity thereto.

In some embodiments, the invention provides a VHH antibody comprising or consisting of the amino acid sequence set out in SEQ ID NO: 2, or an amino acid sequence having up to 1, up to 2, up to 3, up to 4 or up to 5 amino acid substitutions thereto. In some embodiment however, the VHH antibody more than 5 amino acids substitution, provided that the VHH antibody binds to at least one fungal species as described herein and causes retardation of growth of a spore of fungus and/or lysis of a spore of the said fungus and where said activity is retained at elevated concentrations of salts, such as CaCl2 or MgCl2 at concentrations as described herein.

Any amino acid substitutions in the VHH antibody may increase the overall charge of the VHH antibody or may not change the overall charge of the VHH antibody. In some embodiments, any amino acid substitutions do not decrease the overall charge of the VHH antibody.

Any amino acid substitutions in the VHH antibody may occur anywhere in the VHH antibody sequence. Optionally, the amino acid substitutions may be limited to the CDR regions (and in such embodiments, the VHH antibody retain the original framework region sequences), or may be limited to the framework regions. In some embodiments, any substitutions or variation in the sequence may occur in the CDR regions or at any residue up to 2 amino acid residues either side of the CDR regions (as defined by the Kabat numbering system). In some embodiments, any substitutions or variation in the sequence may occur in the CDR regions or at any residue up to 1 amino acid residues either side of the CDR regions (as defined by the Kabat numbering system). In some embodiments, any substitutions or variation in the sequence may occur in the CDR regions or at the residue adjacent to the N terminus of the CDR3 region (as defined by the Kabat numbering system).

The present invention extends to additional mutant or variant forms of the disclosed VHH antibody sequences, for example having additional substitutions or having different combinations of substitutions, or having substitutions as different locations in the VHH antibody sequence.

The present invention also provides VHH antibodies (and compositions comprising VHH antibodies) having certain sequences allowing for mutations or substitutions at specific locations.

Any of the VHH antibodies disclosed here, including the variants thereof, may be comprised in a composition, for example an agrochemical composition.

Generally, although the present invention extends to variants of VHH antibodies, the variant VHH antibodies may retain their functional characteristics, or their functional characteristics may be improved. For example, the variant VHH antibodies may be capable of (specifically) binding to at least one fungal species.

The variants may also cause retardation of growth of a spore of the at least one fungal species and/or lysis of a spore of the said at least one fungal species and where said activity is retained at elevated concentrations of salts, such as CaCl2 or MgCl2 at concentrations as described herein. That is to say, binding of the variant VHH antibody to at least one fungal species results in retardation of growth of a spore of the said at least one fungal species and/or lysis of a spore of the said at least one fungal species and where said activity is retained at elevated concentrations of salts, such as CaCl2 or MgCl2 at concentrations as described herein.

In some embodiments, the variant VHH antibody may cause retardation of growth of a spore of fungus and/or lysis of a spore of the said fungus with an IC50 equal to or less than the IC50 of the reference VHH antibody, particularly the VHH antibody of SEQ ID No: 2, when measured under substantially the same conditions such as described in Example 5. In a preferred embodiment, the variant VHH antibody may cause retardation of growth of a spore of the fungus/and or lysis of a spore of the said fungus with an IC50 equal to or less than the IC50 of the reference VHH antibody, particularly the VHH antibody of SEQ ID No: 2, when measured under substantially the same conditions such as described in Example 5 and in the presence of 100 mM NaCl. In an alternative embodiment, the variant VHH antibody may retain 50% of its ability to cause retardation of growth of a spore of the fungus and/or lysis of a spore of the fungus at a MgCl2 concentration that is equal or higher than the concentrations described above for the VHH antibody of the current invention, preferably the VHH antibody of SEQ ID NO: 2. In yet another alternative embodiment, the variant VHH antibody may retain 50% of its ability to cause retardation of growth of a spore of the fungus and/or lysis of a spore of the fungus at a CaCl2 concentration that is equal or higher than the concentrations described above for the VHH antibody of the current invention, preferably the VHH antibody of SEQ ID NO: 2.

The current invention therefore further relates to a method for obtaining a variant of the VHH antibody comprising or consisting of the amino acid sequence set out in SEQ ID NO: 2. Said method comprises the steps of: (a) selecting a nucleic acid sequence encoding the VHH antibody comprising or consisting of the amino acid sequence set out in SEQ ID NO: 2; (b) modifying the selected nucleic acid sequence encoding the VHH antibody to obtain, when expressed, at least one variant VHH antibody; (c) transforming host cells or unicellular organisms with the modified nucleic acid sequence to express a variant VHH antibody encoded by the modified nucleic acid sequence; (d) assessing the ability of the variant VHH antibody to bind to a fungus; (e) where the variant VHH antibody is not capable of binding to a fungus, repeating the process of steps (a) to (d) until a variant VHH antibody capable of binding to a fungus; (f) where the variant VHH antibody capable of binding to a fungus was identified in step (d), isolating the corresponding modified nucleic acid sequence obtained in step (b) and expressing said nucleic acid, thereby to prepare a variant VHH antibody which binds to the fungus; (g) optionally, isolating and/or purifying the variant VHH antibody; (h) optionally, further manufacturing, isolating and purifying the variant VHH antibody. Suitable techniques to apply in said method for manufacturing a variant VHH antibody that may lead to a variety of modified nucleic acid sequences encoding variant VHH antibodies in step (b) may be, techniques such as error prone PCR, mutagenesis, CDR swapping, but also more directed techniques may be used such as techniques designed to introduce modifications or substitution in a more directed or semi-directed manner, such as techniques based on CRIPSR-Cas, Talens, Zinc-finger enzymes etc. Suitable techniques to apply in said method for manufacturing a variant VHH antibody that may lead to a variety of modified nucleic acid sequences encoding variant VHH antibodies in step (b) may also include techniques based on mathematic algorithms such as deep learning techniques such as for example the publicly accessible predictive models of IgFold or AlphaFold (see: Fast, accurate antibody structure prediction from deep learning on massive set of natural antibodies. Ruffolo Jeffrey A., Gray Jeffrey J. Biophysical Journal, 2022, Vol 121 (3), 155a-156a DOI: 10.1016/j.bpj.2021.11.1942); or any suitable combination of any of the foregoing as further described herein. In some embodiments the method for manufacturing a variant of the VHH antibody comprising or consisting of the amino acid sequence set out in SEQ ID NO: 2 may be implemented in a directed evolution framework where the method as set out above may be iterated multiple times and where suitable VHH variants are further modified by the method as set above leading to incremental improvements of the VHH antibody. VHH antibody variants may still be capable of binding to at least one fungal species and cause retardation of growth of a spore of the at least one fungal species and/or lysis of a spore of the said at least one fungal species and where said activity is retained at elevated concentrations of salts, such as CaCl2 or MgCl2 at concentrations as described herein.

The VHH antibodies and VHH antibody variants as disclosed herein comprise CDR sequences of antibodies, such as heavy chain antibodies, or of VH or VHH sequences that were raised against a pest target as described herein (or may be based on and/or derived from such CDR sequences). It should however be noted that the invention in its broadest sense is not limited to a specific structural role or function that these CDR sequences may have in the VHH antibodies as disclosed herein, as long as these CDR sequences allow a polypeptide to specifically bind to a pest target such as a fungal antigen or a fungal target. Thus, generally, the invention relates to agrochemical compositions comprising a polypeptide that is capable of binding to a pest target, such as a fungal antigen or a fungal target, and that comprises a combination of CDR sequences as described herein. More specifically the invention relates to agrochemical compositions comprising a polypeptide that is capable of binding to at least one fungal species, and that comprises a combination of CDR sequences as described herein and which polypeptide may still be capable of binding to said at least one fungal species and cause retardation of growth of a spore of said at least one fungal species and/or lysis of a spore of said at least one fungal species and where optionally said activity is retained at elevated concentrations of salts, such as CaCl2 or MgCl2 at concentrations as described herein.

Thus, any polypeptide comprising a combination of CDR sequences as described herein in the compositions disclosed herein fall within the scope of this invention including but not limited to microbial proteins, protease inhibitors, toxins, fibronectin, lipocalins, single chain antiparallel coiled coil proteins or repeat motif proteins. Non-limiting examples of such polypeptides, include carbohydrate binding domains (CBD) (Blake et al (2006) J. Biol. Chem. 281, 29321-29329), heavy chain antibodies (hcAb), single domain antibodies (sdAb), minibodies (Tramontano et al (1994) J. Mol. Recognition 7, 9-24), the variable domain of camelid heavy chain antibodies (VHH), the variable domain of the new antigen receptors (VNAR), affibodies (Nygren P. A. (2008) FEBS J. 275, 2668-2676), alphabodies (see WO2010066740), designed ankyrin-repeat domains (DARPins) (Stumpp et al (2008) Drug Discovery Today 13, 695-701), anticalins (Skerra et al (2008) FEBS J. 275, 2677-2683), knottins (Kolmar et al (2008) FEBS J. 275, 2684-2690) and engineered CH2 domains (nanoantibodies, see Dimitrov DS (2009) mAbs 1, 26-28) or other polypeptides that can comprise the CDR sequences according to the invention. Particularly, the polypeptide comprising a combination of CDR sequences as described herein may be selected from the group consisting of DARPins, knottins, alphabodies and VHH's. More particularly, the polypeptide comprising a combination of CDR sequences as described herein are selected from the group consisting of alphabodies and VHH's. Most particularly, the polypeptide comprising a combination of CDR sequences as described herein are VHH's. In some aspects the polypeptides may be selected using computational models to retrieve suitable polypeptides that may comprise or are suitable to receive the CDR sequences according to the invention allowing, through the CDR sequences, said polypeptide to bind a fungal pest or fungal pest antigen. Any of the foregoing polypeptide may be naturally occurring polypeptides (from any suitable species) or synthetic or semi-synthetic polypeptides sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques, well known to the skilled person, or any suitable combination of any of the foregoing, that may or may not be guided by computational models allowing for the identification or in silico engineering of suitable polypeptides for engineering sequences comprising the CDR sequences according to the invention and allowing the polypeptide to specifically bind to a pest target such as a fungal antigen or a fungal target.

In a certain aspects, the VHH antibodies comprised in the agrochemical compositions as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the VHH antibodies as disclosed herein (and/or to the composition in which it is present) and may or may not modify the properties of the VHH antibodies as disclosed herein. Such groups, residues, moieties or binding units may also for example be chemical groups which can be biologically active.

These groups, moieties or residues may be, in particular embodiments, linked N- or C-terminally to the VHH antibodies in the compositions as disclosed herein.

In particular embodiments, the VHH antibodies in the agrochemical compositions as disclosed herein may also have been chemically modified. For example, such a modification may involve the introduction or linkage of one or more functional groups, residues or moieties into or onto the heavy chain variable domain. These groups, residues or moieties may confer one or more desired properties or functionalities to the VHH antibodies. Examples of such functional groups will be clear to the skilled person.

For example, the introduction or linkage of such functional groups to a VHH antibody can result in an increase in the solubility and/or the stability of the VHH antibody, in a reduction of the toxicity of the VHH antibody, or in the elimination or attenuation of any undesirable side effects of the VHH antibody, and/or in other advantageous properties.

In particular embodiments, the one or more groups, residues, moieties are linked to the VHH antibody via one or more suitable linkers or spacers.

Compositions Comprising Fragments of VHH Antibodies

The present invention also encompasses parts, fragments, analogs, mutants, variants, and/or derivatives of the VHH antibodies comprised in the compositions as disclosed herein and/or VHH antibodies comprising or essentially consisting of one or more of such parts, fragments, analogs, mutants, variants, and/or derivatives, as long as these parts, fragments, analogs, mutants, variants, and/or derivatives are suitable for the purposes envisaged herein. Such parts, fragments, analogs, mutants, variants, and/or derivatives according to the invention are still capable of specifically binding to at least one fungal species, for example a plant pathogenic fungus and cause retardation of growth of a spore of the at least one fungal species and/or lysis of a spore of the said at least one fungal species.

Targets

In certain particular embodiments, the compositions as disclosed herein at least comprise a VHH antibody, which binds to a fungus preferably from the fungal species *Botrytis*, such as a plasma membrane component of a fungus.

In certain particular embodiments, the compositions as disclosed herein at least comprise a VHH antibody, which binds to a fungus from the fungal species *Colletotrichum*, such as a plasma membrane component of a fungus.

In certain particular embodiments, the compositions as disclosed herein at least comprise a VHH antibody, which binds to a fungus from the fungal species *Podosphaera*, such as a plasma membrane component of a fungus.

In particular embodiments, the present invention provides agrochemical compositions comprising VHH antibodies that are specifically directed against a structural molecular component of the plasma cell membrane of a pest.

In particular embodiments, the present invention provides agrochemical compositions comprising VHH antibodies that are specifically directed against a structural molecular component of the plasma cell membrane of a pest, which is not a protein.

In particular embodiments, the present invention provides agrochemical compositions comprising VHH antibodies that are specifically directed against a structural molecular component of the plasma cell membrane of a pest, which is a protein.

Forms of Target Antigen

It will be appreciated based on the disclosure herein that for agrochemical and biological control applications, the VHH antibodies of the compositions as disclosed herein may be directed against or specifically bind to several different forms of the pest target, for example a fungal target. It is also expected that the VHH antibodies of the compositions as disclosed herein will bind to a number of naturally occurring or synthetic analogs, variants, mutants, alleles, parts and fragments of their pest target. More particularly, it is expected that the VHH antibodies of the compositions as disclosed herein will bind to at least to those analogs, variants, mutants, alleles, parts and fragments of the target that (still) contain the binding site, part or domain of the natural target to which those VHH antibodies bind.

Formulations

It is envisaged that the VHH antibody content contained in the composition, such as the agrochemical composition, as disclosed herein may vary within a wide range and it is generally up to the manufacturer to modify the concentration range of a particular VHH antibody according to the purpose, such as the specific crop pest which is to be attenuated.

In particular embodiments, the present invention provides agrochemical compositions comprising at least one VHH antibody, wherein said heavy chain variable domain is present in an amount effective to protect or treat a plant or a part of said plant from an infection or other biological interaction with said plant pathogen.

In a specific embodiment the concentration of the VHH antibody contained in the agrochemical composition may be at least 0.0001% by weight.

In a specific embodiment the concentration of the VHH antibody contained in the agrochemical composition may be up to 50% by weight.

In a specific embodiment the concentration of the VHH antibody contained in the agrochemical composition may be from 0.0001% to 50% by weight.

In particular embodiments, the present invention provides agrochemical compositions comprising at least one VHH antibody, wherein the concentration of the at least one VHH antibody in the agrochemical composition ranges from 0.001% to 50% by weight.

In yet another specific embodiment the concentration of the VHH antibody contained in the agrochemical composition may be from 0.001% to 50% by weight. In yet another specific embodiment the concentration of the VHH antibody contained in the agrochemical composition may be from 0.01% to 50% by weight. In yet another specific embodiment the concentration of the VHH antibody contained in the agrochemical composition may be from 0.1% to 50% by weight.

In yet another specific embodiment the concentration of the VHH antibody contained in the agrochemical composition may be from 1% to 50% by weight. In yet another specific embodiment the concentration of the VHH antibody contained in the agrochemical composition may be from 10% to 50% by weight. In yet another specific embodiment the concentration of the VHH antibody contained in the agrochemical composition may be from 0.0001% to 40% by weight. In yet another specific embodiment the concentration of the VHH antibody contained in the agrochemical composition may be from 0.001% to 40% by weight. In yet another specific embodiment the concentration of the VHH antibody contained in the agrochemical composition may be from 0.01% to 40% by weight. In yet another specific embodiment the concentration of the VHH antibody contained in the agrochemical composition may be from 0.1% to 40% by weight. In yet another specific embodiment the concentration of the VHH antibody contained in the agrochemical composition may be from 1% to 40% by weight. In yet another specific embodiment the concentration of the VHH antibody contained in the agrochemical composition may be from 0.0001% to 30% by weight. In yet another specific embodiment the concentration of the VHH antibody contained in the agrochemical composition may be from 0.001% to 30% by weight. In yet another specific embodiment the concentration of the VHH antibody contained in the agrochemical composition may be from 0.01% to 30% by weight. In yet another specific embodiment the concentration of the VHH antibody contained in the agrochemical composition may be from 0.1% to 30% by weight. In yet another specific embodiment the concentration of the VHH antibody contained in the agrochemical composition may be from 1% to 30% by weight. In yet another specific embodiment the concentration of the VHH antibody contained in the agrochemical composition may be from 0.0001% to 10% by weight. In yet another specific embodiment the concentration of the VHH antibody contained in the agrochemical composition may be from 0.001% to 10% by weight. In yet another specific embodiment the concentration of the VHH antibody contained in the agrochemical composition may be from 0.01% to 10% by weight. In yet another specific embodiment the concentration of the VHH antibody contained in the agrochemical composition may be from 0.1% to 10% by weight. In yet another specific embodiment the concentration of the VHH antibody contained in the agrochemical composition may be from 1% to 10% by weight. In yet another specific embodiment the concentration of the VHH antibody contained in the agrochemical composition may be from 0.0001% to 1% by weight. In yet another specific embodiment the concentration of the VHH antibody contained in the agrochemical composition may be from 0.001% to 1% by weight. In yet another specific embodiment the concentration of the VHH antibody contained in the agrochemical composition may be from 0.01% to 1% by weight. In yet another specific embodiment the concentration of the VHH antibody contained in the agrochemical composition may be from 0.1% to 1% by weight. In a preferred embodiment the concentration of the VHH antibody contained in the agrochemical composition is between 5% and 50% by weight. In a more preferred embodiment the concentration of the VHH antibody contained in the agrochemical composition is between 10% and 35% by weight.

In particular embodiments, the agrochemical compositions disclosed herein comprise at least one VHH antibody, which is formulated in an aqueous solution.

In further particular embodiments, the agrochemical compositions disclosed herein comprise at least one VHH antibody and further comprise an agrochemically suitable carrier and/or one or more suitable additive.

The compositions according to the invention may comprise, in addition to the anti-pest VHH antibody described above, solid or liquid carriers which are acceptable in the pest treatment of plants and/or parts of plants and/or surfactants which are also acceptable in the pest treatment of plants and/or parts of plants. In particular, there may be used inert and customary carriers and customary surfactants. These compositions cover not only compositions ready to be applied to the plants and/or parts of plants to be treated by immersion or using a suitable device, but also the commercial concentrated compositions which have to be diluted before application to the plants and/or parts of plants.

These agrochemical compositions according to the invention may also contain any sort of other ingredients such as, for example, protective colloids, adhesives, thickeners, thixotropic agents, penetrating agents, stabilizers, sequestrants, texturing agents, flavouring agents, taste enhancers, sugars, sweeteners, colorants and the like. More generally, the active substances, i.e. the at least one heavy chain variable domain, may be combined with any solid or liquid additives corresponding to the usual formulation techniques.

These agrochemical compositions according to the invention may also contain any sort of other active ingredient such as, for example, other anti-bacterial or anti-fungal active ingredients.

The surfactant may be an emulsifying agent, a dispersing agent or a wetting agent of the ionic or nonionic type or a mixture of such surfactants. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (in particular alkylphenols or arylphenols), salts of esters of sulphosuccinic acids, derivatives of taurine (in particular alkyl taurates), phosphoric esters of polyoxyethylated phenols or alcohols, esters of fatty acids and polyols, sulphate, sulphonate and phosphate functional group-containing derivatives of the above compounds. The presence of at least one surfactant is generally essential when the inert carrier is not soluble in water and when the solvent for application is water.

The agrochemical compositions as disclosed herein are themselves in fairly diverse, solid or liquid, forms.

As solid composition forms, there may be mentioned dustable powders (content of active substance which may be up to 100%) and granules, in particular those obtained by extrusion, by compacting, by impregnation of a granulated carrier, by granulation using a powder as starting material (the content of active substance in these granules being between 0.5 and 80% for these latter cases). Such solid compositions may be optionally used in the form of a liquid which is viscous to a greater or lesser degree, depending on the type of application desired, for example by diluting in water.

As liquid composition forms or forms intended to constitute liquid compositions during application, there may be mentioned solutions, in particular water-soluble concentrates, emulsions, suspension concentrates, wettable powders (or spraying powder), oils and waxes.

The suspension concentrates, which can be applied by spraying, are prepared so as to obtain a stable fluid product which does not form a deposit and they usually contain from 10 to 75% of active substance, from 0.5 to 15% of surfactants, from 0.1 to 10% of thixotropic agents, from 0 to 10% of appropriate additives, such as antifoams, corrosion inhibitors, stabilizers, penetrating agents and adhesives and, as carrier, water or an organic liquid in which the active substance is not or not very soluble: some organic solids or inorganic salts may be dissolved in the carrier to help prevent sedimentation or as antigels for water.

The agrochemical compositions as disclosed herein can be used as such, in form of their formulations or as the use forms prepared therefrom, such as aerosol dispenser, capsule suspension, cold fogging concentrate, hot fogging concentrate, encapsulated granule, fine granule, flowable concentrate for seed treatment, ready-to-use solutions, dustable powder, emulsifiable concentrate, emulsion oil in water, emulsion water in oil, macrogranule, macrogranule, oil dispersible powder, oil miscible flowable concentrate, oil miscible liquid, froths, paste, seed coated with a pesticide, suspension concentrate (flowable concentrate), suspensions-emulsions-concentrates, soluble concentrate, suspensions, soluble powder, granule, water soluble granules or tablets, water soluble powder for seed treatment, wettable powder, natural and synthetic materials impregnated with active compound, micro-encapsulation in polymeric materials and in jackets for seed, microencapsulation biological particles, for example those described in WO2018/201160, WO2018/201161 and WO2019/060903, as well as ULV-cold and hot fogging formulations, gas (under pressure), gas generating product, plant rodlet, powder for dry seed treatment, solution for seed treatment, ultra-low volume (ULV) liquid, ultra-low volume (ULV) suspension, water dispersible granules or tablets, water dispersible powder for slurry treatment.

These formulations are prepared in a known manner by mixing the active compounds or active compound combinations with customary additives, such as, for example, customary extenders and also solvents or diluents, emulsifiers, dispersants, and/or bonding or fixing agent, wetting agents, water repellents, if appropriate siccatives and UV stabilisers, colorants, pigments, defoamers, preservatives, secondary thickeners, adhesives, gibberellins and water as well further processing auxiliaries.

These compositions include not only compositions which are ready to be applied to the plant or seed to be treated by means of a suitable device, such as a spraying or dusting device, but also concentrated commercial compositions which must be diluted before application to the crop.

General Application Methods

The VHH antibodies and compositions of the invention beneficially provide antifungal activity. Therefore, in a particular embodiment, the present invention provides the use of a VHH antibody or composition for use as an antifungal agent. Methods of the invention may comprise applying a VHH antibody or composition to a surface. "Surface" in the context of application of the invention refers to any external or internal substrate or area where the VHH antibody or composition can be applied to. The term encompasses, but is not limited to, human and animal surfaces, such as the skin, mouth, mucous membranes, or respiratory organs (lungs); plant surfaces, such as seeds, shoots, stems, leaves, roots (including tubers), flowers, fruits, vegetables, and tissues and organs; inanimate surfaces, such as the surfaces of objects or equipment, such as agricultural equipment, storage facilities and household surfaces (including countertops, floors, walls, and other areas that may require decontamination from fungal contaminants). In a preferred embodiment, said surface is a plant surfaces, such as leaves.

Methods of Application and Plant Protection or Treatment

In certain aspects, the present invention provides methods comprising applying directly or indirectly an agrochemical composition or VHH antibody of the invention to a plant or a part of the plant. The methods may be performed to a plant field. Thus, the present invention also provides methods comprising applying directly or indirectly an agrochemical composition or VHH antibody of the invention to a plant field. In a particular further embodiment, the agrochemical composition or VHH antibody of the invention is applied to the plant, part of the plant or plant field at an application rate or concentration as detailed herein.

In certain aspects, the present invention provides methods for protecting or treating a plant or a part of a plant from an infection or other biological interaction with a plant pathogen, at least comprising the step of applying directly or indirectly to the plant or to a part of the plant, an agrochemical composition or VHH antibody as disclosed herein. The composition or VHH antibody may be applied under conditions effective to protect or treat the plant or a part of the plant against that infection or biological interaction with the plant pathogen.

In particular embodiments, these methods comprise applying directly or indirectly to the plant or to a part of the plant an agrochemical composition as disclosed herein, for example at an application rate higher than 50 g of the agrochemical composition per hectare, such as but not limited to an application rate higher than 75 g of the agrochemical composition per hectare, such as an application rate higher than 100 g of the agrochemical composition per hectare, or in particular an application rate higher than 200 g of the agrochemical composition per hectare.

In particular embodiments, these methods comprise applying directly or indirectly to the plant or to a part of the plant an agrochemical composition as disclosed herein for example at an application rate between 50 g and 1000 g of the agrochemical composition per hectare, such as but not limited to an application rate of between 50 g and 800 g of the agrochemical composition per hectare, in particular an application rate of between 75 g and 500 g of the agrochemical composition per hectare, such as between 75 g and 200 g of the agrochemical composition per hectare or between 75 g and 150 g per hectare.

In yet another embodiment, the invention provides methods for combating or inhibiting plant pests, which methods comprise applying an agrochemical composition according to the invention to a plant, such as a crop, or a part of a plant or a crop, for example at an application rate below 500 g of said VHH antibody per hectare. In specific embodiments the application rate is below 400 g/ha, below 300 g/ha, below 200 g/ha, below 100 g/ha, 50 g/ha, below 40 g/ha, below 35 g/ha, below 30 g/ha, below 25 g/ha, below 20 g/ha, below 15 g/ha, below 10 g/ha, below 5 g/ha, below 1 g/ha or even lower amounts of VHH antibody/ha. In a further embodiment, said upper application rate may be combined with any one of the following lower application rates to provide a suitable application rate range, namely wherein the application rate is above 0.1 g/ha, above 1 g/ha, above 2 g/ha, above 3 g/ha, above 4 g/ha, above 5 g/ha, above 6 g/ha, above 7 g/ha, above 8 g/ha, above 9 g/ha, above 10 g/ha, above 15 g/ha, or above 20 g/ha. A preferred lower application rate is above 10 g/ha. As is evident therefrom, in a further particular embodiment, the application rate of the VHH antibody according to the invention is between 1 g/ha and 500 g/ha, such as between 10 g/ha and 450 g/ha, such as between 100 g/ha and 400 g/ha, such as between 150 g/ha and 350 g/ha. In a more preferred embodiment, the application rate of the VHH antibody according to the invention is between 100 g/ha and 400 g/ha. Where an application rate is understood as the amount of VHH applied per application, an application being understood as a single event (such as a spray event) of applying the VHH antibody or agrochemical composition comprising said VHH antibody on a crop, field of crops or field of plants. In a specific treatment program, multiple applications may happen over a certain time point. For instance a first application may be followed by a second application and where the time between the first application and the second application may be several days such as one week. In some embodiments up to 10 preferably up to 5 applications may be envisioned. It being understood that such a treatment plan may vary between crops and the plant pathogenic fungus targeted by the treatment.

The VHH antibodies of the current invention have an improved activity over the prior art molecule 10G11_Q1D of PCT publication WO 2021/198396. That is to say, the VHH antibodies of the current invention when treating a plant field against a fungal plant pest require a lower application rate to achieve an activity that is at least equal compared to the prior art molecule 10G11_Q1D. Specifically, the VHH antibodies of the current invention achieve an activity that is at least equal against a fungal plant pest when applied at an application rate of between 100 g/ha and 400 g/ha and as compared to an application rate of 500 g/ha of the prior art molecule 10G11_Q1D. In a preferred embodiment the VHH antibody according to the current invention is applied at an application rate of between 100 g/ha and 400 g/ha when treating or preventing *Botrytis cinerea* infection in grape vines, preferably said application is part of an integrated pest management program, preferably two applications are administered, more preferably one application may be done at flowering and a second application at bunch closure. In some preferred embodiments, the VHH antibodies of the current invention have an improved potency compared to the prior art molecule 10G11_Q1D. In some embodiments, the VHH antibodies of the current invention have an improved efficacy compared to the prior art molecule 10G11_Q1D. In some embodiments, the VHH antibodies of the current invention have both an improved potency and an improved efficacy compared to the prior art molecule 10G11_Q1D.

In yet another embodiment, the invention provides methods for combating or inhibiting plant pests, which methods comprise applying an agrochemical or biological control composition according to the invention to a plant, such as a crop, or a part of a plant or a crop, for example at a concentration of 150 µM or lower. In specific embodiments, the application concentration is any of 0.3 µM, 0.5 µM, 0.7 µM, 1.0 µM, 2.0 µM, 3.0 µM, 4.0 µM, 5.0 µM, 10 µM, 15 µM, 20 µM or higher. In a further embodiment, said lower application concentration may be combined with any one of the following upper application concentrations to provide a suitable application concentration range, namely wherein the application concentration is 150 µM, 140 µM, 130 µM, 120 µM, 110 µM, 100 µM, 90 µM, 80 µM, 70 µM, 60 µM, 50 µM, 40 µM, 30 µM, 20 µM or lower. A preferred lower application concentration is above 5 µM. As is evident therefrom, in a further particular embodiment, the application concentration of the VHH antibody according to the invention is from 2 to 150 µM, such as from 4 µM to 120 µM, such as between 5 µM to 110 µM.

It is understood depending on the crop and the environmental pressure of the plant pests that the farmer can vary the application rate. These application rates variances are specified in the technical sheet delivered with the specific agrochemical composition.

In yet another embodiment, the invention provides the use of the agrochemical or biological control compositions of the invention in combating or inhibiting plant pests.

In yet another embodiment, the invention provides the use of the VHH antibodies of the invention in combating or inhibiting plant pests.

Applying an agrochemical or biological control composition or VHH antibody according to the invention to a crop may be done using any suitable method for applying an agrochemical or biological control composition to a crop, including, but not limited to spraying (including high volume (HV), low volume (LV) and ultra-low volume (ULV) spraying), brushing, dressing, dripping, coating, dipping, immersing, spreading, fogging, applying as small droplets, a mist or an aerosol.

Thus, in particular embodiments, the methods for protecting or treating a plant or a part of a plant from an infection or other biological interaction with a plant pathogen as disclosed herein, comprise applying the agrochemical composition directly or indirectly to the plant or to a part of the plant for example by spraying, atomizing, foaming, fogging, culturing in hydroculture, culturing in hydroponics, coating, submerging, and/or encrusting.

In certain particular embodiments, the present invention provides methods of inhibiting, preventing, reducing or controlling the growth of a plant pathogen, comprising at least the step of applying directly or indirectly to a plant or to a part of said plant, an agrochemical composition as disclosed herein.

In certain other embodiments, the present invention provides methods for of killing a plant pathogen, comprising at least the step of applying directly or indirectly to a plant or to a part of said plant, an agrochemical composition or VHH antibody as disclosed herein.

Alternatively, the application rate of the agrochemical composition according to the invention, meaning the amount of the agrochemical composition that is applied to the crop, is such that 100 g, 50 g, 45 g, 40 g, 35 g, 30 g, 25 g, 20 g, 20 g, 15 g, 10 g, of the VHH antibody, comprised in the agrochemical or biological control composition according to the invention, is applied to the crop per hectare and per application.

According to the methods as disclosed herein, the agrochemical or biological control composition can be applied once to a crop, or it can be applied two or more times after each other with an interval between every two applications. According to the method of the present invention, the agrochemical or biological control composition according to the invention can be applied alone or in mixture with other materials, preferably other agrochemical or biological control compositions, to the crop; alternatively, the agrochemical or biological control composition according to the invention can be applied separately to the crop with other materials, preferably other agrochemical or biological control compositions, applied at different times to the same crop. According to the method of the present invention, the agrochemical or biological control composition according to the invention may be applied to the crop prophylactically, or alternatively, may be applied once target pests have been identified on the particular crop to be treated.

The agrochemical compositions as disclosed herein can be applied directly to a plant, a crop or to one or more parts of the plant by the above mentioned methods, such as directly to the entire plant or directly to one or more parts of the plant, either in a pre-harvest or in a post-harvest stage. Pre-harvest application may have an effect post-harvest. In certain further embodiments, the agrochemical compositions as disclosed herein can be applied directly to one or more parts of the plant by the above mentioned methods, such as directly to the stalks, leaves, tubers, stems, shoots, the seeds, the fruits, the roots, the flowers, grains, the buds etc.

The method of treatment as disclosed herein can also be used in the field of protecting storage goods against attack of plant pathogens. In this method of treatment, application of a composition of the invention may be pre-harvest or post-harvest. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leaves, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

The agrochemical compositions as disclosed herein can also be applied indirectly to a plant, a crop or to one or more parts of the plant by the above mentioned methods, such as indirectly to the entire plant or indirectly to one or more parts of the plant, either in a pre-harvest or in a post-harvest stage. The agrochemical compositions as disclosed herein can be applied close to harvest, such as about three weeks pre-harvest, for example two weeks pre-harvest or one week prior to harvest or less than one week pre-harvest. Pre-harvest application may have an effect post-harvest. Thus, in certain embodiments, the agrochemical compositions as disclosed herein can be applied indirectly to a plant, a crop or to one or more parts of the plant by the above mentioned methods, such as by applying the agrochemical composition to the surroundings or to the medium in which the plant or the one or more parts of the plant are growing or are stored, such as for instance but not limited to the air, the soil, the hydroponic culture, the hydroculture, or the liquid medium, such as for instance the aqueous liquid medium or water, in which the plant or the one or more parts of the plant are growing or are stored.

The agrochemical compositions as disclosed herein can be applied directly as a component of an integrated pest management approach.

It thus should be generally understood in the context of this application that the treatment of plants and plant parts with the agrochemical compositions as disclosed herein is carried out directly or by action on their environment, habitat or storage area by means of the normal treatment methods, for example by watering (drenching), drip irrigation, spraying, vaporizing, atomizing, broadcasting, dusting, foaming, spreading-on, and as a powder. It is furthermore possible to apply the compositions by the ultra-low volume method, or to inject the active compound preparation or the active compound itself into the soil.

In particular embodiments, the methods for protecting or treating a plant or a part of a plant from an infection or other biological interaction with a plant pathogen as disclosed herein, comprise applying the agrochemical composition directly or indirectly to the plant or to a part of the plant either in a pre-harvest or in a post-harvest stage. In a particular embodiment, it is applied to a plant or a part of the plant in a post-harvest stage, also referred to herein as harvested produce.

According to specific embodiments, the harvested produce is a fruit, flower, nut or vegetable, a fruit or vegetable with inedible peel, preferably selected from avocados, bananas, plantains, lemons, grapefruits, melons, oranges, pineapples, kiwi fruits, guavas, mandarins, mangoes, squash, strawberries, grapes and pumpkin, is preferred, more preferably bananas, oranges, lemons and peaches, bananas. According to further specific embodiments, the harvested produce is a cut flower from ornamental plants, preferably selected from *Alstroemeria, Carnation, Chrysanthemum, Freesia, Gerbera, Gladiolus*, baby's breath (*Gypsophila* spec), *Helianthus, Hydrangea, Lilium, Lisianthus*, roses and summer flowers.

The plant species to which the agrochemical compositions as disclosed herein can be applied can for example be but are not limited to maize, soya bean, alfalfa, cotton, sunflower, *Brassica* oil seeds such as *Brassica napus* (e.g. canola, rape-seed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Moraceae sp., Oleaceae sp. (e.g. olive tree), Actinidaceae sp., Lauraceae sp. (e.g. avocado, cinnamon, camphor), Musaceae sp. (e.g. banana trees and plantations), Rubiaceae sp. (e.g. coffee), Theaceae sp. (e.g. tea), Sterculiceae sp., Rutaceae sp. (e.g. lemons, oranges, mandarins and grapefruit); Solanaceae sp. (e.g. tomatoes, potatoes, peppers, capsicum, aubergines, tobacco), Liliaceae sp., Compositae sp. (e.g. lettuce, artichokes and chicory—including root chicory, endive or common chicory), Umbelliferae sp. (e.g. carrots, parsley, celery and celeriac), Cucurbitaceae sp. (e.g. cucumbers including gherkins, pumpkins, watermelons, calabashes and melons), Alliaceae sp. (e.g. leeks and onions), Cruciferae sp. (e.g. white cabbage, red cabbage, broccoli, cauliflow-er, Brussels sprouts, pak choi, kohlrabi, radishes, horseradish, cress and Chinese cabbage), Leguminosae sp. (e.g. peanuts, peas, lentils and beans—e.g. common beans and broad beans), Chenopodiaceae sp. (e.g. Swiss chard, fodder beet, spinach, beetroot), Linaceae sp. (e.g. hemp), Cannabeacea sp. (e.g. cannabis), Malvaceae sp. (e.g. okra, cocoa), Papaveraceae (e.g. poppy), Asparagaceae (e.g. asparagus); useful plants and ornamental plants in the garden and woods including turf, lawn, grass and *Stevia rebaudiana*; and in each case genetically modified types of these plants.

In a preferred embodiment of the treatment methods disclosed herein, the crop is selected from the group consisting of field crops, grasses, fruits and vegetables, lawns, trees and ornamental plants.

In certain aspects, the present invention thus also provides post-harvest treatment methods for protecting or treating a harvested plant or a harvested part of the plant from an infection or other biological interaction with a plant pathogen, at least comprising the step of applying directly or indirectly to the harvested plant or to a harvested part of the plant, an agrochemical composition as disclosed herein, under conditions effective to protect or treat the harvested plant or a harvested part of the plant against the infection or biological interaction with the plant pathogen. According to specific embodiments, the harvested produce is a fruit, flower, nut or vegetable, a fruit or vegetable with inedible peel, preferably selected from avocados, bananas, plantains, lemons, grapefruits, melons, oranges, pineapples, kiwi fruits, guavas, mandarins, mangoes and pumpkin, is preferred, more preferably bananas, oranges, lemons and peaches, bananas. According to further specific embodiments, the harvested produce is a cut flower from ornamental plants, preferably selected from *Alstroemeria, Carnation, Chrysanthemum, Freesia, Gerbera, Gladiolus*, baby's breath (*Gypsophila* spec), *Helianthus, Hydrangea, Lilium, Lisianthus*, roses and summer flowers. According to further specific embodiments, the harvested produce is cut grass or wood.

Post-harvest disorders are e.g. lenticel spots, scorch, senescent breakdown, bitter pit, scald, water core, browning, vascular breakdown, $CO_2$ injury, $CO_2$ or $O_2$ deficiency, and softening.

In further aspects, the present invention provides uses of the agrochemical compositions as disclosed herein as an anti-pest agent, including but not limited to a fungistatic or a fungicidal agent.

In a particular embodiment, the plant pests combated by the method according to the present invention are plant pathogenic fungi, as defined before. Lesion number, lesion size, and extent of sporulation of fungal pathogens may all be decreased as a result of the application of the method according to the present invention.

Medical Applications

In certain other embodiments, the present invention provides methods for protecting or curing a human or animal from an infection by a pest and in particular a fungus, or a method of treating or preventing an infection of a human or animal by a pest and in particular a fungus. These methods comprise the step of applying or administering directly or indirectly to the human or animal or to a part of the human or animal, a composition comprising at least one VHH antibody of the invention, which specifically binds to a pest, such as but not limited to a fungus. The composition may be applied to administered under conditions effective to protect or cure the human or animal from the pest. Thus, the present invention provides the a VHH antibody or composition of the invention for use as a medicine. Furthermore, the present invention provides a VHH antibody or composition of the invention for use in the treatment and/or prevention of the diseases and disorders disclosed herein, preferably for use in the treatment and/or prevention of a fungal infection.

Accordingly, the present invention provides VHH antibodies of the invention that specifically bind to a pest target for use in a method for the prevention and/or treatment of at least one disease and/or disorder caused by a pest, such as for example a disease and/or disorder caused by a fungus in a subject. The present invention also provides compositions of the invention for use in a method for the prevention and/or treatment of at least one disease and/or disorder caused by a pest, such as for example a disease and/or disorder caused by a fungus in a subject. The present invention also provides VHH antibodies of the invention that specifically bind to at least one fungal species for use in a method for the prevention and/or treatment of an infection cause by a pest, such as a fungal infection, in a subject. The present invention also provides compositions of the invention that specifically bind to at least one fungal species for use in a method for the prevention and/or treatment of an infection cause by a pest, such as a fungal infection, in a subject. In particular embodiments, the present invention also provides methods for the prevention and/or treatment of at least one disease and/or disorder caused by a pest, comprising administering to a subject in need thereof, a pharmaceutically active amount of one or more VHH antibodies and/or pharmaceutical compositions as disclosed herein. In particular, the pharmaceutically active amount may be an amount that is sufficient (to create a level of the VHH antibody in circulation) to inhibit, prevent or decrease one or more biological activities or pathways of the pest bound thereby.

Therefore, in certain aspects the present invention provides compositions comprising at least one VHH antibody, which specifically binds to a pest for use as an anti-pest agent in a subject, such as an animal or a human being, suffering from a disease and/or disorder caused by a pest (e.g. a fungus).

In specific embodiments, the anti-pest agent is a biostatic or a pesticidal agent. In specific embodiments, the anti-pest agent is a fungistatic or a fungicidal agent.

Also, in certain aspects, the present invention provides methods for the prevention and/or treatment of a disease and/or disorder caused by a pest, which methods comprise the steps of:
(a) providing a VHH antibody or composition as disclosed herein,
(b) administering the VHH antibody or pharmaceutical composition to a patient suffering from the disease and/or disorder caused by a pest.

The efficacy of the VHH antibodies as disclosed herein, and of compositions comprising the same, can be tested using any suitable in vitro assay, cell-based assay, in vivo assay and/or animal model known per se, or any combination thereof, depending on the specific disease or disorder involved.

Suitable assays and animal models will be clear to the skilled person as well as the assays and animal models used in the experimental part below and in the prior art cited herein. The skilled person will generally be able to select a suitable in vitro assay, cellular assay or animal model to test the VHH antibodies as disclosed herein for binding to at least one fungal species, and/or the biological mechanisms in which it is involved; as well as for their therapeutic and/or prophylactic effect in respect of one or more diseases and disorders that are associated with the pest antigen.

Pharmaceutical Compositions

In yet a further aspect, the present invention provides pharmaceutical compositions comprising one or more VHH antibody as disclosed herein and optionally at least one pharmaceutically acceptable carrier (also referred to herein as pharmaceutical compositions of the invention). According to certain particular embodiments, the pharmaceutical compositions as disclosed herein may further optionally comprise at least one other pharmaceutically active compound. The present invention furthermore provides the use of the VHH antibodies of the invention in the manufacture of a medicament, in particular in the manufacture of a medicament for treating the diseases as described herein, more in particular in the manufacture of a medicament to treat a fungal infection.

The pharmaceutical compositions of the present invention can be used in the diagnosis, prevention and/or treatment of diseases and disorders associated with the pest, such as a fungus, of which the pest target is bound to the VHH antibodies disclosed herein.

In particular, the present invention provides pharmaceutical compositions comprising VHH antibodies that are suitable for prophylactic, therapeutic and/or diagnostic use in a warm-blooded animal, and in particular in a mammal, and more in particular in a human being.

The present invention also provides pharmaceutical compositions comprising VHH antibodies as disclosed herein that can be used for veterinary purposes in the prevention and/or treatment or diagnosis of one or more diseases, disorders or conditions associated with the pest, such as for instance a fungus, of which the pest target is bound to the VHH antibodies disclosed herein.

Generally, for pharmaceutical use, the VHH antibodies as disclosed herein may be formulated as a pharmaceutical preparation or compositions comprising at least one VHH antibody as disclosed herein and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation. Thus, the VHH antibodies as disclosed herein and/or the compositions comprising the same can for example be administered orally, intraperitoneally (e.g. intravenously, subcutaneously, intramuscularly, transdermally, topically, by means of a suppository, by inhalation, again depending on the specific pharmaceutical formulation or composition to be used. The clinician will be able to select a suitable route of administration and a suitable pharmaceutical formulation or composition to be used in such administration.

The pharmaceutical compositions may also contain suitable binders, disintegrating agents, sweetening agents or flavoring agents. Tablets, pills, or capsules may be coated for instance with gelatin, wax or sugar and the like. In addition, the amino acid sequences and VHH antibodies as disclosed herein may be incorporated into sustained-release preparations and devices.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Antibacterial and antifungal agents and the like can optionally be added.

Useful dosages of the VHH antibodies as disclosed herein can be determined by comparing their in vitro activity, and in vivo activity in animal models. Methods for the extrapolation of effective dosages in mice, and other animals, to humans are known to the skilled person.

The amount of the VHH antibodies as disclosed herein required for use in prophylaxis and/or treatment may vary not only with the particular VHH antibodies selected but also with the route of administration, the nature of the condition being treated and the age and condition of the patient and will be ultimately at the discretion of the attendant physician or clinician. Also the dosage of the VHH antibodies as disclosed herein may vary depending on the target cell, tumor, tissue, graft, or organ.

The VHH antibodies as disclosed herein and/or the compositions comprising the same are administered according to a regimen of treatment that is suitable for preventing and/or treating the disease or disorder to be prognosed, diagnosed, prevented or treated. The clinician will generally be able to determine a suitable treatment regimen. Generally, the treatment regimen will comprise the administration of one or more VHH antibodies as disclosed herein, or of one or more compositions comprising the same, in one or more pharmaceutically effective amounts or doses.

The desired dose may conveniently be presented in a single dose or as divided doses (which can again be sub-dosed) administered at appropriate intervals. An administration regimen could include long-term (i.e., at least two weeks, and for example several months or years) or daily treatment.

The VHH antibodies as disclosed herein will be administered in an amount which will be determined by the medical practitioner based inter alia on the severity of the condition and the patient to be treated. Typically, for each disease indication an optical dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

In particular, the VHH antibodies as disclosed herein may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

Compositions of the invention may be used in conjunction with known anti-fungals. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref 57]. Compositions may also be used in conjunction with known antivirals e.g. HIV protease inhibitors, a 2',3'-dideoxynucleoside (e.g. DDC, DDI), 3'-azido-2',3'-dideoxynucleosides (AZT), 3'-fluoro-2',3'-dideoxynucleosides (FLT), 2',3'-didehydro-2',3'-dideoxynucleosides (e.g. D4C, D4T) and carbocyclic derivatives thereof (e.g. carbovir), 2'-fluoro-ara-2',3'-dideoxynucleosides, 1,3-dioxolane derivatives (e.g. 2',3'-dideoxyl-3'-thiacytidine), oxetanocin analogues and carbocyclic derivatives thereof (e.g. cyclobut-G) and the 9-(2-phosphonylmethoxyethyl)adenine (PMEA) and 9-(3-fluoro-2-phosphonylmethoxypropyl)adenine (FPMPA) derivatives, tetrahydro-irmidazo[4,5,1jk][1,4]-benzodiazepin-2(1H)one (TIBO), 1-[(2-hydroxyethoxy)-methyl]-6-(phenylthio)thymine (HEPT), dipyrido[3,2-b:2',3'-e]-[1,4] diazepin-6-one (nevirapine) and pyridin-2(1H)one derivatives, 3TC, etc.

The VHH antibodies and pharmaceutical compositions are particularly useful for treating infections in animals and humans of *Candida* species, such as *C. albicans*; *Cryptococcus* species, such as *C. neoformans*; *Enterococcus* species, such as *E. faecalis*; *Streptococcus* species, such as *S*pneumoniae, *S. mutans*, *S. agalactiae* and *S. pyogenes*; *Leishmania* species, such as *L. major* and *L. infantum*; *Acanthamoeba* species, such as *A. castellani*; *Aspergillus* species, such as *A. fumigatus* and *A. flavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. iminitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythiumn* species such as *P. insidiosum*; and *Escherichia* species, such as *E. coli*. The VHH antibodies and pharmaceutical compositions comprising the same as disclosed herein are particularly useful for treating diseases including, but not limited to: candidosis, aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, keratitis, cystic fibrosis, typhoid fever, gastroenteritis and hemolytic-uremic syndrome. Anti *C. albicans* activity is particularly useful for treating infections in AIDS patients.

Methods of Preparing or Generating VHH Antibodies

The invention further provides methods for preparing or generating the VHH antibodies, as well as methods for producing nucleic acids encoding these and host cells, products and compositions comprising these VHH antibodies. Some preferred but non-limiting examples of such methods will become clear from the further description herein.

As will be clear to the skilled person, one particularly useful method for preparing VHH antibodies as disclosed herein generally comprises the steps of:

(a) expressing a nucleotide sequence encoding a VHH antibody as disclosed herein or a vector or genetic construct a nucleotide sequence encoding that VHH antibody and (b) optionally isolating and/or purifying the VHH antibody sequence.

In particular embodiments envisaged herein, the pest-specific VHH antibody sequences can be obtained by methods which involve generating a random library of amino acid sequences and screening this library for a VHH antibody capable of binding to at least one fungal species.

Accordingly, in particular embodiments, methods for preparing a VHH antibody as disclosed herein comprise the steps of a) providing a set, collection or library of VHH antibody sequences;

b) screening said set, collection or library of VHH antibody sequences that can bind to and/or have affinity for at least one fungal species;
c) either (i) isolating said VHH antibody sequence; or (ii) isolating from said cell a nucleic acid sequence that encodes said VHH antibody sequence, followed by expressing said VHH antibody sequence; and
d) selecting the VHH antibodies of the current invention by screening the VHH antibody sequence(s) of step c for their ability to cause retardation of growth of a spore of at least one fungal species and/or lysis of a spore of at least one fungal species and where said activity is retained at elevated concentrations of salts, such as NaCl, $CaCl_2$) or $MgCl_2$ at concentrations as described herein.

In such a method, the set, collection or library of VHH antibody sequences may be any suitable set, collection or library of VHH antibody sequences. For example, the set, collection or library of VHH antibody sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of VHH antibody sequences may be an immune set, collection or library of immunoglobulin fragment sequences, for example derived from a mammal that has been suitably immunized with a fungal species or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of VHH antibody sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

a)

In the above methods, the pest target may be spores or mycelium either intact or homogenized. Alternatively the pest target may be a fraction of said spores or mycelium containing fraction of the plasma membrane of a fungus (for example *Botrytis cinerea* or other fungus). Said lipid-containing fraction may be obtainable by chromatography.

The invention also relates to VHH antibodies that are obtainable or obtained by the above methods, or alternatively by a method that comprises one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Methods of Manufacturing a VHH Antibody

The present invention provides methods for the manufacturing (or production) of a VHH antibody. In some embodiments, the method comprises: culturing a microbial host cell comprising a polynucleotide capable of expressing the VHH antibody of the invention, or a microbial host cell comprising an expression cassette or vector comprising a polynucleotide capable of expressing the VHH antibody of the invention, under conditions to induce expression of the VHH antibody, and optionally isolating and/or purifying the VHH antibody from the culture medium or fermentation broth, optionally modifying the protein, and optionally formulating the protein.

"Culturing", "cultivation", "cell culture", "fermentation", "fermenting" or "microbial fermentation" as used herein means the use of a microbial host cell to produce or manufacture a protein, such as a VHH antibody, at an industrial scale, laboratory scale or during scale-up experiments. It includes suspending the microbial cell in a broth or growth medium, providing sufficient nutrients including but not limited to one or more suitable carbon source (including glucose, sucrose, fructose, lactose, Avicel®, xylose, galactose, ethanol, methanol, or more complex carbon sources such as molasses or wort), nitrogen source (such as yeast extract, peptone or beef extract), trace element (such as iron, copper, magnesium, manganese or calcium), amino acid or salt (such as sodium chloride, magnesium chloride or natrium sulfate) or a suitable buffer (such as phosphate buffer, succinate buffer, HEPES buffer, MOPS buffer or Tris buffer). Optionally it includes one or more inducing agents driving expression of a VHH antibody (such as lactose, IPTG, ethanol, methanol, sophorose or sophorolipids). If can also further involve the agitation of the culture media via for example stirring of purging to allow for adequate mixing and aeration. It can further involve different operational strategies such as batch cultivation, fed-batch cultivation, semi-continuous cultivation or continuous cultivation and different starvation or induction regimes according to the requirements of the microbial cell and to allow for an efficient production of the VHH antibody. Alternatively, the microbial cell is grown on a solid substrate in an operational strategy commonly known as solid state fermentation.

Fermentation broth, culture media or cell culture media as used herein can mean the entirety of liquid or solid material of a fermentation or culture at any time during or after that fermentation or culture, including the liquid or solid material that results after optional steps taken to isolate the VHH antibody. As such, the fermentation broth or culture media as defined herein includes the surroundings of the protein after isolation of the protein, during storage and/or during use as an agrochemical or pharmaceutical composition. Fermentation broth is also referred to herein as a culture medium or cell culture medium.

"Isolating the VHH antibody" is an optional step or series of steps taking the cell culture media or fermentation broth as an input and increasing the amount of the VHH antibody relative to the amount of culture media or fermentation broth. Isolating the VHH antibody may alternatively or additionally comprises obtaining or removing the VHH antibody form the culture media or fermentation broth. Isolating the VHH antibody can involve the use of one or multiple combinations of techniques well known in the art, such as precipitation, centrifugation, sedimentation, filtration, diafiltration, affinity purification, size exclusion chromatography and/or ion exchange chromatography. Isolating the VHH antibody may be followed by formulation of the VHH antibody into an agrochemical or pharmaceutical composition.

Isolation of VHH Antibodies

In some cases, the methods for producing the VHH antibodies binding to at least one fungal species as envisaged herein may further comprise the step of isolating from the VHH antibody sequence library at least one VHH antibody having detectable binding affinity for, or detectable in vitro effect, preferably in the presence of salts, such as MgCl2 or CaCl2 as described herein, on, at least one fungal species.

These methods may further comprise the step of amplifying a sequence encoding at least one VHH antibody having detectable binding affinity for, or detectable in vitro effect, preferably in the presence of salts, such as NaCl, MgCl2 or CaCl2 as described herein, on, at least one fungal species. For example, a phage clone displaying a particular VHH antibody, obtained from a selection step of a method described herein, may be amplified by reinfection of a host bacteria and incubation in a growth medium.

In particular embodiments, these methods may encompass determining the sequence of the one or more VHH antibodies capable of binding to at least one fungal species.

Where a VHH antibody sequence, comprised in a set, collection or library of amino acid sequences, is displayed on a suitable cell or phage or particle, it is possible to isolate from said cell or phage or particle, the nucleotide sequence that encodes that VHH antibody sequence. In this way, the nucleotide sequence of the selected amino acid sequence library member(s) can be determined by a routine sequencing method.

In further particular embodiments, the methods for producing a VHH antibody as envisaged herein comprise the step of expressing said nucleotide sequence(s) in a host organism under suitable conditions, so as to obtain the actual desired amino acid sequence. This step can be performed by methods known to the person skilled in the art.

In addition, the obtained VHH antibody sequences having detectable binding affinity for, or detectable in vitro effect, preferably in the presence of salts, such as NaCl, MgCl2 or CaCl2 as described herein, on, at least one fungal species, may be synthesized as soluble protein construct, optionally after their sequence has been identified.

For instance, the VHH antibody sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the VHH antibody sequences obtained, obtainable or selected by the above methods may comprise transforming or infecting a host cell with a nucleic acid or a vector encoding an VHH antibody sequence having detectable binding affinity for, or detectable in vitro effect on the activity of a pest target. Accordingly, VHH antibody sequences having detectable binding affinity for, or detectable in vitro effect on the activity of a pest target can be made by recombinant DNA methods. DNA encoding the VHH antibody can be readily synthesized using conventional procedures. Once prepared, the DNA can be introduced into expression vectors, which can then be transformed or transfected into host cells such as E. coli or any suitable expression system, in order to obtain the expression of VHH antibodies in the recombinant host cells and/or in the medium in which these recombinant host cells reside.

The term "vector" or "expression vector" as used herein in the context of recombinant expression or cloning of nucleotide sequences means a DNA molecule used as a vehicle to transfer, replicate, or express specific genes or DNA sequences in a host organisms (such as E. coli or P. pastoris). Vectors may be designed to carry genes of interest and may be equipped with regulatory elements like promoters, terminators, start and stop codons, and also a multiple cloning site, selection markers and typically have an origin of replication that allows the vector to be replicated in the host organisms. Where such origin of replication is absent or non-functional in the host organism, such a vector is commonly described as a suicide vector. In general a vector can be seen as a genetic carriers for introducing foreign DNA into host cells, facilitating the production of recombinant proteins or other genetic manipulations. Vectors can be plasmids (typically a small, circular, double-stranded DNA molecule), viruses, or other genetic elements.

It should be understood, as known by someone skilled in the art of protein expression and purification, that the VHH antibody produced from an expression vector using a suitable expression system may be tagged (typically at the N-terminal or C-terminal end of the amino acid sequence) with e.g. a His-tag, strep-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired VHH antibody sequences may be any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic plant or animal. More specific examples of suitable host cells for expression of the desired VHH antibody sequences are selected from the group of Komagataella sp., Trichoderma sp., Aspergillus sp. and Bacillus sp. More specifically from the group of Komagataella phaffii, Trichoderma reesei, Aspergillus niger, Bacillus subtilis, and Bacillus licheniformis.

Nucleic Acid Sequences

In a further aspect, the present invention provides nucleic acid sequences encoding the VHH antibody sequences as disclosed herein (or suitable fragments thereof). These nucleic acid sequences can also be in the form of a vector or a genetic construct or polynucleotide. The nucleic acid sequences as disclosed herein may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

The present invention includes a nucleic acid sequence encoding any VHH antibody disclosed herein. For example, the present invention includes a nucleic acid sequence encoding a VHH antibody comprising or consisting of the amino acid sequence set out in SEQ ID NO: 1, as well as variants thereof, such as those having amino acid substitutions or certain percent identity thereto.

The VHH antibody sequences may be encoded by a nucleic acid that is optimized for expression in certain micro-organisms. For example, the codon-usage bias (i.e. the preferential bias an organism has for a codon triplet matching a certain amino acid) may differ between organisms, therefor selecting the correct codon to encode a protein of interest for a given organism may improve the expression levels of said protein of interest. The chosen nucleotide sequences can therefore differ whilst still encoding the same VHH antibody. Several online algorithms are available for generating a codon optimized nucleotide sequences encoding the VHH antibody sequence as presented here. For example, the skilled person may choose from several online available tools to perform codon optimization specifically suited for the pro- or eukaryotic host cell for expressing the VHH antibodies of the current invention. For example GeneArt (available on https://www.thermofisher.com/be/en/home/life-science/cloning/gene-synthesis.html), ATUM (available on https://www.atum.bio/), Vector Builder (available on https://en.vectorbuilder.com/tool/codon-optimization.html) all provide tools for optimizing the codon-usage bias for a given recombinant protein. In some embodiments the nucleotide sequence encoding the VHH antibody as retrieved after selection from a library of VHH antibody sequences, for example after phage display selection, (i.e. the original sequence obtained from for example an immunised lama) will be codon optimized by optimizing the sequence for improved expression in *E. coli*. The VHH antibody of the current invention may for instance be coded by a nucleotide sequence selected from SEQ ID NOs: 10 to 12 for expression in *Komagataella phaffii* (aka *Pichia pastoris*), or SEQ ID NOs: 13 or 14 for expression in *Trichoderma reesei* or *Aspergillus niger*, or SEQ ID NO: 15 for expression in *Bacillus subtilis* or *Bacillus licheniformis*. The skilled person will know that one is often required to assess several possible codon optimization strategies to find the most efficient codon usage for the specific host cell and the specific recombinant protein of interest. Therefore, the current invention provides a nucleic acid according to SEQ ID NO:1 encoding the VHH antibody according to SEQ ID NO: 2. The current invention further provides codon-optimized nucleic acids encoding the VHH antibody according to SEQ ID NO: 2. More specifically, the current invention provides codon-optimized nucleic acid selected from the group of SEQ ID NOs 10 to 15 encoding SEQ ID NO: 2 or a codon-optimized nucleic acid with at least 60% identity to SEQ ID NO: 1 encoding SEQ ID NO: 2. More specifically the current invention provides codon optimized nucleic acids with between 60% and 90% identity to SEQ ID NO: 1 encoding SEQ ID NO: 2, more specifically between 65 and 85% identity, more specifically between 70% and 80% identity to SEQ ID NO: 1 encoding SEQ ID NO: 2.

Constructs, Vectors, Host Cells

The genetic constructs as disclosed herein may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

Accordingly, in another further aspect, the present invention also provides vectors comprising one or more nucleic acid sequences encoding the VHH antibodies of the invention.

In still a further aspect, the present invention provides hosts or host cells that express or are capable of expressing one or more VHH antibodies as disclosed herein.

In yet another embodiment, for use in the methods disclosed herein, the application discloses nucleic acid sequences encoding a VHH antibodies, wherein VHH antibodies are obtained by affinity selection to a specific plant pathogenic target, which VHH antibody is able to inhibit the growth and/or the activity of a crop pest at a minimum inhibitory concentration of about 0.00001 to 1 µM.

Also disclosed are chimeric genes comprising the following operably linked DNA elements: a) a plant expressible promoter, b) a DNA region which when transcribed yields a mRNA molecule capable of being translated into a VHH antibody and c) a 3' end region comprising transcription termination and polyadenylation signals functioning in cells of said plant.

A "chimeric gene" or "chimeric construct" is a recombinant nucleic acid sequence in which a promoter (e.g. a plant expressible promoter) or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence when introduced into a cell such as a plant cell. The regulatory nucleic acid sequence of the chimeric gene is not normally operatively linked to the associated nucleic acid sequence as found in nature.

In the present invention, a "plant promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern.

The term "operably linked" as used herein refers to a functional linkage between the promoter sequence and the gene of interest, such that the promoter sequence is able to initiate transcription of the gene of interest.

Plant expressible promoters comprise nucleic acid sequences which are able to direct the expression of a transgene in a plant. Examples of plant expressible promoters are constitutive promoters which are transcriptionally active during most, but not necessarily all, phases of growth and development and under most environmental conditions, in at least one cell, tissue or organ, other promoters are inducible promoters, other examples are tissue specific promoters, still other examples are abiotic stress inducible promoters.

The chimeric gene (or the expression cassette) when transformed in a plant expresses a nucleic acid which results in expression of a protein.

Also disclosed is a recombinant vector which comprises an expression cassette (or a chimeric gene) as herein described before.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

In certain embodiments the nucleic acid encoding the VHH antibody of the invention is present in a chimeric gene, where the chimeric gene is suitable for expression in a plant, part of a plant, plant cell or specific organelle or compartment of a plant cell. The current invention therefore also encompasses a transgenic plant, part of a transgenic plant, transgenic plant cell or specific organelle or compartment of a plant cell where said transgenic plant, part of a transgenic plant, transgenic plant cell or specific organelle or compartment of a plant cell expresses a nucleic acid sequence encoding the VHH antibody of the current invention. The chimeric gene or the expression cassette may comprise a suitable (plant) expressible promoter, a terminator a selectable marker and/or any other genetic building blocks to allow for successful expression, translation and localisation of the VHH antibody of the current invention in a transgenic plant, part of a transgenic plant, transgenic plant cell or specific organelle or compartment of a plant cell. In the context of a nucleotide encoding the VHH antibody of the invention or in the context of a chimeric gene suitable for expression in plants the term "cleavable leader peptide" as used above may also mean an N-terminal transit peptide or nuclear localisation signal. The VHH antibody of the current invention may be present in a chimeric gene and whereby the chimeric gene comprises an N-terminal transit peptide whereby the N-terminal transit peptide allows the VHH antibody to be translocated from the cytosol into specific organelles such as chloroplasts and mitochondria. In some embodiments, the N-terminal transit peptide is a nuclear localisation signal.

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the VHH antibodies of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences encoding the VHH antibodies, expression cassettes or vectors according to the invention.

A transgenic plant for the purposes of the invention is thus understood as meaning, as above, that the nucleic acids used in the method of the invention are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

The term "increased expression" or "overexpression" as used herein means any form of expression that is additional to the original wild-type expression level. For the purposes of this invention, the original wild-type expression level might also be zero, i.e. absence of expression or immeasurable expression.

Methods for increasing expression of genes or gene products are well documented in the art and include, for example, overexpression driven by appropriate promoters (as described herein before), the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1 183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 1 16, Freeling and Walbot, Eds., Springer, N.Y. (1994).

The term "introduction" or "transformation" as referred to herein encompass the transfer of an exogenous polynucleotide or chimeric gene (or expression cassette) into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al (1984) Nucl. Acids Res. 12-8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, KA and Marks MD (1987). Mol Gen Genet 208:1-9; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). CR Acad Sci Paris Life Sci, 316: 1 194-1 199], while in the case of the "floral dip" method the developing floral tissue is incubated briefly with a surfactant-treated agrobacterial suspension [Clough, S J and Bent AF (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention will now be illustrated by way of the following non-limiting Examples.

EXAMPLES

Example 1: Immunizations

Llamas were immunized according to standard protocols with 3 to 4 injections of 1E+07 spores or 24h old mycelium of *B. cinerea*. Spores and mycelium were prepared in ultrapure water and used either intact or homogenized by freezing in liquid nitrogen and processing frozen sample using metal bearings in a tissue grinder. Spore and mycelium suspensions were mixed with Gerbu adjuvant P (GERBU Biotechnik GmbH) and injected subcutaneously. All llamas remained healthy throughout the immunization process and blood samples were collected before and after the immunization experiment.

Example 2: Library Construction

To generate VHH libraries, peripheral blood mononuclear cells were prepared from blood samples of the immunized llamas using FICOLL PAQUE PLUS (Merck) according to the manufacturer's instructions. Total RNA was extracted from these cells and used as starting material for RT-PCR to amplify VHH encoding gene fragments. These fragments were cloned into phagemid vector pASF20. pASF20 is an expression vector derived from pUC119 which contains the lacZ promoter, a synthetic leader sequence, a multiple cloning site, a coliphage pIII protein encoding sequence, a resistance gene for ampicillin, and an M13 phage origin for single strand production. In frame with the VHH coding sequence, the vector codes for a C-terminal (His)6 peptide tag and a c-myc peptide tag. Phage were prepared according to standard methods (Phage Display of Peptides and Proteins: A Laboratory Manual; Brian K. Kay, Jill Winter, John McCafferty). Libraries with a clonal diversity equal to or greater than 1E+08 were obtained and phage were produced ensuring presentation of antibody diversity.

Example 3: Selections

Panning selections were performed as follows: Per selection condition 1E+05 germinating spores of *B. cinerea* were blocked in microcentrifuge tubes using 10% BSA/PBST (Bovine Serum Albumin in Phosphate Buffer Saline with 0.1% Tween 20) and incubated with library phage (approximately 1E+11 phage particles per selection condition). PBST comprises 137 mM NaCl, 2.7 mM KCl, 10 mM Na2HPO4, 1.8 mM KH2PO4 and 0.1% (w/v) Tween® 20 detergent, which has a high salt concentration. Washes were performed using 10% BSA/PBST and phage was eluted using 0.25 mg/ml trypsin. Four selection rounds were performed and enrichments were observed against an irrelevant library used under the same conditions.

Individual colonies of *E. coli* TG1 cells infected with selected eluted phage pools obtained after the fourth round were picked into 96-well plates, master plates (MP) containing 100 μl of 2×TY medium containing 2% glucose and 100 μg/ml carbenicillin per well and grown overnight at 37° C. MPs were stored in 20% glycerol at −80° C. and used for periplasmic extract production, screening and sequencing.

Example 4: Binding Assays

A selection of candidates was assessed for binding to germinating spores of *B. cinerea* in a dose response experiment. Using round-bottom microtiter plates, 100 000 spores per well were allowed to germinate in PDB medium overnight at 8° C. Serial dilutions of the purified strep-tagged VHHs were incubated with the spores for 1 hour at 4° C. in either HEPES pH7 (low salt) or PBS pH7.4 (referred to as high or elevated salt concentrations). Binding of the VHHs was detected using a monoclonal antibody specific against the strep tag and conjugated to fluorophore DY488. All washes were performed by centrifugation using either HEPES or PBS. Spores of *Trichoderma reesei* were used as irrelevant organism. Binding events were acquired by using a MACSQuantX flow cytometer and median fluorescent intensity (MFI) of DY488 fluorophore was used to plot dose response binding curves. VHH 11A11 was shown to bind to germinating spores of *B. cinerea* in a dose depend manner in both HEPES as PBS (FIG. 1).

Example 5: VHH 11A11 Inhibits the Growth of *Botrytis cinerea* in a Dose-Dependent Manner in an In Vitro Antifungal Assay VHH 11A11 was selected from the phage panning exercise as described in Examples 2 and 3 using germinated *B. cinerea* spores.

The antifungal activity of VHH 11A11 (SEQ ID NO: 2) was assessed in an in vitro assay against the plant pathogenic fungus *Botrytis cinerea*. The current in vitro assay is a standard microtiter plate-based antifungal assay against *Botrytis cinerea* based on confluence analysis using an IncuCyte S3 System. The media used is 1×PDB (Potato Dextrose Broth)(autoclaved) adjusted with NaOH to pH 7 (0.22 μm filter sterilized afterwards). Microtiter plate conditions for low salt conditions were stabilised with 10 mM HEPES buffer pH 7 (autoclaved) and for high salt conditions this 10 mM HEPES buffer pH7 was supplemented with 100 mM NaCl (autoclaved). To the wells of a standard 96-well microtiter plate either 100 μl of 10 mM HEPES buffer pH 7 or 10 mM HEPES/100 mM NaCl pH 7 was added. The VHH were added in a fixed 2-fold dilution series between 20 μM and 0.3125 μM, with 10 mM HEPES buffer or 10 mM HEPES/100 mM NaCl pH 7. No VHH was added for negative control wells and as a positive control (chemical control) 100 μl 80 μM FCCP was added to the control wells. To all wells, 100 μl of a *Botrytis cinerea* cell suspension in PDB medium at 10.000 cells/100 μl was added. For that *Botrytis cinerea* spores were harvest from 2 week old PDA (Potato Dextrose Agar) plates and spore solution was stored at 4° C. before usage. Spore solutions were diluted to 1×10^6 cfu/ml in 1×PDB and diluted before use.

All tests were performed in at least 2 replicates and plates were organized so to correct for positional bias.

The results of the antifungal activity assay with no additional salt, shown in FIG. 2, indicating a clear dose-dependent growth inhibition pattern, expressed as the % fungal growth (% confluency) in function of VHH concentration (μM). The IC50 value for VHH 11A11 was 2.44 μM (FIG. 2). FIG. 3 shows the assay run in high sodium conditions at 100 mM NaCl at pH7. The IC50 value for VHH 11A11 at elevated salt concentration was 4.87 μM (FIG. 3). The IC50 values were measured at the 90% buffer saturation point i.e. when the *Botrytis cinerea* cells of the buffer control reach 90% confluency. In contrast VHH 10G11_Q1D (WO 2021/198396) failed to show good activity at high salt concentration (FIG. 4) but performed well without added salt (FIG. 5).

Example 6: VHH 11A11 Shows Prolonged Activity Against *Botrytis cinerea* in an In-Vitro Antifungal Assay The antifungal assay as described in Example 5 was run for an extended period of time showing prolonged activity of over 20 days. This in contrast to 10G11_Q1D where after approximately 3 days restart of growth of *Botrytis cinerea* can be detected (FIG. 6).

Example 7: VHH 11A11 Retains Activity in the Presence of $MgCl_2$

To assess the ability of VHH 11A11 to retain its activity in the presence of increasing concentrations of MgCl2 in comparison to the VHH of the prior art 10G11_Q1D (WO 2021/198396), the anti-fungal assay as described in Example 5, was performed with a constant concentration of VHH at 5 μM and with concentrations of MgCl2 ranging from 1 to 0 mM MgCl2 in a 4-fold dilution series. The assays were run as described in Example 5. This assay results in a measure of the MgCl2 concentration at which 50% of the anti-fungal activity of VHH 11A11 is lost. As shown in FIG. 7, VHH 11A11 still retained 50% activity at a concentration of 33.0 μM MgCl2, compared to VHH 10G11_Q1D value of 20.5 μM MgCl2. An approximate 2 fold increase in salt tolerance, indicating an increased potency of VHH 11A11 to disrupt the fungal membrane.

Example 8: VHH 11A11 Retains Activity in the Presence of CaCl$_2$

Figure 8:
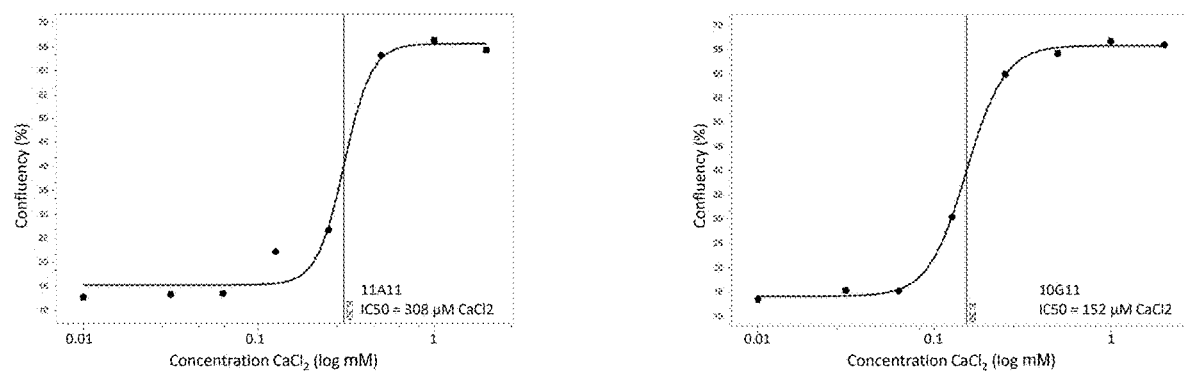
FIG. 8 Dose response curve of an antifungal assay showing influence of increasing concentrations of CaCl2 on the inhibition effect of VHH antibody 11A11 (left panel) and 10G11_Q1D (right panel) on *Botrytis cinerea*.

To assess the ability of VHH 11A11 to retain its activity in the presence of increasing concentrations of CaCl2 in comparison to the VHH of the prior art 10G11_Q1D (WO 2021/198396), the anti-fungal assay as described in Example 5, was performed with a constant concentration of VHH at 5 µM and with concentrations of CaCl2 ranging from 2 to 0 mM CaCl2 in a 4-fold dilution series. The assays were run as described in Example 5. This assay results in a measure of the CaCl2 concentration at which 50% of the anti-fungal activity of VHH 11A11 is lost. As shown in FIG. 8, VHH 11A11 still retained 50% activity at a concentration of 308 µM CaCl2, compared to VHH 10G11_Q1D value of 152 µM CaCl2. An approximate 2 fold increase in salt tolerance, indicating an increased potency of VHH 11A11 to disrupt the fungal membrane.

Example 9: Error Prone PCR

Error prone PCR is a method that may be used for obtaining a variant VHH antibody, such as a variant of the VHH antibody comprising the amino acid sequence of SEQ ID NO: 2, encoded by the nucleotide sequence according to SEQ ID NO: 1. For the error prone PCR (epPCR) reaction an error prone DNA polymerase without proofreading activity may be used optionally in combination with sub-optimal salt concentrations to improve error rate. Here a mixture of two error prone DNA polymerases is used: Mutazyme I DNA polymerase and Taq DNA polymerase (referred to as Mutazyme II from the original GeneMorph Random Mutagenesis Kit). For the PCR reaction standard primers are used that are designed to hybridize at the 5' and 3' end of the VHH nucleotide sequence. Said primers may containing restriction digesting sites or other additional 5'-overhangs to facilitate further downstream cloning. A standard PCR mixture is set-up using the Mutazyme II reagents and instructions (GeneMorph Random Mutagenesis Kit, Agilent). Briefly, a 50 µl PCR reaction is set up comprising 1× Mutazyme II reaction buffer, 200 µM dNTP mix, 50 nM of a forward and reverse primer, 0.05 U/µl of the Mutazyme II DNA polymerase and between 0.1 to 1000 ng of template DNA. Importantly, the mutation rate may be varied by changing the amount of template DNA. Preferably between 0.1 to 100 ng of template DNA is used to obtain a mutation frequency of between 9 to 16 mutations/kb. A standard PCR reaction is run over 20 to 30 cycles. The resulting epPCR product is then subjected to Next Generation Sequencing analysis to obtain an accurate estimate of the mutation rate. Thereafter the epPCR product is cloned into a suitable vector, such as a vector used in a phage-display procedure (see e.g. Example 2). Standard cloning methods such as restriction digesting and ligation cloning, splicing by overlap extension (SOEing) or Gibson assembly may be used therefore. Here traditional restriction digesting and ligation is used and the optimal insert/vector ratio is calculated using the NEB online calculator tool (https://nebiocalculator.neb.com/#!/ligation). The ligation product containing the variant VHH antibodies cloned into a suitable vector is thereafter transformed into competent *E. coli* cells, such as TG1 electrocompetent *E. coli* cells (Biosearch Technologies). Transformation is achieved using electroporation using standard settings for bacteria on the electroporation device (Bio-Rad). Transformants are selected on appropriate selection plates comprising an antibiotic selecting for the presence of the vector. Ideally the library size is between 1×10^3 CFU/ml and 1×10^9 CFU/ml. The mutation rate and sequence diversity is thereafter confirmed by sequencing a colony PCR obtained from a set of 94 different individual colonies. Hereafter the procedure described in Example 3 Selections is repeated and the resulting variants of the input VHH antibody are thereafter screened for improved characteristics such as improved binding affinity (see Example 4) and/or improved antifungal effect (see Examples 5 to 8).

Statements (features) and embodiments of the VHH antibodies, compositions and methods as disclosed herein are set herebelow. Each of the statements and embodiments as disclosed by the invention so defined may be combined with any other statement and/or embodiment unless clearly indicated to the contrary. In particular, any feature indicated as being preferred or advantageous may be combined with any other feature or features indicated as being preferred or advantageous.

Embodiments

The present invention provides at least the following numbered statements of invention:

1. A VHH antibody that binds to at least one fungal species comprising: the amino acid sequence set out in SEQ ID NO: 2, or a sequence having at least 70%, at least 75%, at least 80%, at least 85%, at least 90%, at least 95% or at least 98% identity thereto, or a sequence having up to 1, up to 2, up to 3, up to 4 or up to 5 amino acid substitutions thereto.
2. A VHH antibody that binds to at least one fungal species consisting of the amino acid sequence set out in SEQ ID NO: 2.
3. A VHH antibody that binds to at least one fungal species comprising: a complementarity determining region 1 (CDR1) region comprising or consisting of the sequence set out in SEQ ID NO: 3; a CDR2 region comprising or consisting of the sequence set out in SEQ ID NO: 4; and a CDR3 region comprising or consisting of the sequence set out in SEQ ID NO: 5.
4. The VHH antibody according to statement 3 further comprising: a framework region 1 (FR1) sequence comprising or consisting of the sequence set out SEQ ID NO: 6, a framework region 2 (FR2) sequence comprising or consisting of the sequence set out in SEQ ID NO: 7, a framework region 3 (FR3) sequence comprising or consisting of the sequence set out in SEQ ID NO: 8, and a framework region 4 (FR4) sequence comprising or consisting of the sequence set out in SEQ ID NO: 9.
5. A VHH antibody having at least one, preferably at least two, most preferably all three properties selected from the group consisting of:
   a. capable of binding to at least one fungal species and
   b. causing retardation of growth of a spore of the at least one fungal species and/or lysis of a spore of the at least one fungal species and
   c. whereby the VHH antibody causes retardation of growth of a spore of the at least one fungal species and/or lysis of a spore of the at least one fungal species in the presence of elevated salt concentrations.
6. The VHH antibody according to statement 5, where the VHH antibody causes retardation of the growth of a spore of the at least one fungal species and/or lysis of a spore of the at least one fungal species in the presence of elevated salt concentrations when tested in an anti-fungal assay.

7. The VHH antibody according to statements 5 or 6, where the retardation of the growth of a spore of the at least one fungal species and/or lysis of a spore of the at least one fungal species is improved at elevated salt concentrations relative to a VHH antibody that was not selected to cause retardation of growth of a spore of the at least one fungal species and/or lysis of a spore of the at least one fungal species in the presence of elevated salt concentrations when tested in an anti-fungal assay.
8. The VHH antibody according to statements 6 or 7, where the anti-fungal assay is an in vitro antifungal assay.
9. The VHH antibody according to statement 8, where the anti-fungal assay is a microtiter plate assay or leaf disc assay.
10. The VHH antibody according to any of statements 5 to 9 where the salt is a physiologically acceptable salt.
11. The VHH antibody according to any of statements 5 to 10 where the salt is a divalent salt.
12. The VHH antibody according to any of statements 5 to 11 where the salt is $MgCl_2$ or $CaCl_2$.
13. The VHH antibody according to any of statements 5 to 10 where the salt is a monovalent salt.
14. The VHH antibody according to statement 13 where the monovalent salt is NaCl.
15. The VHH antibody according to any of statements 5 to 12 where the elevated salt concentration is equal to or higher than 20 µM $MgCl_2$.
16. The VHH antibody according to any of statements 5 to 12 where the elevated salt concentration is equal to or higher than 150 µM $CaCl_2$.
17. The VHH antibody according to any of statements 5 to 10, 13 or 14 where the elevated salt concentration is equal to or higher than 100 mM NaCl.
18. The VHH antibody according to any of statements 1 to 17, where the VHH antibody is derived from a precursor polypeptide consisting of a cleavable leader peptide fused to the N-terminus of the VHH antibody.
19. The VHH antibody according to any of statements 1 to 18 where the VHH antibody comprises an N-terminal extension of amino acid residues derived from the cleavable leader peptide, as determined by mass spectrometry.
20. The VHH antibody according to statement 19 where the N-terminal extension is between 1 and 100 amino acids in length, 1 and 50 amino acids in length, between 1 and 20 amino acids in length, between 1 and 10 amino acids in length or between 1 and 5 amino acids in length.
21. The VHH antibody according to statement 19 where the N-terminal extension is 1 amino acid in length, 2 amino acid in length, 3 amino acids in length, 4 amino acid in length, or 5 amino acids in length.
22. The VHH antibody according to any of statements 18 to 21 where the cleavable leader peptide is an alfa mating factor pre-pro sequence.
23. The VHH antibody according to any one of statements 5 to 22 wherein the VHH antibody is a VHH antibody of any one of statements 1 to 4.
24. A nucleic acid encoding the VHH antibody according to any one of statements 1 to 22.
25. The nucleic acid according to statement 24 where the nucleic acid comprises or consists of the nucleotide sequence of SEQ ID NO:1, encoding the amino acid sequence of SEQ ID NO: 2.
26. A codon optimized nucleic acid encoding the VHH antibody according to any one of statements 1 to 22, wherein the codons are optimized for expression in a microorganism selected from the group consisting of *Komagataella* sp., *Trichoderma* sp., *Aspergillus* sp. and *Bacillus* sp.
27. A codon optimized nucleic acid encoding the VHH antibody according to any of statements 1 to 22, selected from the nucleotide sequence of the group consisting of SEQ ID NOs: 10 to 15 or a nucleotide sequence having at least 60% identity to SEQ ID NO: 1, encoding the amino acid sequence of SEQ ID NO: 2.
28. A composition comprising a VHH antibody as defined in any preceding statement and/or the variant VHH antibody according to statement 76.
29. The composition according to statement 28, wherein the composition is an agrochemical composition.
30. The composition according to statement 29, wherein the composition further comprising at least one agrochemically suitable additive selected from the group consisting off diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and drift control agents.
31. The VHH antibody according to any one of statements 1 to 23 or the composition according to any one statements 28 to 30 or the nucleic acid according to statements 24 to 27, wherein said at least one fungal species is a plant pathogenic fungal species.
32. The VHH antibody or composition according to statement 31, wherein the genus of said plant pathogenic fungus is chosen from the group comprising *Alternaria, Ascochyta, Botrytis, Cercospora, Colletotrichum, Diplodia, Erysiphe, Fusarium, Gleosporium, Leptosphaeria, Gaeumanomyces, Helminthosporium, Macrophomina, Nectria, Oidium, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus,* and *Aspergillus.*
33. The VHH antibody or composition according to statement 32, wherein the plant pathogenic fungus is of the species chosen from the group comprising *Alternaria alternata, Alternaria aroborescens, Alternaria solani, Botrytis cinerea, Cercospora beticola Colletotrichum orbiculare, Colletotrichum gloeosporioides, Colletotrichum lindemuthianum, Colletotrichum coccodes, Colletotrichum musea, Colletotrichum fruticola, Fusarium graminearum, Fusarium culmorum, Fusarium oxysporum, Penicillium digitatum, Penicillium Italicum, Phakopsora pachvrhizi, Uncinula necator, Oidium neolycopersici, Podosphaera aphanis* and *Podosphaera xanthii.*
34. A composition comprising at least one VHH antibody, which VHH antibody comprises the amino acid sequence set out in SEQ ID NO: 2 and which VHH antibody is capable of binding to a fungus for use as an anti-fungal agent.
35. A composition comprising at least one VHH antibody, which VHH antibody comprises the amino acid sequence set out in SEQ ID NO: 2 and which VHH antibody is capable of binding to a fungus for use in the treatment of a fungal infection.
36. A composition comprising at least one VHH antibody, which VHH antibody comprises a CDR1 region having the amino acid sequence set out in SEQ ID NO: 3, a CDR2 region having the amino acid sequence set out in SEQ ID NO: 4, and a CDR3 region having the amino acid sequence set out in SEQ ID NO: 5 and which VHH antibody is capable of binding to a fungus for use as an anti-fungal agent.

37. A composition comprising at least one VHH antibody, which VHH antibody comprises a framework region 1 (FR1) sequence comprising or consisting of the sequence set out SEQ ID NO: 6, a framework region 2 (FR2) sequence comprising or consisting of the sequence set out in SEQ ID NO: 7, a framework region 3 (FR3) sequence comprising or consisting of the sequence set out in SEQ ID NO: 8, and a framework region 4 (FR4) sequence comprising or consisting of the sequence set out in SEQ ID NO: 9 for use as an anti-fungal agent.

38. The composition according to any one of statements 28 to 30, for use as an anti-fungal agent.

39. The VHH antibody according to any one of statements 1 to 23 or 76, for use as an anti-fungal agent.

40. Use of a composition according to any one of statements 28 to 30, or a VHH antibody of any one of statements 1 to 23, as an anti-fungal agent.

41. Use according to any one of statements 38 to 40 as an anti-fungal agent on plants.

42. Use of a composition according to statement 40 as an anti-fungal agent against a plant fungal pathogen.

43. A method for protecting or treating a plant or a part of said plant from an infection with a plant pathogenic fungus, at least comprising the step of applying directly or indirectly to said plant or to a part of said plant, a composition according to any one of statements 28 to 30 or a VHH antibody according to any one of statements 1 to 23 or 76, under conditions effective to protect or treat said plant or a part of said plant against said infection with said plant pathogenic fungus.

44. An integrated pest management method for protection or treating a plant or part of said plant from an infection with a plant pathogenic fungus, at least comprising the step of applying directly or indirectly to said plant or to a part of said plant, a composition according to any one of statements 28 to 30 or a VHH antibody of any one of statements 1 to 23 or 76, and applying directly or indirectly to said plant or to a part of said plant one or more agrochemicals, under conditions effective to protect or treat said plant or a part of said plant against said infection with said plant pathogenic fungus.

45. The integrated pest management method according to statement 44 whereby the composition or VHH antibody and/or the agrochemical are applied at a reduced dose rate or at a reduced application frequency.

46. The integrated pest management method according to statement 44 or 45, where the composition or VHH antibody and the agrochemical have different modes of action.

47. A post-harvest treatment method for protecting or treating a harvested plant or a harvested part of said plant from an infection with a plant pathogenic fungus, at least comprising the step of applying directly or indirectly to said harvested plant or to a harvested part of said plant, a composition according to any one of statements 28 to 30 or a VHH antibody according to any one of statements 1 to 23 or 76, under conditions effective to protect or treat said harvested plant or a harvested part of said plant against said infection with said plant pathogenic fungus.

48. A method of inhibiting or killing the growth of a plant pathogenic fungus, comprising at least the step of applying directly or indirectly to a plant or to a part of said plant, a composition according to any of one of statements 28 to 30 or a VHH antibody of any one of statements 1 to 23 or 76.

49. A method for obtaining a VHH antibody which method comprises:
    a. obtaining a genetic library of VHH encoding nucleotide sequences,
    b. displaying said genetic library,
    c. selecting from the displayed genetic library VHH molecules binding to at least one fungal species,
    d. selecting from the VHH molecules that bind to at least one fungal species the VHH molecules that cause retardation of growth of a spore of the at least one fungal species and/or lysis of a spore of the at least one fungal species in the presence of elevated salt concentrations,
    e. identifying the nucleotide or amino acid sequence information linked to the VHH molecules binding to the at least one fungal species,
    f. expressing said nucleotide or amino acid sequence, thereby to prepare a VHH antibody which binds to and/or has affinity to at least one fungal species and whereby the VHH antibody causes retardation of growth of a spore of the at least one fungal species and/or lysis of a spore of the at least one fungal species in the presence of elevated salt concentrations.

50. The method according to statement 49, where the VHH antibody causes retardation of the growth of a spore of the at least one fungal species and/or lysis of a spore of the at least one fungal species in the presence of elevated salt concentrations when tested in an anti-fungal assay.

51. The method according to statement 49, where the retardation of the growth of a spore of the at least one fungal species and/or lysis of a spore of the at least one fungal species is improved at elevated salt concentrations relative to a VHH antibody that was not selected to cause retardation of growth of a spore of the at least one fungal species and/or lysis of a spore of the at least one fungal species in the presence of elevated salt concentrations when tested in an anti-fungal assay.

52. The method according to statements 50 or 51, where the anti-fungal assay is an in vitro antifungal assay.

53. The method according to any one of statement 50 to 52, where the anti-fungal assay is a microtiter plate assay or leaf disc assay.

54. The method according to any one of statements 49 to 53, where the salt is a physiologically acceptable salt.

55. The method according to any one of statements 49 to 54, where the salt is a divalent salt.

56. The method according to statement 55, where the salt is $MgCl_2$ or $CaCl_2$.

57. The method according to any one of statements 49 to 54, where the salt is a monovalent salt.

58. The method according to statement 57, where the salt is NaCl.

59. The method according to any one of statements 49 to 56, where the elevated salt concentration is equal to or higher than 20 μM $MgCl_2$.

60. The method according to any one of statements 49 to 56, where the elevated salt concentration is equal to or higher than 150 μM $CaCl_2$.

61. The method according any one of statements 49 to 54, or 57 or 58, where the elevated salt concentration is equal to or higher than 100 mM NaCl.
62. A method for obtaining a variant of the VHH antibody of any of statements 1 to 23, comprising the steps of:
    a. selecting a nucleic acid sequence encoding the VHH antibody of any of statements 1 to 23;
    b. modifying the selected nucleic acid sequence encoding the VHH antibody to obtain, when expressed, at least one variant VHH antibody;
    c. transforming host cells or unicellular organisms with the modified nucleic acid sequence to express a variant VHH antibody encoded by the modified nucleic acid sequence;
    d. assessing the ability of the variant VHH antibody to bind to at least one fungal species;
    e. where the variant VHH antibody is not capable of binding to at least one fungal species, repeating the process of steps (a) to (d) until a variant VHH antibody capable of binding to at least one fungal species;
    f. where the variant VHH antibody capable of binding to at least one fungal species was identified in step (d), isolating the corresponding modified nucleic acid sequence obtained in step (b) and expressing said nucleic acid to prepare a variant VHH antibody which binds to the at least one fungal species;
    g. optionally, isolating and/or purifying the variant VHH antibody;
    h. optionally, further manufacturing, isolating and purifying the variant VHH antibody.
63. The method according to statement 62, including an additional step between step d and e consisting of screening the variant VHH antibody for at least one modified and/or improved property.
64. The method according to statement 62 or 63, where the variant VHH antibody causes retardation of the growth of a spore of the at least one fungal species and/or lysis of a spore of the at least one fungal species in the presence of elevated salt concentrations when tested in an anti-fungal assay.
65. The method according to any one of statements 62 to 64, where the retardation of the growth of a spore of the at least one fungal species and/or lysis of a spore of the at least one fungal species is improved at elevated salt concentrations relative to a VHH antibody that was not selected to cause retardation of growth of a spore of the at least one fungal species and/or lysis of a spore of the at least one fungal species in the presence of elevated salt concentrations when tested in an anti-fungal assay.
66. The method according to statements 64 or 65, where the anti-fungal assay is an in vitro antifungal assay.
67. The method according to any one of statements 64 to 66, where the anti-fungal assay is a microtiter plate assay or leaf disc assay.
68. The method according to any one of statements 64 to 67 where the salt is a physiologically acceptable salt.
69. The method according to statement 68 where the salt is a divalent salt.
70. The method according to statement 69 where the physiologically acceptable salt is $MgCl_2$ or $CaCl_2$.
71. The method according to any one of statements 64 to 68 where the salt is a monovalent salt.
72. The method according to statement 71 where the monovalent salt is NaCl.
73. The method according to any one of statements 64 to 69 where the elevated salt concentration is equal to or higher than 20 µM $MgCl_2$.
74. The method according to any one of statements 64 to 69 where the elevated salt concentration is equal to or higher than 150 µM $CaCl_2$.
75. The method according to any one of statements 64 to 68, or 71 or 72, where the elevated salt concentration is equal to or higher than 100 mM NaCl.
76. A variant VHH antibody obtainable by the method of any one of statements 62 to 75.
77. A method for the preparation of an anti-fungal composition, which method comprises: preparing an anti-fungal VHH antibody according to the method of any one of statements 49 to 75; and combining the anti-fungal VHH antibody with one or more suitable carriers and/or one or more suitable additives.
78. The method according to statement 77, where the one or more suitable carrier and/or one or more suitable additives are pharmaceutically acceptable.
79. The method according to statement 77, where the one or more suitable carrier and/or one or more suitable additives are agrochemically suitable.
80. The method according to any one of statements 78 to 79, where the one or more suitable carrier and/or one or more suitable additives are selected from the group consisting off diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and drift control agents.
81. A mixture comprising at least one VHH antibody according to any one of statements 1 to 23, and at least one agrochemical.
82. A transgenic plant, plant part, seed, or plant cell comprising a nucleic acid sequence encoding a VHH antibody as defined in any one of statements 1 to 23 or a nucleic acid sequence according to any of statements 24 to 27.
83. A vector comprising a nucleic acid sequence encoding a VHH antibody as defined in any one of statements 1 to 23 or a nucleic acid sequence according to any of statements 24 to 27.
84. A host cell comprising a nucleic acid sequence encoding a VHH antibody as defined in any one of statements 1 to 23 or a nucleic acid sequence according to any of statements 24 to 27 or a vector according to statement 83.
85. A method for the production of a VHH antibody, comprising culturing a host cell according to statement 84 under conditions to induce expression of the vector or plasmid, and optionally isolating the VHH antibody from the culture medium or fermentation broth.
86. The methods according to any one of statements 49 to 61, 62 to 75 or 77 to 80, wherein said at least one fungal species is a plant pathogenic fungal species.
87. The methods according to 86, wherein the genus of said plant pathogenic fungus is chosen from the group comprising *Alternaria, Ascochyta, Botrytis, Cercospora, Colletotrichum, Diplodia, Erysiphe, Fusarium, Gleosporium, Leptosphaeria, Gaeumanomyces, Helminthosporium, Macrophomina, Nectria, Oidium, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blume-* ria, *Mycosphaerella, Ustilago, Melampsora, Phakospora, Monilinia, Mucor, Rhizopus*, and *Aspergillus*.

88. The methods according to statement 87, wherein the plant pathogenic fungus is of the species chosen from the group comprising *Alternaria alternata, Alternaria aroborescens, Alternaria solani, Botrytis cinerea, Cercospora beticola Colletotrichum orbiculare, Colletotrichum gloeosporioides, Colletotrichum lindemuthianum, Colletotrichum coccodes, Colletotrichum musea, Colletotrichum fruticola, Fusarium graminearum, Fusarium culmorum, Fusarium oxysporum, Penicillium digitatum, Penicillium Italicum, Phakopsora pachvrhizi, Uncinula necator, Oidium neolycopersici, Podosphaera aphanis* and *Podosphaera xanthii*.

89. The VHH antibody according to any one of statements 1 to 23 or 76, wherein the VHH antibody binds to *Botrytis cinerea*.

90. A method for treating a plant comprising the step of applying a composition comprising the VHH antibody according to any one of statements 1 to 23 or 76 to the plant.

91. The method of statement 90, wherein the VHH antibody binds to *Botrytis cinerea*.

92. The method of statement 90 or 91, wherein the VHH antibody is applied at a concentration from 5 to 110 µM.

93. The method of any of statements 90 to 92, wherein said method comprises treating a plant field.

94. The method of statement 93, wherein the VHH antibody is applied at a concentration from 100 g/ha to 400 g/ha.

95. A method comprising applying a composition comprising the VHH antibody of statement 1 to 23, 76, or 89 to a surface.

96. The method of statement 95, wherein said surface is the leaf of a plant.

We claim:

1. A VHH antibody that binds to at least one fungal species, wherein the VHH antibody comprises the amino acid sequence set out in SEQ ID NO: 2.

2. The VHH antibody according to claim 1, wherein the VHH antibody is derived from a precursor polypeptide consisting of a cleavable leader peptide fused to the N-terminus of the VHH antibody.

3. The VHH antibody according to claim 1, wherein said at least one fungal species is a plant pathogenic fungus, wherein the genus of said plant pathogenic fungus is chosen from the group consisting of *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus,* and *Aspergillus*.

4. The VHH antibody according to claim 3, wherein the plant pathogenic fungus is *Botrytis cinerea*.

5. An agrochemical composition comprising at least one VHH antibody according to claim 1, further comprising at least one agrochemically suitable additive selected from the group consisting of diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and drift control agents.

6. A method comprising applying the agrochemical composition according to claim 5 to a surface.

7. The method of claim 6, wherein said surface is the leaf of a plant.

8. The method according to claim 7, wherein said method comprises treating a plant field.

9. The method according to claim 8, wherein the VHH antibody is applied at an application rate of from 100 g/ha to 400 g/ha of the VHH antibody.

10. The method according to claim 9, wherein the VHH antibody binds to *Botrytis cinerea*.

11. A post-harvest treatment method for protecting or treating a harvested plant or a harvested part of said plant from an infection with a plant pathogenic fungus, comprising a step of applying to said harvested plant or to a harvested part of said plant an agrochemical composition according to claim 5, under conditions effective to protect or treat said harvested plant or a harvested part of said plant against said infection with said plant pathogenic fungus.

12. The method according to claim 11, wherein the VHH antibody binds to *Botrytis cinerea*.

13. A method for the manufacturing of the VHH antibody according to claim 1, comprising culturing a host cell comprising a nucleic acid encoding the VHH antibody, wherein optionally the codons are optimized for expression in a microorganism selected from the group consisting of *Komagataella* sp., *Trichoderma* sp., *Aspergillus* sp. and *Bacillus* sp., wherein the host cell is cultured under conditions to induce expression of the VHH antibody, and isolating and/or purifying the VHH antibody from the culture.

* * * * *